US012709646B2

(12) United States Patent
Janssen et al.

(10) Patent No.: US 12,709,646 B2
(45) Date of Patent: Aug. 18, 2026

(54) POLYPEPTIDES COMPRISING IMMUNOGLOBULIN SINGLE VARIABLE DOMAINS TARGETING GLYPICAN-3 AND T CELL RECEPTOR

(71) Applicants: Ablynx N.V., Zwijnaarde (BE); Sanofi, Paris (FR)

(72) Inventors: Daniel Janssen, Mortsel (BE); Carlo Boutton, Wielsbeke (BE); Evelyne Dombrecht, Zwijnaarde (BE); Bram Laukens, Zwijnaarde (BE); Paolo Meoni, Zwijnaarde (BE); Lily Pao, Bridgewater, NJ (US); Jan Pype, Herne (BE); Peter Schotte, De Pinte (BE); Benedikte Serruys, Sint-Michiels (BE); Ana Paula Vintem, Zwijnaarde (BE); Diane Van Hoorick, Zwijnaarde (BE)

(73) Assignees: Ablynx NV, Zwijnaarde (BE); Sanofi, Paris (FR)

( * ) Notice: Subject to any disclaimer, the term of this patent is extended or adjusted under 35 U.S.C. 154(b) by 0 days.

(21) Appl. No.: 18/432,750

(22) Filed: Feb. 5, 2024

(65) Prior Publication Data

US 2024/0343823 A1 Oct. 17, 2024

Related U.S. Application Data

(63) Continuation of application No. 17/553,908, filed on Dec. 17, 2021, now Pat. No. 11,932,702.

(60) Provisional application No. 63/127,224, filed on Dec. 18, 2020.

(30) Foreign Application Priority Data

Dec. 21, 2020 (EP) .................................... 20306633

(51) Int. Cl.
*C07K 16/30* (2006.01)
*A61P 35/00* (2006.01)
*C07K 16/28* (2006.01)
*A61K 39/00* (2006.01)

(52) U.S. Cl.
CPC ............ *C07K 16/303* (2013.01); *A61P 35/00* (2018.01); *C07K 16/2809* (2013.01); *A61K 2039/505* (2013.01); *C07K 2317/31* (2013.01); *C07K 2317/33* (2013.01); *C07K 2317/565* (2013.01); *C07K 2317/569* (2013.01); *C07K 2317/73* (2013.01); *C07K 2317/92* (2013.01); *C07K 2319/30* (2013.01)

(58) Field of Classification Search
CPC ...................... C07K 16/2809; C07K 2317/569
See application file for complete search history.

(56) References Cited

U.S. PATENT DOCUMENTS

| | | | |
|---|---|---|---|
| 11,932,702 B2 | 3/2024 | Janssen et al. | |
| 2010/0136018 A1 | 6/2010 | Dolk et al. | |
| 2017/0137517 A1 | 5/2017 | Bowman et al. | |
| 2017/0190769 A1 | 7/2017 | Buyse et al. | |
| 2019/0112392 A1 | 4/2019 | Roobrouck et al. | |
| 2024/0409663 A1* | 12/2024 | Yang .................... | C07K 16/303 |

FOREIGN PATENT DOCUMENTS

| | | | |
|---|---|---|---|
| EP | 1674111 | A1 | 6/2006 |
| EP | 2522724 | A1 | 11/2012 |
| EP | 3199628 | A1 | 8/2017 |
| EP | 3431102 | A1 | 1/2019 |
| RU | 2606264 | C2 | 1/2017 |
| WO | WO 1994/004678 | A1 | 3/1994 |
| WO | WO 1996/034103 | A1 | 10/1996 |
| WO | WO 1999/023221 | A2 | 5/1999 |
| WO | WO 2004/041865 | A2 | 5/2004 |
| WO | WO 2006/122787 | A1 | 11/2006 |
| WO | WO 2007/118670 | A1 | 10/2007 |
| WO | WO 2008/020079 | A1 | 2/2008 |
| WO | WO 2009/012394 | A1 | 1/2009 |
| WO | WO 2011/078332 | A1 | 6/2011 |
| WO | WO 2012/016073 | A2 | 2/2012 |
| WO | WO 2012/175400 | A1 | 12/2012 |
| WO | WO 2012/175741 | A2 | 12/2012 |
| WO | WO 2015/173325 | A2 | 11/2015 |
| WO | WO 2016/047722 | A1 | 3/2016 |
| WO | WO 2016/180969 | A1 | 11/2016 |
| WO | WO 2017/068186 | A1 | 4/2017 |
| WO | WO 2017/080850 | A1 | 5/2017 |
| WO | WO 2017/085172 | A2 | 5/2017 |
| WO | WO 2017/159287 | A1 | 9/2017 |
| WO | WO 2018/091606 | A1 | 5/2018 |
| WO | WO 2018/104444 | A1 | 6/2018 |

(Continued)

OTHER PUBLICATIONS

Almagro JC, Fransson J. Humanization of antibodies. Front Biosci. Jan. 1, 2008;13:1619-33. (Year: 2008).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

Edwards et al. The remarkable flexibility of the human antibody repertoire; isolation of over one thousand different antibodies to a single protein, BLyS. J Mol Biol Nov. 14, 2003;334(1):103-18. (Year: 2003).*

(Continued)

*Primary Examiner* — Aurora M Fontainhas
*Assistant Examiner* — Jennifer A Benavides
(74) *Attorney, Agent, or Firm* — Wolf, Greenfield & Sacks, P.C.

(57) ABSTRACT

The present technology aims at providing a novel type of drug for treating a subject suffering from cancer. Specifically, the technology provides polypeptides comprising at least four immunoglobulin single variable domains (ISVDs), characterized in that one ISVD binds to TCR and at least two ISVDs bind to GPC3. The present technology also provides nucleic acids, vectors and compositions.

10 Claims, 24 Drawing Sheets

Figure 1A:
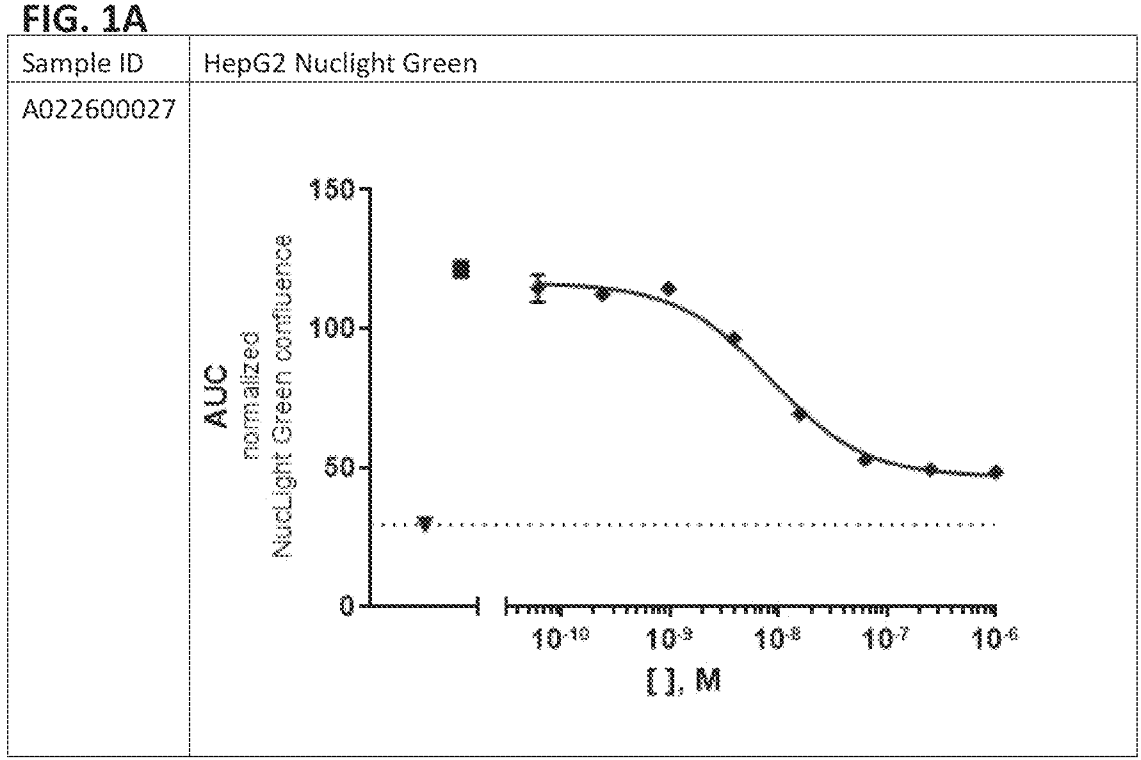

Specification includes a Sequence Listing.

(56) References Cited

FOREIGN PATENT DOCUMENTS

| | | | |
|---|---|---|---|
| WO | WO 2018/134234 | A1 | 7/2018 |
| WO | WO 2018/134235 | A1 | 7/2018 |
| WO | WO 2018/220235 | A1 | 12/2018 |
| WO | WO 2019/092451 | A1 | 5/2019 |
| WO | WO 2022/129560 | A1 | 6/2022 |
| WO | WO 2023/111266 | A1 | 6/2023 |

OTHER PUBLICATIONS

Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*

Kussie et al. A single engineered amino acid substitution changes antibody fine specificity.J Immunol. Jan. 1, 1994;152(1):146-52. (Year: 1994).*

Rudikoff S et al. Single amino acid substitution altering antigen-binding specificity. Proc Natl Acad Sci U S A. Mar. 1982;79(6):1979-83. (Year: 1982).*

Wu et al. Humanization of a murine monoclonal antibody by simultaneous optimization of framework and CDR residues. J Mol Biol. Nov. 19, 1999;294(1):151-62. (Year: 1999).*

Extended European Search Report, EP 20306633.7, Jun. 8, 2021.

Abdiche et al., Determining kinetics and affinities of protein interactions using a parallel real-time label-free biosensor, the Octet. Anal Biochem. Jun. 15, 2008;377(2):209-17. doi: 10.1016/j.ab.2008.03.035. Epub Mar. 25, 2008.

Blackwell et al., Impact of communication topology in particle swarm optimization. J Latex Class Files. Aug. 2015;14(8). 64 pages.

Call et al., Molecular mechanisms for the assembly of the T cell receptor-CD3 complex. Mol Immunol. Apr. 2004;40(18):1295-305. doi: 10.1016/j.molimm.2003.11.017.

Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.

Conrath et al., Camel single-domain antibodies as modular building units in bispecific and bivalent antibody constructs. J Biol Chem. Mar. 9, 2001;276(10):7346-50. doi: 10.1074/jbc.M007734200. Epub Oct. 25, 2000.

Davies et al., 'Camelising' human antibody fragments: NMR studies on VH domains. FEBS Lett. Feb. 21, 1994;339(3):285-90. doi: 10.1016/0014-5793(94)80432-x.

Davies et al., Single antibody domains as small recognition units: design and in vitro antigen selection of camelized, human VH domains with improved protein stability. Protein Eng. Jun. 1996;9(6):531-7. doi: 10.1093/protein/9.6.531.

Detre et al., A "quickscore" method for immunohistochemical semiquantitation: validation for oestrogen receptor in breast carcinomas. J Clin Pathol. Sep. 1995;48(9):876-8. doi: 10.1136/jcp.48.9.876.

Drake et al., Characterizing high-affinity antigen/antibody complexes by kinetic- and equilibrium-based methods. Anal Biochem. May 1, 2004;328(1):35-43. doi: 10.1016/j.ab.2003.12.025.

Feng et al., Therapeutically targeting glypican-3 via a conformation-specific single-domain antibody in hepatocellular carcinoma. Proc Natl Acad Sci U S A. Mar. 19, 2013;110(12):E1083-91. doi: 10.1073/pnas.1217868110. Epub Mar. 5, 2013.

Fleming et al., Engineered Anti-GPC3 Immunotoxin, HN3-ABD-T20, Produces Regression in Mouse Liver Cancer Xenografts Through Prolonged Serum Retention. Hepatology. May 2020;71(5):1696-1711. doi: 10.1002/hep.30949. Epub Jan. 27, 2020.

Fraley et al., The Gyrolab™ immunoassay system: a platform for automated bioanalysis and rapid sample turnaround. Bioanalysis. Jul. 2013;5(14):1765-74. doi: 10.4155/bio.13.145.

Glennie et al., Preparation and performance of bispecific F(ab' gamma)2 antibody containing thioether-linked Fab' gamma fragments. J Immunol. Oct. 1, 1987;139(7):2367-75.

Hamers-Casterman et al., Naturally occurring antibodies devoid of light chains. Nature. Jun. 3, 1993;363(6428):446-8. doi: 10.1038/363446a0.

Johnsson et al., Comparison of methods for immobilization to carboxymethyl dextran sensor surfaces by analysis of the specific activity of monoclonal antibodies. J Mol Recognit. Jan. 1995-Apr;8(1-2):125-31. doi: 10.1002/jmr.300080122.

Johnsson et al., Immobilization of proteins to a carboxymethyldextran-modified gold surface for biospecific interaction analysis in surface plasmon resonance sensors. Anal Biochem. Nov. 1, 1991;198(2):268-77. doi: 10.1016/0003-2697(91)90424-r.

Jonsson et al., Introducing a biosensor based technology for real-time biospecific interaction analysis. Ann Biol Clin (Paris). 1993;51(1):19-26.

Jonsson et al., Real-time biospecific interaction analysis using surface plasmon resonance and a sensor chip technology. Biotechniques. Nov. 1991;11(5):620-7.

Kabat et al., Sequences of Proteins of Immunological Interest. vol. I. 5th Ed. US Department of Health and Human Services. Public Health Service. National Institutes of Health. 1991. 11 pages.

Klein et al., Design and characterization of structured protein linkers with differing flexibilities. Protein Eng Des Sel. Oct. 2014;27(10):325-30. doi: 10.1093/protein/gzu043.

Martin, Chapter 3: Protein Sequence and Structure Analysis of Antibody Variable Domains. In Antibody Engineering vol. 2. Springer Lab Manuals. Springer, Berlin, Heidelberg. 2010:33-51. doi: 10.1007/978-3-642-01147-4_3.

Muyldermans et al., Single domain camel antibodies: current status. J Biotechnol. Jun. 2001;74(4):277-302. doi: 10.1016/s1389-0352(01)00021-6.

Ober et al., Differences in promiscuity for antibody-FcRn interactions across species: implications for therapeutic antibodies. Int Immunol. Dec. 2001;13(12):1551-9. doi: 10.1093/intimm/13.12.1551.

Van Der Linden et al., Induction of immune responses and molecular cloning of the heavy chain antibody repertoire of Lama glama. J Immunol Methods. Jun. 23, 2000;240(1-2):185-95. doi: 10.1016/s0022-1759(00)00188-5.

Berry et al., Substitution of cysteine for selenocysteine in type I iodothyronine deiodinase reduces the catalytic efficiency of the protein but enhances its translation. Endocrinology. Oct. 1992;131(4):1848-52. doi: 10.1210/endo.131.4.1396330.

Colman, Effects of amino acid sequence changes on antibody-antigen interactions. Res Immunol. Jan. 1994;145(1):33-6. doi: 10.1016/s0923-2494(94)80039-1.

Dashivets et al., Oxidation in the complementarity-determining regions differentially influences the properties of therapeutic antibodies. MAbs. Nov./Dec. 2016;8(8):1525-1535. doi: 10.1080/19420862.2016.1231277. Epub Sep. 9, 2016.

Davies et al., Affinity improvement of single antibody VH domains: residues in all three hypervariable regions affect antigen binding. Immunotechnology. Sep. 1996;2(3):169-79. doi: 10.1016/s1380-2933(96)00045-0.

Gasser et al., Antibody production with yeasts and filamentous fungi: on the road to large scale? Biotechnol Lett. Feb. 2007;29(2):201-12. doi: 10.1007/s10529-006-9237-x. Epub Nov. 22, 2006.

Maeda et al., Engineering of functional chimeric protein G-Vargula luciferase. Anal Biochem. Jul. 1, 1997;249(2):147-52. doi: 10.1006/abio.1997.2181.

Muller et al., Spliceosomal peptide P140 for immunotherapy of systemic lupus erythematosus: results of an early phase II clinical trial. Arthritis Rheum. Dec. 2008;58(12):3873-83. doi: 10.1002/art.24027.

Riechmann et al., Reshaping human antibodies for therapy. Nature. Mar. 24, 1988;332(6162):323-7. doi: 10.1038/332323a0.

Safdari et al., Antibody humanization methods—a review and update. Biotechnol Genet Eng Rev. 2013;29:175-86. doi: 10.1080/02648725.2013.801235. Epub Aug. 2, 2013.

Torres et al., The immunoglobulin constant region contributes to affinity and specificity. Trends Immunol. Feb. 2008;29(2):91-7. doi: 10.1016/j.it.2007.11.004. Epub Jan. 10, 2008.

Vajdos et al., Comprehensive functional maps of the antigen-binding site of an anti-ErbB2 antibody obtained with shotgun

(56) References Cited

OTHER PUBLICATIONS scanning mutagenesis. J Mol Biol. Jul. 5, 2002;320(2):415-28. doi: 10.1016/S0022-2836(02)00264-4.
Badri et al., Optimization of radiation dosing schedules for proneural glioblastoma. J Math Biol. Apr. 2016;72(5):1301-36. doi: 10.1007/s00285-015-0908-x. Epub Jun. 21, 2015.
Ishiguro et al., An anti-glypican 3/CD3 bispecific T cell-redirecting antibody for treatment of solid tumors. Sci Transl Med. Oct. 4, 2017;9(410):eaal4291. doi: 10.1126/scitranslmed.aal4291.
Khan K., Gene expression in Mammalian cells and its applications. Adv Pharm Bull. 2013;3(2):257-63. doi: 10.5681/apb.2013.042. Epub Aug. 20, 2013.
Shen et al., Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.
Singer et al., Genes and Genomes: A Changing Perspective. World. 1998. Russian Translation from English. 6 pages.
Viola et al., Non-viral nanovectors for gene delivery: factors that govern successful therapeutics. Expert Opin Drug Deliv. Jun. 2010;7(6):721-35. doi: 10.1517/17425241003716810.
Muyldermans, Nanobodies: natural single-domain antibodies. Annu Rev Biochem. 2013;82:775-97. doi: 10.1146/annurev-biochem-063011-092449. Epub Mar. 13, 2013.

* cited by examiner

A022600096
(triangle symbol, dotted line)
A022600102
(square symbol, dotted line)
A022600103
(triangle symbol, solid line)
A022600104
(circle symbol, dotted line)
A022600105
(diamond symbol, solid line)
AUC
Normalized
NucLight Green confluence
150
100
50
0
10-12
10-11
10-10
10-9
10-8
10-7
10-6
[ ], M Sample ID
HepG2 on Incucyte
Huh7 on xCELLigence
A022600103
(solid line)
A022600167
(dotted line)
A022600122
(solid line)
A022600168
(dotted line)
AUC
Normalized
NucLight Green
NucLight Green confluence
[ ], M
Cell index
Concentration (M)

Figures 4A, 4B:
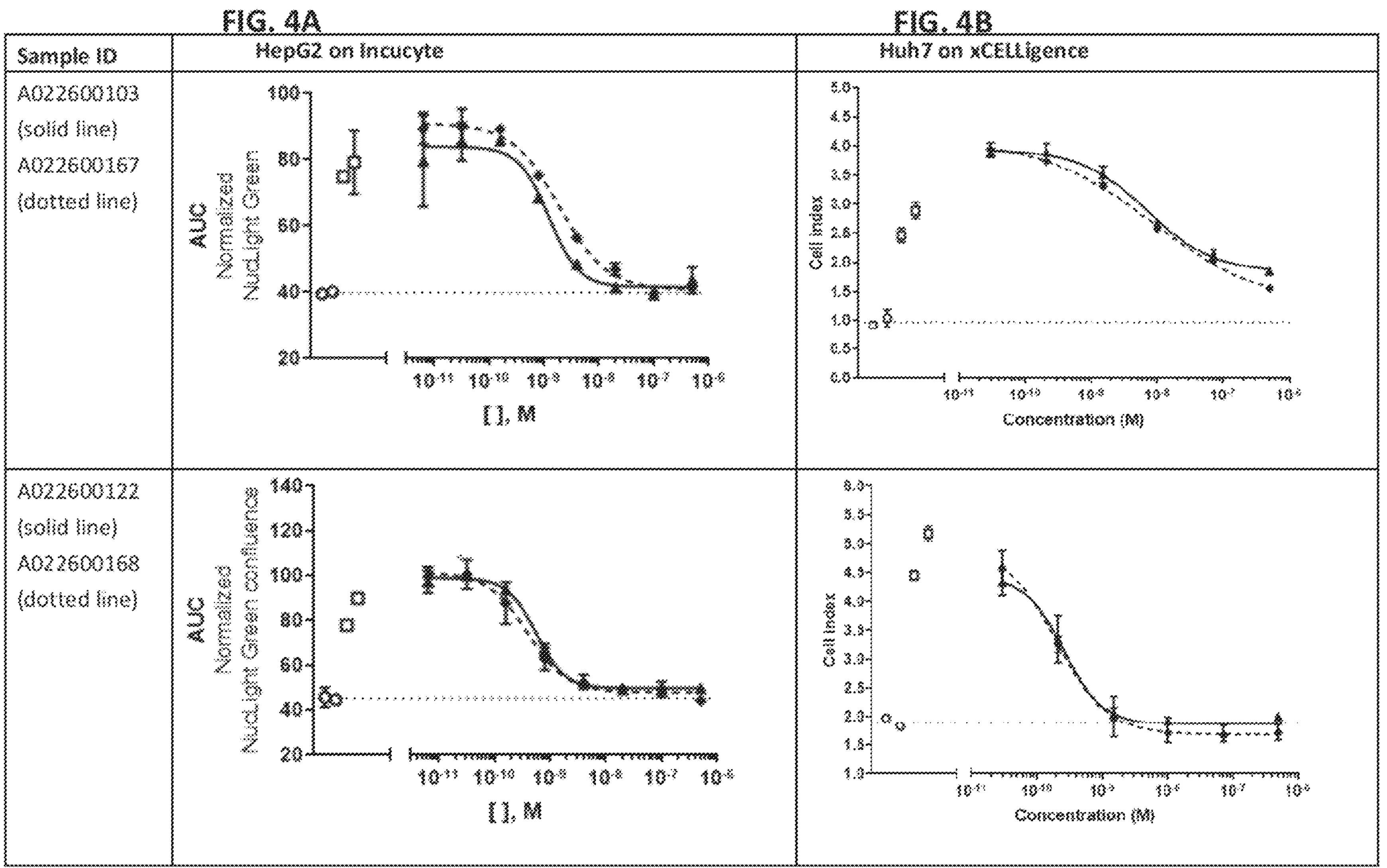

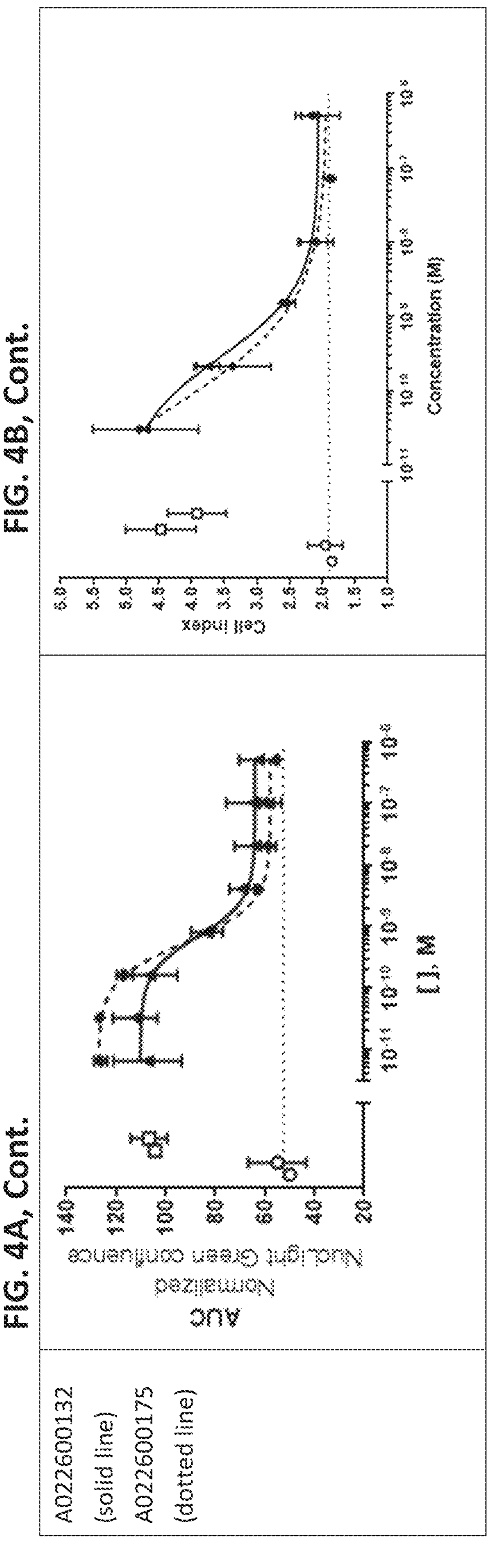
FIG. 4A, Cont.
FIG. 4B, Cont.

Figures 5A, 5B:
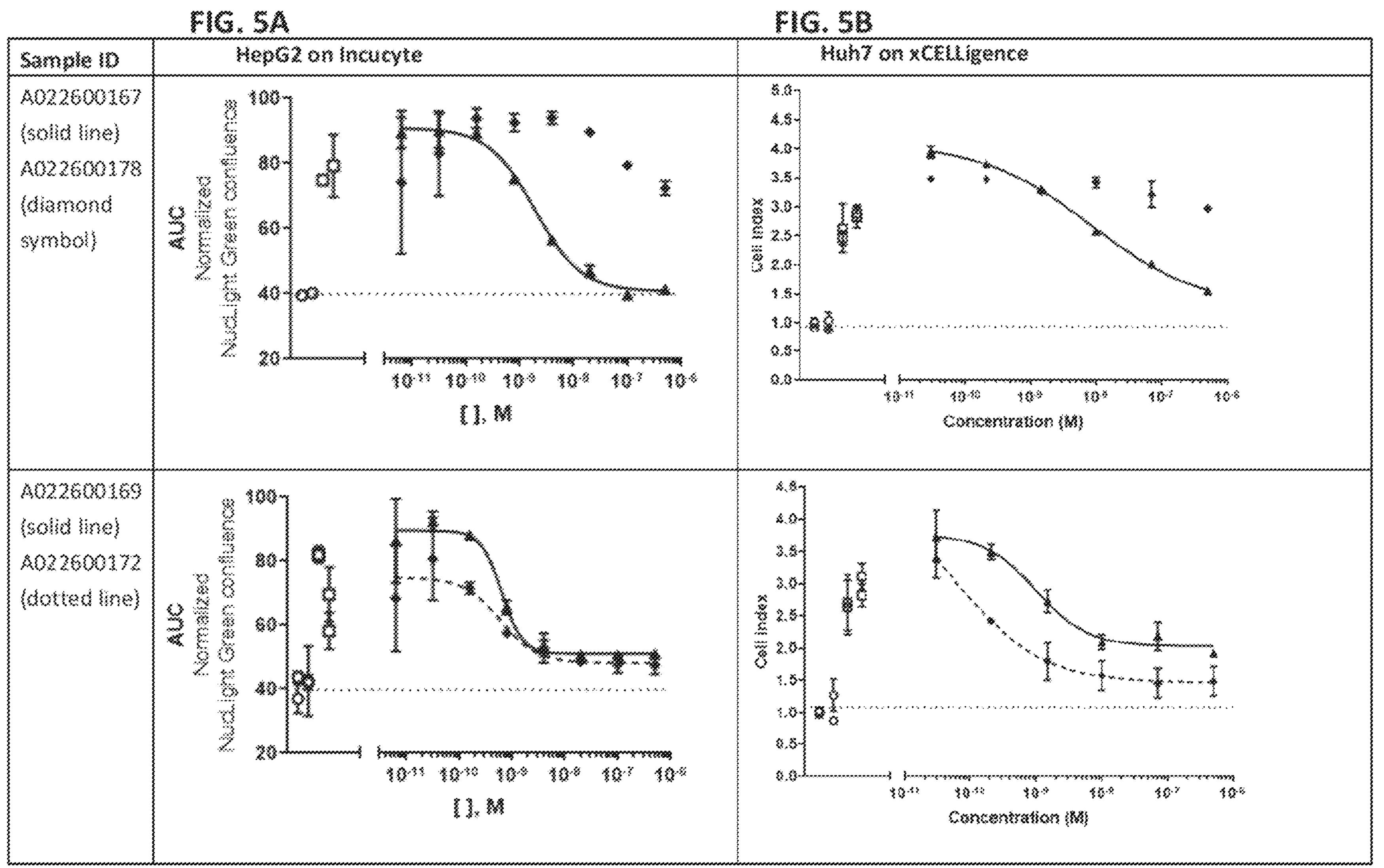

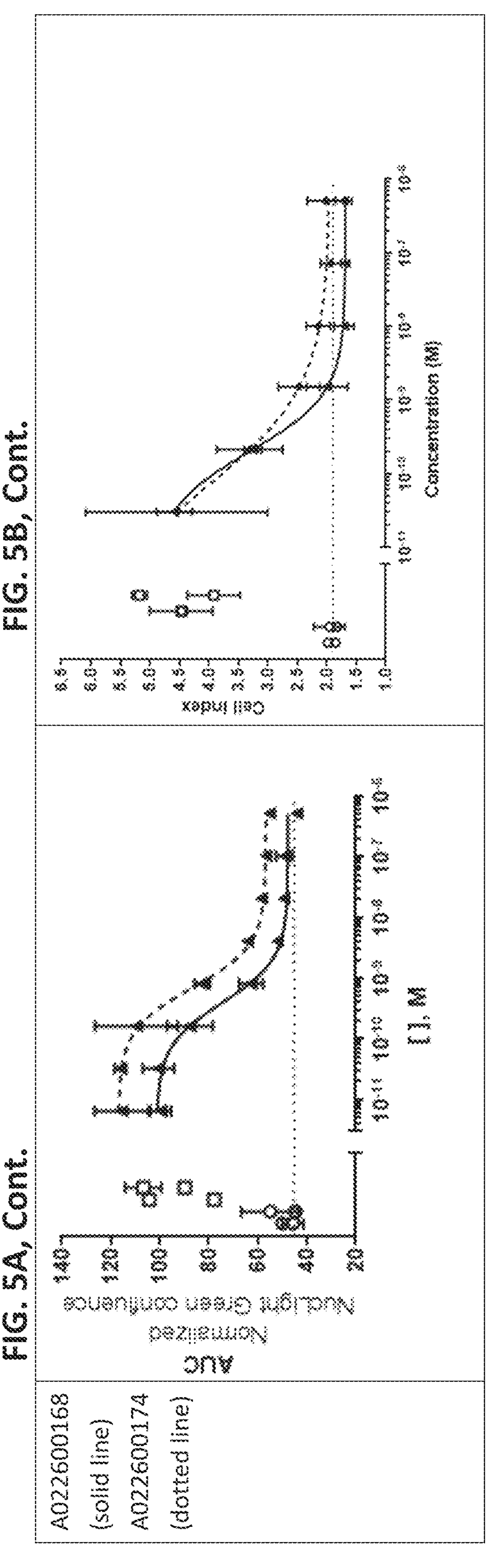
FIG. 5A, Cont.
FIG. 5B, Cont.

Sample ID
HepG2 on Incucyte
Huh7 on xCELLigence
A022600167
(solid line)
A022600179
(dotted line)
AUC
Normalized
NucLight Green confluence
[], M
Cell Index
Concentration (M)
A022600168
(solid line)
A022600170
(dotted line)
AUC
Normalised
NucLight Green confluence
[], M
Cell Index
Concentration (M)

Figures 6A, 6B:
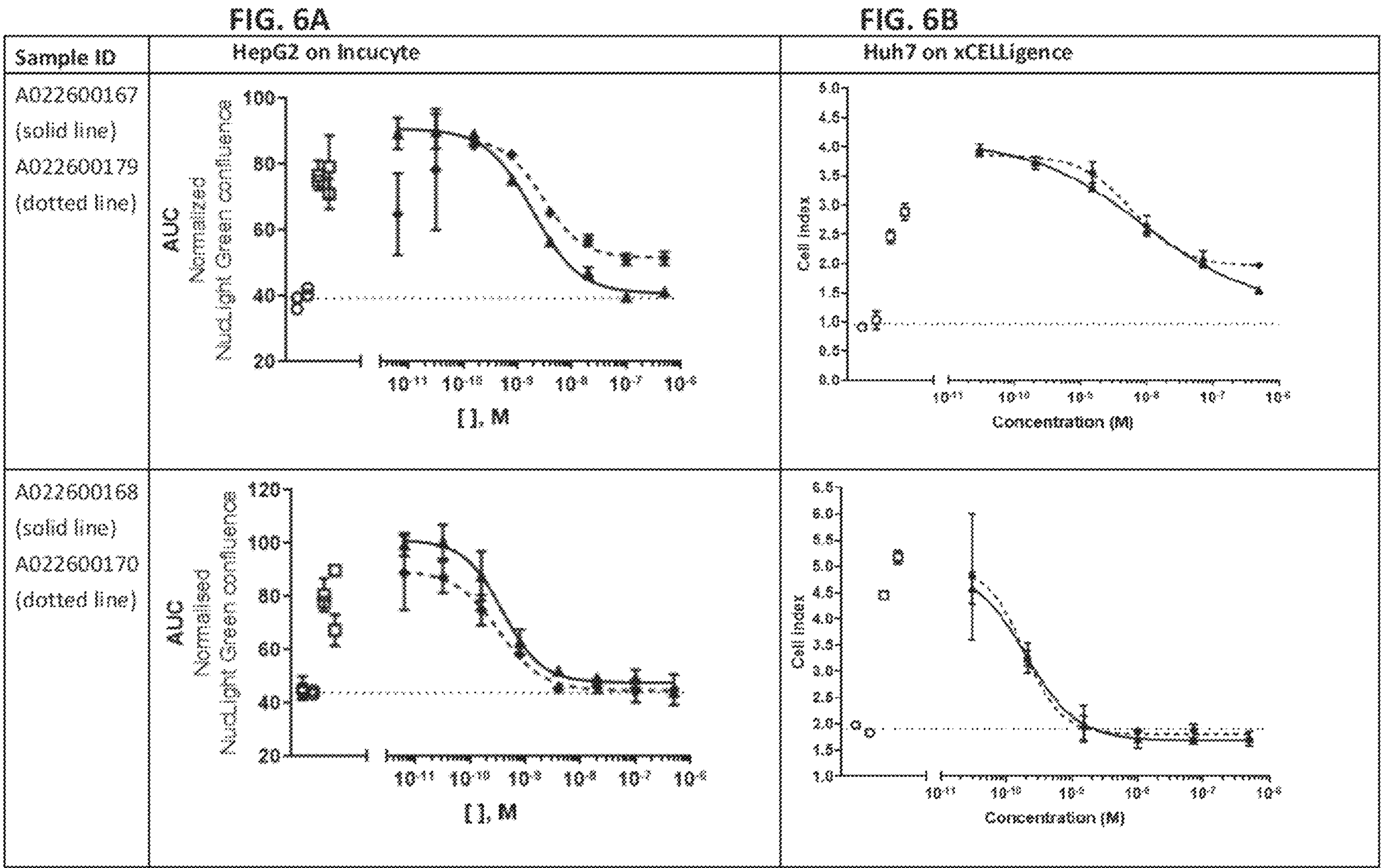

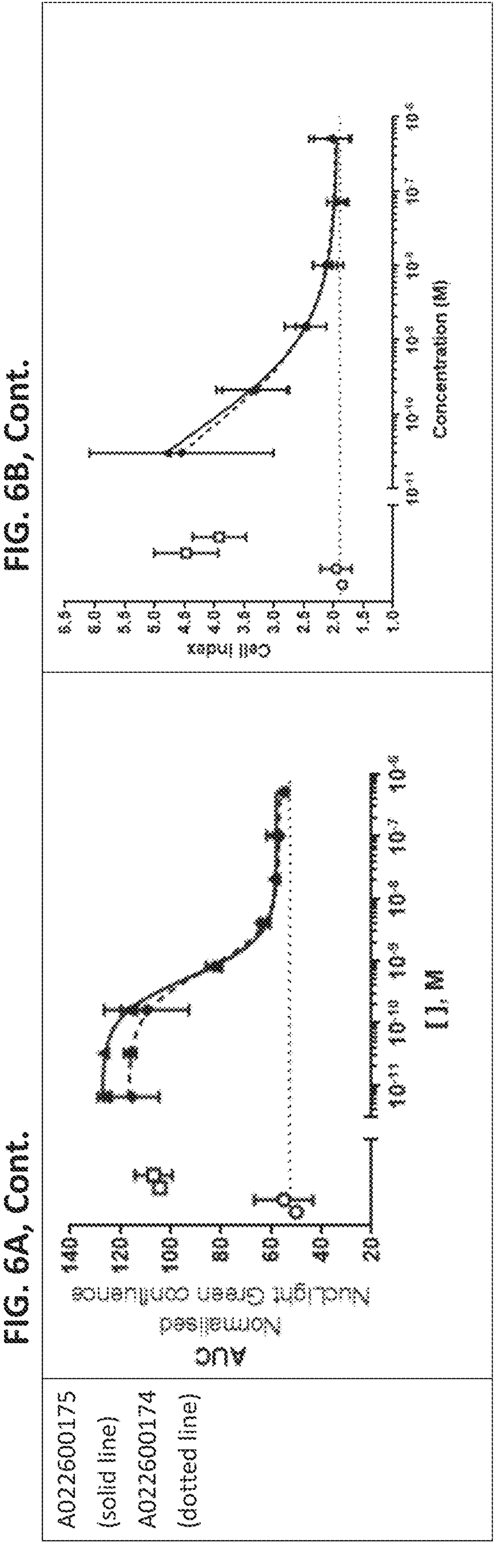
A022600175
(solid line)
A022600174
(dotted line)
FIG. 6A, Cont.
AUC
Normalised
NucLight Green confluence
140
120
100
80
60
40
20
[ ], M
FIG. 6B, Cont.
Cell Index
6.5
6.0
5.5
5.0
4.5
4.0
3.5
3.0
2.5
2.0
1.5
1.0
Concentration (M)

CD69+ upregulation in absence of target cells
No sGPC3 (circle symbol)
1 nM sGPC3 (triangle symbol)
10 nM sGPC3 (square symbol)
100 nM sGPC3 (diamond symbol)
% CD69 + T cells
0.0
0.1
0.2
0.3
0.4
0.5
0.6
isotype control
isotype control
Concentration (M)

HEPG2
Cell Index
Concentration (M)

NCI-H661
Cell Index
Concentration (M)
A022600167
(triangle symbol)
A022600168
(diamond
symbol)
T017000698
(circle symbol)
Ab2
(square symbol)

A022600167
(triangle symbol)
A022600168
(diamond
symbol)
T017000698
(circle symbol)
Ab2
(square symbol)

BxPC-3
Cell Index
Concentration (M)

NCI-H292
Cell Index
Concentration (M)

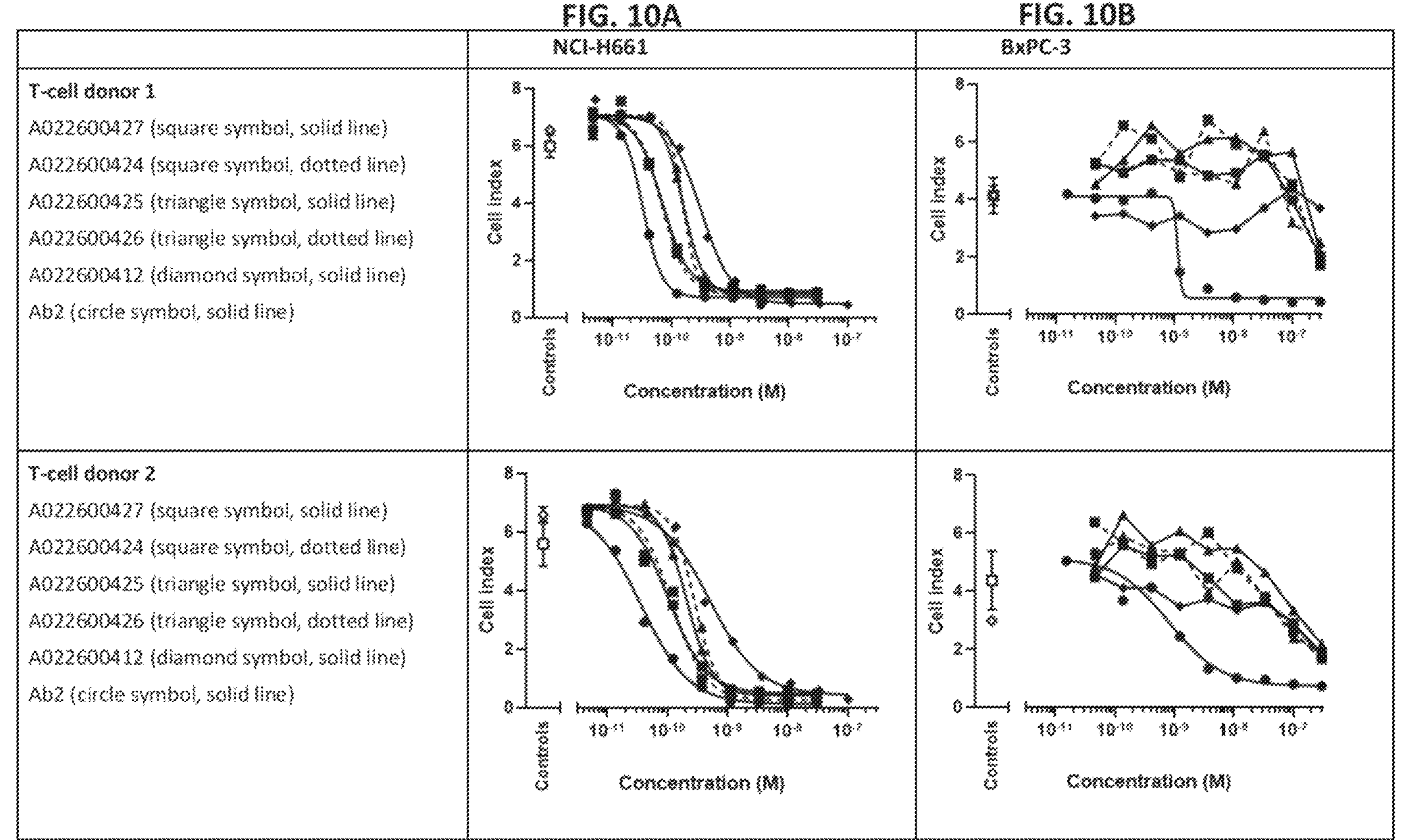
FIG. 10A
NCI-H661
FIG. 10B
BxPC-3
T-cell donor 1
A022600427 (square symbol, solid line)
A022600424 (square symbol, dotted line)
A022600425 (triangle symbol, solid line)
A022600426 (triangle symbol, dotted line)
A022600412 (diamond symbol, solid line)
Ab2 (circle symbol, solid line)
T-cell donor 2
A022600427 (square symbol, solid line)
A022600424 (square symbol, dotted line)
A022600425 (triangle symbol, solid line)
A022600426 (triangle symbol, dotted line)
A022600412 (diamond symbol, solid line)
Ab2 (circle symbol, solid line)
Cell index
Controls
Concentration (M)

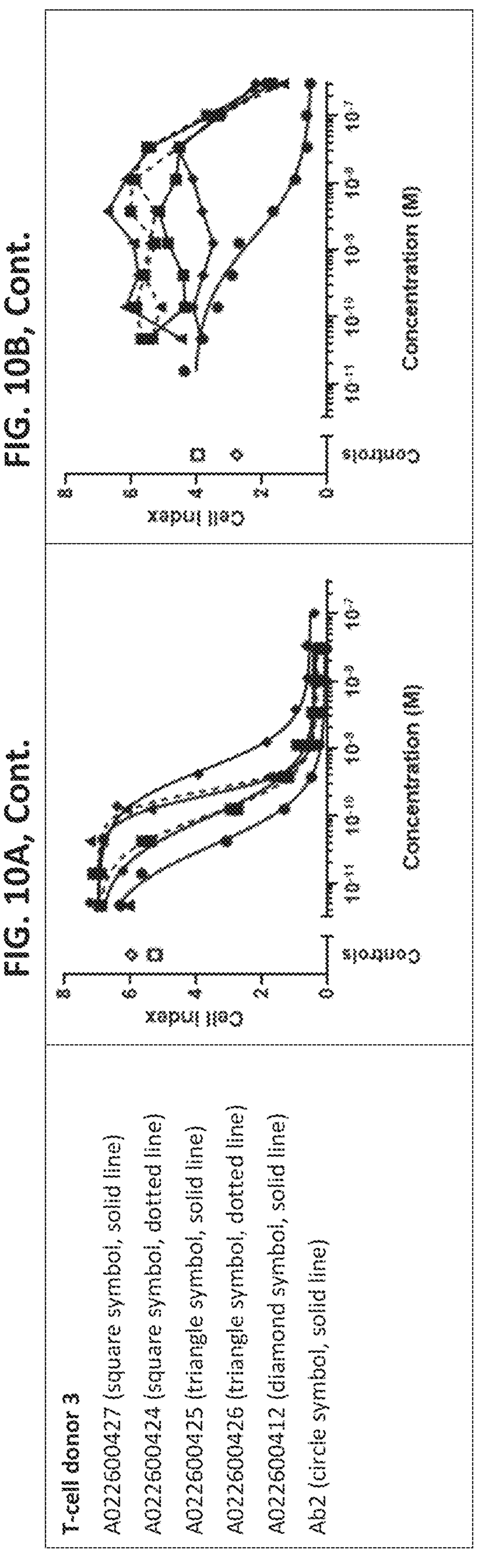
FIG. 10A, Cont.
FIG. 10B, Cont.

Tetravalent formats
Normalized binding level at 125 seconds (RU)
700
600
500
400
300
200
100
0
20 RU
A02260424
A02260425
A02260426
A02260427
F02730109
Normalized binding level at 125 seconds (RU)
200
150
100
50
0
20 RU
A02260424
A02260425
A02260426
A02260427
F02730109

Trivalent formats
Normalized binding level at 125 seconds (RU)
700
600
500
400
300
200
100
0
A022600412
IRR00096
Normalized binding level at 125 seconds (RU)
200
150
100
50
0
20 RU
A022600412
IRR00096

FIG. 12

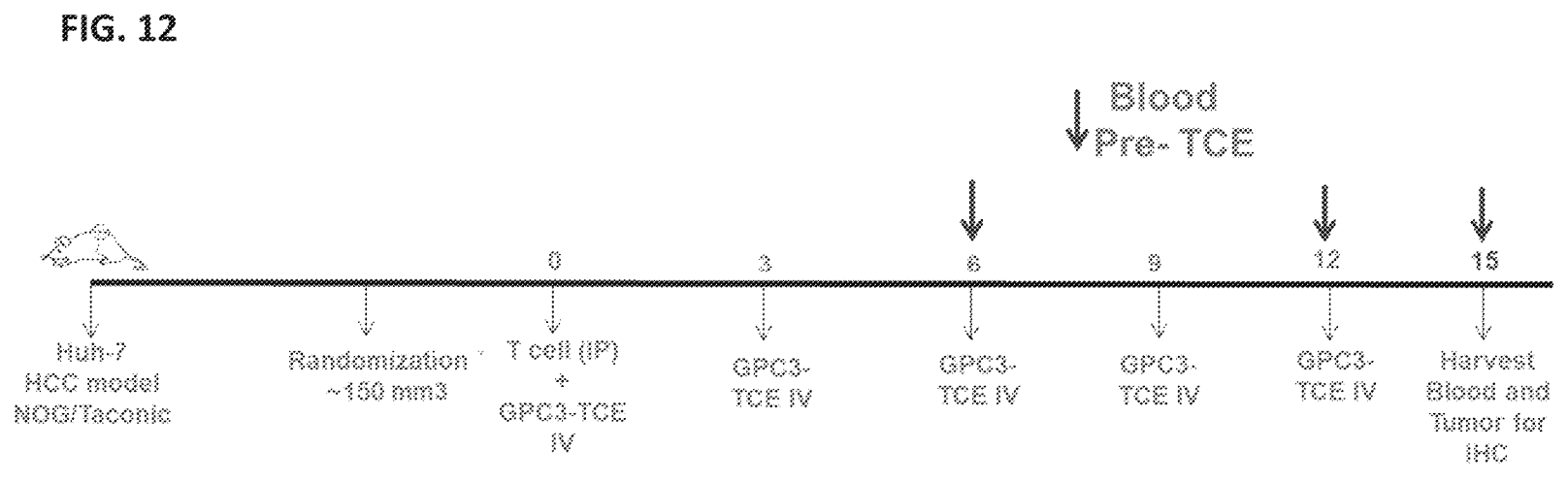

Blood
Pre- TCE
0
3
6
9
12
15
Huh-7
HCC model
NOG/Taconic
Randomization
~150 mm3
T cell (IP)
+
GPC3-TCE
IV
GPC3-
TCE IV
GPC3-
TCE IV
GPC3-
TCE IV
GPC3-
TCE IV
Harvest
Blood and
Tumor for
IHC

POLYPEPTIDES COMPRISING IMMUNOGLOBULIN SINGLE VARIABLE DOMAINS TARGETING GLYPICAN-3 AND T CELL RECEPTOR

RELATED APPLICATION

This application claims priority to U.S. patent application Ser. No. 17/553,908, filed Dec. 17, 2021, which claims the benefit under 35 U.S.C. § 119(e) of U.S. Provisional Application Ser. No. 63/127,224, filed Dec. 18, 2020, the entire contents of each of which are incorporated by reference herein in their entireties.

REFERENCE TO AN ELECTRONIC SEQUENCE LISTING

The contents of the electronic sequence listing (A084870220US02-SEQ-CRP.xml; Size: 247,396 bytes; and Date of Creation: Jan. 10, 2024) is herein incorporated by reference in its entirety.

1 FIELD OF THE INVENTION

The present technology relates to polypeptides targeting Glypican-3 (GPC3) and T cell receptor (TCR). It also relates to nucleic acid molecules encoding the polypeptide and vectors comprising the nucleic acids, and to compositions comprising the polypeptide, nucleic acid or vector. The technology further relates to these products for use in a method of treating a subject suffering from a disease involving abnormal cells, such as cancerous or infected cells. Moreover, the technology relates to methods of producing these products.

2 TECHNOLOGICAL BACKGROUND

Cytotoxic T cells (CTL) are T lymphocytes that kill cancer cells, cells that are infected (particularly with viruses), or cells that are damaged in other ways. T lymphocytes (also called T cells) express the T cell receptor (TCR) and the CD3 receptor on the cell surface. The αβ TCR-CD3 complex (or "TCR complex") is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are tyrosine phosphorylated upon receptor activation and recruit a large number of signalling components (Call et al. 2004, Molecular Immunology 40: 1295-1305).

Both α and β chains of the heterodimeric T cell receptor (TCR) consist of a constant domain and a variable domain. T cells are activated upon TCR recognition of cognate peptide presented by self-MHC molecules, with signal transduction initiated by tyrosine phosphorylated CD3 complexes, leading to T cell proliferation and differentiation.

Bispecific antibodies have been engineered that have a tumour recognition part on the one arm (target-binding arm) whereas the other arm of the molecule has specificity for a T cell antigen (effector-binding arm), often CD3. These bispecific antibodies, so called T-cell engagers (TCE), are multitargeting molecules that enhance the patient's immune response to malignant cells. Co-engagement of T-cell and tumour cell by the multispecific antibody leads to the formation of a cytolytic synapse between the T cell and the tumour cell, that induces T-cell activation and results in tumour cell killing.

While the majority of T cell activating bispecific antibodies target the CD3 complex on the T cell, some bispecific binders that target the constant domain of the αβ T cell receptor have been described in WO 2016/180969 A1.

Glypican-3 (GPC3) is a GPI anchored cell surface glycoprotein consisting of heparan sulfate GAG chains and a core protein. It has been implicated in embryogenesis and early development, controlling cell growth and differentiation. Whereas the expression of GPC3 is high during development, its expression is nearly absent in normal adult tissue, with moderate/low expression in renal proximal tubules and bronchial cells. Consistent with its role in early development, high level of GPC3 is also expressed in placenta.

GPC3 likely regulates early development via multiple signalling cascades, including the Wnt, Hh and YAP pathways. In addition, GPC3 is able to interact with basic growth factors, such as FGF2 to regulate cell growth. In an experimental setting, overexpression of GPC3 can inhibit FGF2-induced cell proliferation. By contrast, GPC3 also negatively regulates BMP7, an inhibitory growth factor. Altogether, the activity of GPC3 can be highly contextual, as it is able to not only inhibit cell proliferation, but also can promote carcinogenesis in liver and other forms of cancer.

GPC3 expression is especially prevalent in tumour tissue from hepatocellular carcinoma (HCC), a disease with significant unmet needs. Soluble GPC3 can also be detected in serum of HCC patients and has been used to differentiate from liver diseases with different aetiologies.

Bispecific antibody constructs have been proposed in multiple formats. For example, bispecific antibody formats may involve the chemical conjugation of two antibodies or fragments thereof (Brennan, M, et al., Science, 1985. 229 (4708): p. 81-83; Glennie, M. J., et al., J Immunol, 1987. 139(7): p. 2367-2375).

Disadvantages of such bispecific antibody formats include, however, high molecular weight and high viscosity at high concentration, making e.g. subcutaneous administration challenging, and in that each binding unit requires the interaction of two variable domains for specific and high affinity binding, having implications on polypeptide stability and efficiency of production. Such bispecific antibody formats may also potentially lead to CMC issues related to poor production efficiency and low titers and/or mispairing of the light chains or mispairing of the heavy chains.

Therefore, there is a need for antibody constructs that bind both to a target cell and a T cell with sufficient affinity to induce a cytotoxic response. At the same time, such constructs should not induce a cytotoxic response to non-target cells, i.e. cells that do not express the target antigen or only express it at low levels. Thereby, a balance can be struck between efficacy and safety. It is further desirable that such constructs can be efficiently produced, e.g. in microbial hosts. Such constructs should ideally also exhibit a half-life in the subject to be treated that is long enough such that consecutive treatments can be conveniently spaced apart. Furthermore, it is desirable to limit the reactivity of such constructs to pre-existing antibodies in the subject to be treated (i.e. antibodies present in the subject before the first treatment with the antibody construct). Moreover, the polypeptides should exert no or only minimal undesired side effects, e.g. provoked by cytotoxic activity on non-target cells.

3 SUMMARY OF THE INVENTION

The present inventors found that a polypeptide targeting specifically GPC3 and TCR at the same time leads to efficient T cell-mediated killing of GPC3 expressing cells in vitro. Said polypeptides could be efficiently produced (e.g. in microbial hosts). Furthermore, such polypeptides could be shown to exhibit limited reactivity to pre-existing antibodies in the subject to be treated (i.e., antibodies present in the subject before the first treatment with the antibody construct). In preferred embodiments such polypeptides exhibit a half-life in the subject to be treated that is long enough such that consecutive treatments can be conveniently spaced apart. Moreover, such polypeptides showed only limited activity against cells expressing no or low levels of GPC3. This suggests the possibility of inducing a highly specific T cell-mediated cytotoxic response against GPC3 positive cancer target cells, while exhibiting a favourable safety profile.

In one aspect, the polypeptide comprises or consists of at least three immunoglobulin single variable domains (ISVDs), wherein at least two ISVDs specifically bind to GPC3 and one ISVD specifically binds to the constant domain of a TCR on a T cell. Preferably, the at least two ISVDs specifically binding to GPC3 specifically bind to human GPC3 and the ISVD specifically binding to TCR specifically binds to human TCR. More preferably, the at least two ISVDs specifically binding to GPC3 are distinct ISVDs. In another aspect, the polypeptide comprising or consisting of at least three ISVDs preferably further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a serum protein, preferably to a human serum protein such as human serum albumin.

In one aspect the present technology provides a polypeptide comprising or consisting of at least one immunoglobulin single variable domain (ISVD) that specifically binds to GPC3. In a further embodiment, the polypeptide of the present technology comprises or consists of at least two ISVDs that specifically bind to GPC3, wherein the two ISVDs are optionally linked via a peptidic linker. Preferably, the two ISVDs specifically binding to GPC3 are distinct ISVDs. Moreover, the polypeptide preferably further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a serum protein, preferably to a human serum protein such as human serum albumin.

In another aspect, the polypeptide of the present technology comprises or consists of an ISVD that specifically binds to constant domain of a TCR on a T cell and at least one ISVD that specifically binds to GPC3, wherein the two ISVDs are optionally linked via a peptidic linker. Such a polypeptide can be used to redirect T cells for killing of cells expressing GPC3. Ideally, the ISVD binding to TCR is the only binding moiety comprised in said polypeptide that specifically binds to a, e.g. human, T cell. Moreover, the examples show that when the ISVD that specifically binds to TCR is located at the N-terminus of such a polypeptide, better T-cell mediated cytotoxicity is achieved compared to when the same anti-TCR ISVD not located at the N-terminus. The ISVD that specifically binds to TCR is thus preferably located N-terminally from the at least one ISVD that specifically binds to GPC3. Most preferably, the ISVD that specifically binds to TCR is located at the N-terminus of a polypeptide comprising the same. Moreover, the polypeptide preferably further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a serum protein, preferably to a human serum protein such as human serum albumin.

Also provided is a nucleic acid molecule capable of expressing the polypeptide, a nucleic acid or vector comprising the nucleic acid, and a composition comprising the polypeptide, the nucleic acid or the vector. The composition is preferably a pharmaceutical composition.

Also provided is a host cell or (non-human) host comprising the nucleic acid or vector that encodes the polypeptide as disclosed herein.

Further provided is a method for producing the polypeptide as disclosed herein, said method at least comprising the steps of:

a. expressing, in a suitable host cell or host organism or in another suitable expression system, a nucleic acid sequence encoding the polypeptide; optionally followed by:
b. isolating and/or purifying the polypeptide.

Moreover, the present technology provides the polypeptide, the composition comprising the polypeptide, or the composition comprising the nucleic acid or vector comprising the nucleotide sequence that encodes the polypeptide, for use as a medicament. Preferably, the polypeptide or composition is for use in the treatment of cancer, such as liver cancer or lung cancer.

In addition, provided is a method of treating cancer, wherein said method comprises administering, to a subject in need thereof, a pharmaceutically active amount of the polypeptide or a composition according to the present disclosure. The cancer is preferably selected from liver cancer or lung cancer. In some embodiments, the method further comprises administering one or more additional therapeutic agents.

Further provided is the use of the polypeptide or composition in the preparation of a pharmaceutical composition for treating cancer, preferably liver cancer or lung cancer.

In particular, the present technology provides the following embodiments:

Embodiment 1. A polypeptide that comprises or consists of at least three immunoglobulin single variable domains (ISVDs), wherein each of said ISVDs comprises three complementarity determining regions (CDR1 to CDR3, respectively), wherein the at least three ISVDs are optionally linked via one or more peptidic linkers, and wherein:

a) a first ISVD comprises
  i. a CDR1 that is the amino acid sequence of SEQ ID NO: 6 or an amino acid sequence with 2 or 1 amino acid difference(s) with SEQ ID NO: 6;

ii. a CDR2 that is the amino acid sequence of SEQ ID NO: 10 or an amino acid sequence with 2 or 1 amino acid difference(s) with SEQ ID NO: 10; and iii. a CDR3 that is the amino acid sequence of SEQ ID NO: 14 or an amino acid sequence with 2 or 1 amino acid difference(s) with SEQ ID NO: 14;

b) a second ISVD comprises iv. a CDR1 that is the amino acid sequence of SEQ ID NO: 7 or an amino acid sequence with 2 or 1 amino acid difference(s) with SEQ ID NO: 7;

v. a CDR2 that is the amino acid sequence of SEQ ID NO: 11 or an amino acid sequence with 2 or 1 amino acid difference(s) with SEQ ID NO: 11; and vi. a CDR3 that is the amino acid sequence of SEQ ID NO: 15 or an amino acid sequence with 2 or 1 amino acid difference(s) with SEQ ID NO: 15; and c) a third ISVD comprises vii. a CDR1 that is the amino acid sequence of SEQ ID NO: 8 or an amino acid sequence with 2 or 1 amino acid difference(s) with SEQ ID NO: 8;

viii. a CDR2 that is the amino acid sequence of SEQ ID NO: 12 or an amino acid sequence with 2 or 1 amino acid difference(s) with SEQ ID NO: 12; and ix. a CDR3 that is the amino acid sequence of GVA or an amino acid sequence with 2 or 1 amino acid difference(s) with GVA, wherein the order of the ISVDs indicates their relative position to each other considered from the N-terminus to the C-terminus of said polypeptide, wherein the first ISVDs is optionally located at the N-terminus of said polypeptide.

Embodiment 2. The polypeptide according to embodiment 1, wherein:

a) said first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14;

b) said second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15; and c) said third ISVD comprises a CDR1 being the amino acid sequence of SEQ ID NO: 8, a CDR2 being the amino acid sequence of SEQ ID NO: 12 and a CDR3 being the amino acid sequence of GVA.

Embodiment 3. The polypeptide according to any of embodiments 1 or 2, wherein:

a) the amino acid sequence of said first ISVD exhibits a sequence identity of more than 90% with SEQ ID NO: 2;

b) the amino acid sequence of said second ISVD exhibits a sequence identity of more than 90% with SEQ ID NO: 3; and c) the amino acid sequence of said third ISVD exhibits a sequence identity of more than 90% identity with SEQ ID NO: 4.

Embodiment 4. The polypeptide according to any of embodiments 1 to 3, wherein:

a) said first ISVD consists of the amino acid sequence of SEQ ID NO: 2;

b) said second ISVD consists of the amino acid sequence of SEQ ID NO: 3; and c) said third ISVD consists of the amino acid sequence of SEQ ID NO: 4.

Embodiment 5. The polypeptide according to any of embodiments 1 to 4, wherein the first ISVD and the second ISVD are linked to each other via a linker consisting of less than 10 amino acids, preferably less than 6 amino acids, wherein the linker most preferably is a 5GS linker.

Embodiment 6. The polypeptide according to any of embodiments 1 to 5, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 7. The polypeptide according to embodiment 6, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 8. The polypeptide according to any one of embodiments 6 or 7, in which said one or more other binding units that provide the polypeptide with increased half-life is chosen from the group consisting of binding units that can bind to serum albumin (such as human serum albumin) or a serum immunoglobulin (such as IgG).

Embodiment 9. The polypeptide according to embodiment 8, in which said binding unit that provides the polypeptide with increased half-life is an ISVD that binds to human serum albumin.

Embodiment 10. The polypeptide according to embodiment 9, wherein the ISVD binding to human serum albumin comprises i. a CDR1 that is the amino acid sequence of SEQ ID NO: 9 or an amino acid sequence with 2 or 1 amino acid difference(s) with SEQ ID NO: 9;

ii. a CDR2 that is the amino acid sequence of SEQ ID NO: 13 or an amino acid sequence with 2 or 1 amino acid difference(s) with SEQ ID NO: 13; and iii. a CDR3 that is the amino acid sequence of SEQ ID NO: 17 or an amino acid sequence with 2 or 1 amino acid difference(s) with SEQ ID NO: 17.

Embodiment 11. The polypeptide according to any of embodiments 9 or 10, wherein the ISVD binding to human serum albumin comprises a CDR1 being the amino acid sequence of SEQ ID NO: 9, a CDR2 being the amino acid sequence of SEQ ID NO: 13 and a CDR3 being the amino acid sequence of SEQ ID NO: 17.

Embodiment 12. The polypeptide according to any of embodiments 9 to 11, wherein the amino acid sequence of said ISVD binding to human serum albumin exhibits a sequence identity of more than 90% with SEQ ID NO: 5.

Embodiment 13. The polypeptide according to any of embodiments 9 to 12, wherein said ISVD binding to human serum albumin consists of the amino acid sequence of SEQ ID NO: 5.

Embodiment 14. The polypeptide according to any of embodiments 1 to 13, wherein the polypeptide comprises or consists of an amino acid sequence exhibiting a sequence identity of more than 90% with SEQ ID NO: 1.

Embodiment 15. The polypeptide according to any of embodiments 1 to 14, wherein the polypeptide comprises or consists of the amino acid sequence of SEQ ID NO: 1.

Embodiment 16. A polypeptide that comprises or consists of at least one immunoglobulin single variable domain (ISVD), wherein said ISVD comprises three complementarity determining regions (CDR1 to CDR3, respectively), and wherein the at least one ISVD comprises:

a) a CDR1 that is the amino acid sequence of SEQ ID NO: 7 or an amino acid sequence with 2 or 1 amino acid difference(s) with SEQ ID NO: 7;
   a CDR2 that is the amino acid sequence of SEQ ID NO: 11 or an amino acid sequence with 2 or 1 amino acid difference(s) with SEQ ID NO: 11; and
   a CDR3 that is the amino acid sequence of SEQ ID NO: 15 or an amino acid sequence with 2 or 1 amino acid difference(s) with SEQ ID NO: 15, or
b) a CDR1 that is the amino acid sequence of SEQ ID NO: 8 or an amino acid sequence with 2 or 1 amino acid difference(s) with SEQ ID NO: 8;
   a CDR2 that is the amino acid sequence of SEQ ID NO: 12 or an amino acid sequence with 2 or 1 amino acid difference(s) with SEQ ID NO: 12; and
   a CDR3 that is the amino acid sequence of GVA or an amino acid sequence with 2 or 1 amino acid difference(s) with GVA.

Embodiment 17. The polypeptide according to embodiment 16, wherein the at least one ISVD comprises:

a) a CDR1 being the amino acid sequence of SEQ ID NO: 7, a CDR2 being the amino acid sequence of SEQ ID NO: 11 and a CDR3 being the amino acid sequence of SEQ ID NO: 15, or
b) a CDR1 being the amino acid sequence of SEQ ID NO: 8, a CDR2 being the amino acid sequence of SEQ ID NO: 12 and a CDR3 being the amino acid sequence of GVA.

Embodiment 18. The polypeptide according to any of embodiments 16 or 17, wherein the amino acid sequence of the at least one ISVD comprises:

a) a sequence identity of more than 90% with SEQ ID NO: 3, or
b) a sequence identity of more than 90% identity with SEQ ID NO: 4.

Embodiment 19. The polypeptide according to any of embodiments 16 to 18, wherein said at least one ISVD comprises or consists of:

a) the amino acid sequence of SEQ ID NO: 3, or
b) the amino acid sequence of SEQ ID NO: 4.

Embodiment 20. A polypeptide that comprises or consists of at least two ISVDs, wherein each of said ISVDs comprises three complementarity determining regions (CDR1 to CDR3, respectively), wherein the at least two ISVDs are optionally linked via one or more peptidic linkers, and wherein:

a) a first and a second ISVD comprise
   i. a CDR1 that is the amino acid sequence of SEQ ID NO: 7 or an amino acid sequence with 2 or 1 amino acid difference(s) with SEQ ID NO: 7;
   ii. a CDR2 that is the amino acid sequence of SEQ ID NO: 11 or an amino acid sequence with 2 or 1 amino acid difference(s) with SEQ ID NO: 11; and
   iii. a CDR3 that is the amino acid sequence of SEQ ID NO: 15 or an amino acid sequence with 2 or 1 amino acid difference(s) with SEQ ID NO: 15,
b) a first and a second ISVD comprise
   i. a CDR1 that is the amino acid sequence of SEQ ID NO: 8 or an amino acid sequence with 2 or 1 amino acid difference(s) with SEQ ID NO: 8;
   ii. a CDR2 that is the amino acid sequence of SEQ ID NO: 12 or an amino acid sequence with 2 or 1 amino acid difference(s) with SEQ ID NO: 12; and
   iii. a CDR3 that is the amino acid sequence of GVA or an amino acid sequence with 2 or 1 amino acid difference(s) with GVA,
c) a first ISVD comprises
   i. a CDR1 that is the amino acid sequence of SEQ ID NO: 7 or an amino acid sequence with 2 or 1 amino acid difference(s) with SEQ ID NO: 7;
   ii. a CDR2 that is the amino acid sequence of SEQ ID NO: 11 or an amino acid sequence with 2 or 1 amino acid difference(s) with SEQ ID NO: 11; and
   iii. a CDR3 that is the amino acid sequence of SEQ ID NO: 15 or an amino acid sequence with 2 or 1 amino acid difference(s) with SEQ ID NO: 15, and
   a second ISVD comprises
   iv. a CDR1 that is the amino acid sequence of SEQ ID NO: 8 or an amino acid sequence with 2 or 1 amino acid difference(s) with SEQ ID NO: 8;
   v. a CDR2 that is the amino acid sequence of SEQ ID NO: 12 or an amino acid sequence with 2 or 1 amino acid difference(s) with SEQ ID NO: 12; and
   vi. a CDR3 that is the amino acid sequence of GVA or an amino acid sequence with 2 or 1 amino acid difference(s) with GVA,
d) a first ISVD comprises
   i. a CDR1 that is the amino acid sequence of SEQ ID NO: 8 or an amino acid sequence with 2 or 1 amino acid difference(s) with SEQ ID NO: 8;
   ii. a CDR2 that is the amino acid sequence of SEQ ID NO: 12 or an amino acid sequence with 2 or 1 amino acid difference(s) with SEQ ID NO: 12; and
   iii. a CDR3 that is the amino acid sequence of GVA or an amino acid sequence with 2 or 1 amino acid difference(s) with GVA, and
   a second ISVD comprises
   iv. a CDR1 that is the amino acid sequence of SEQ ID NO: 7 or an amino acid sequence with 2 or 1 amino acid difference(s) with SEQ ID NO: 7;
   v. a CDR2 that is the amino acid sequence of SEQ ID NO: 11 or an amino acid sequence with 2 or 1 amino acid difference(s) with SEQ ID NO: 11; and
   vi. a CDR3 that is the amino acid sequence of SEQ ID NO: 15 or an amino acid sequence with 2 or 1 amino acid difference(s) with SEQ ID NO: 15,
e) a first ISVD comprises
   i. a CDR1 that is the amino acid sequence of SEQ ID NO: 6 or an amino acid sequence with 2 or 1 amino acid difference(s) with SEQ ID NO: 6;
   ii. a CDR2 that is the amino acid sequence of SEQ ID NO: 10 or an amino acid sequence with 2 or 1 amino acid difference(s) with SEQ ID NO: 10; and
   iii. a CDR3 that is the amino acid sequence of SEQ ID NO: 14 or an amino acid sequence with 2 or 1 amino acid difference(s) with SEQ ID NO: 14, and
   a second ISVD comprises
   iv. a CDR1 that is the amino acid sequence of SEQ ID NO: 7 or an amino acid sequence with 2 or 1 amino acid difference(s) with SEQ ID NO: 7;
   v. a CDR2 that is the amino acid sequence of SEQ ID NO: 11 or an amino acid sequence with 2 or 1 amino acid difference(s) with SEQ ID NO: 11; and vi. a CDR3 that is the amino acid sequence of SEQ ID NO: 15 or an amino acid sequence with 2 or 1 amino acid difference(s) with SEQ ID NO: 15, f) a first ISVD comprises i. a CDR1 that is the amino acid sequence of SEQ ID NO: 7 or an amino acid sequence with 2 or 1 amino acid difference(s) with SEQ ID NO: 7;

ii. a CDR2 that is the amino acid sequence of SEQ ID NO: 11 or an amino acid sequence with 2 or 1 amino acid difference(s) with SEQ ID NO: 11; and iii. a CDR3 that is the amino acid sequence of SEQ ID NO: 15 or an amino acid sequence with 2 or 1 amino acid difference(s) with SEQ ID NO: 15, and a second ISVD comprises iv. a CDR1 that is the amino acid sequence of SEQ ID NO: 6 or an amino acid sequence with 2 or 1 amino acid difference(s) with SEQ ID NO: 6;

v. a CDR2 that is the amino acid sequence of SEQ ID NO: 10 or an amino acid sequence with 2 or 1 amino acid difference(s) with SEQ ID NO: 10; and vi. a CDR3 that is the amino acid sequence of SEQ ID NO: 14 or an amino acid sequence with 2 or 1 amino acid difference(s) with SEQ ID NO: 14, g) a first ISVD comprises i. a CDR1 that is the amino acid sequence of SEQ ID NO: 6 or an amino acid sequence with 2 or 1 amino acid difference(s) with SEQ ID NO: 6;

ii. a CDR2 that is the amino acid sequence of SEQ ID NO: 10 or an amino acid sequence with 2 or 1 amino acid difference(s) with SEQ ID NO: 10; and iii. a CDR3 that is the amino acid sequence of SEQ ID NO: 14 or an amino acid sequence with 2 or 1 amino acid difference(s) with SEQ ID NO: 14, and a second ISVD comprises iv. a CDR1 that is the amino acid sequence of SEQ ID NO: 8 or an amino acid sequence with 2 or 1 amino acid difference(s) with SEQ ID NO: 8;

v. a CDR2 that is the amino acid sequence of SEQ ID NO: 12 or an amino acid sequence with 2 or 1 amino acid difference(s) with SEQ ID NO: 12; and vi. a CDR3 that is the amino acid sequence of GVA or an amino acid sequence with 2 or 1 amino acid difference(s) with GVA, or h) a first ISVD comprises i. a CDR1 that is the amino acid sequence of SEQ ID NO: 8 or an amino acid sequence with 2 or 1 amino acid difference(s) with SEQ ID NO: 8;

ii. a CDR2 that is the amino acid sequence of SEQ ID NO: 12 or an amino acid sequence with 2 or 1 amino acid difference(s) with SEQ ID NO: 12; and iii. a CDR3 that is the amino acid sequence of GVA or an amino acid sequence with 2 or 1 amino acid difference(s) with GVA, and a second ISVD comprises iv. a CDR1 that is the amino acid sequence of SEQ ID NO: 6 or an amino acid sequence with 2 or 1 amino acid difference(s) with SEQ ID NO: 6;

v. a CDR2 that is the amino acid sequence of SEQ ID NO: 10 or an amino acid sequence with 2 or 1 amino acid difference(s) with SEQ ID NO: 10; and vi. a CDR3 that is the amino acid sequence of SEQ ID NO: 14 or an amino acid sequence with 2 or 1 amino acid difference(s) with SEQ ID NO: 14, wherein the order of the ISVDs indicates their relative position to each other considered from the N-terminus to the C-terminus of said polypeptide.

Embodiment 21. The polypeptide according to embodiment 20, wherein:

a) the first and the second ISVD comprise a CDR1 being the amino acid sequence of SEQ ID NO: 7, a CDR2 being the amino acid sequence of SEQ ID NO: 11 and a CDR3 being the amino acid sequence of SEQ ID NO: 15, b) the first and the second ISVD comprise a CDR1 being the amino acid sequence of SEQ ID NO: 8, a CDR2 being the amino acid sequence of SEQ ID NO: 12 and a CDR3 being the amino acid sequence of GVA, c) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 8, a CDR2 being the amino acid sequence of SEQ ID NO: 12 and a CDR3 being the amino acid sequence of GVA, d) the first ISVD comprises a CDR1 being the amino acid sequence of SEQ ID NO: 8, a CDR2 being the amino acid sequence of SEQ ID NO: 12 and a CDR3 being the amino acid sequence of GVA, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, e) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, f) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, g) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 8, a CDR2 being the amino acid sequence of SEQ ID NO: 12 and a CDR3 being the amino acid sequence of GVA, or h) the first ISVD comprises a CDR1 being the amino acid sequence of SEQ ID NO: 8, a CDR2 being the amino acid sequence of SEQ ID NO: 12 and a CDR3 being the amino acid sequence of GVA, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14.

Embodiment 22. The polypeptide according to any of embodiments 20 or 21, wherein:

a) the amino acid sequence of the first and the second ISVD exhibits a sequence identity of more than 90% with SEQ ID NO: 3,
b) the amino acid sequence of the first and the second ISVD exhibits a sequence identity of more than 90% with SEQ ID NO: 4,
c) the amino acid sequence of the first ISVD exhibits a sequence identity of more than 90% with SEQ ID NO: 3, and the second ISVD exhibits a sequence identity of more than 90% identity with SEQ ID NO: 4,
d) the amino acid sequence of the first ISVD exhibits a sequence identity of more than 90% with SEQ ID NO: 4, and the second ISVD exhibits a sequence identity of more than 90% identity with SEQ ID NO: 3,
e) the amino acid sequence of the first ISVD exhibits a sequence identity of more than 90% with SEQ ID NO: 2, and the second ISVD exhibits a sequence identity of more than 90% identity with SEQ ID NO: 3,
f) the amino acid sequence of the first ISVD exhibits a sequence identity of more than 90% with SEQ ID NO: 3, and the second ISVD exhibits a sequence identity of more than 90% identity with SEQ ID NO: 2
g) the amino acid sequence of the first ISVD exhibits a sequence identity of more than 90% with SEQ ID NO: 2, and the second ISVD exhibits a sequence identity of more than 90% identity with SEQ ID NO: 4, or
h) the amino acid sequence of the first ISVD exhibits a sequence identity of more than 90% with SEQ ID NO: 4, and the second ISVD exhibits a sequence identity of more than 90% identity with SEQ ID NO: 2.

Embodiment 23. The polypeptide according to any of embodiments 20 to 22, wherein:
a) the first and the second ISVD consist of the amino acid sequence of SEQ ID NO: 3,
b) the first and the second ISVD consist of the amino acid sequence of SEQ ID NO: 4,
c) the first ISVD consists of the amino acid sequence of SEQ ID NO: 3, and the second ISVD consists of the amino acid sequence of SEQ ID NO: 4,
d) the first ISVD consists of the amino acid sequence of SEQ ID NO: 4, and the second ISVD consists of the amino acid sequence of SEQ ID NO: 3,
e) the first ISVD consists of the amino acid sequence of SEQ ID NO: 2, and the second ISVD consists of the amino acid sequence of SEQ ID NO: 3,
f) the first ISVD consists of the amino acid sequence of SEQ ID NO: 3, and the second ISVD consists of the amino acid sequence of SEQ ID NO: 2,
g) the first ISVD consists of the amino acid sequence of SEQ ID NO: 2, and the second ISVD consists of the amino acid sequence of SEQ ID NO: 4, or
h) the first ISVD consists of the amino acid sequence of SEQ ID NO: 4, and the second ISVD consists of the amino acid sequence of SEQ ID NO: 2.

Embodiment 24. The polypeptide according to any of embodiments 20 to 23, wherein the polypeptide comprises or consists of an amino acid sequence selected from SEQ ID NOs: 1, 49-72 and 78-81.

Embodiment 25. The polypeptide according to any of embodiments 16 to 24, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 26. The polypeptide according to embodiment 25, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 27. The polypeptide according to any one of embodiments 25 to 26, in which said one or more other binding units that provide the polypeptide with increased half-life is chosen from the group consisting of binding units that can bind to serum albumin (such as human serum albumin) or a serum immunoglobulin (such as IgG).

Embodiment 28. The polypeptide according to embodiment 27, in which said binding unit that provides the polypeptide with increased half-life is an ISVD that binds to human serum albumin.

Embodiment 29. The polypeptide according to embodiment 28, wherein the ISVD binding to human serum albumin comprises
i. a CDR1 that is the amino acid sequence of SEQ ID NO: 9 or an amino acid sequence with 2 or 1 amino acid difference(s) with SEQ ID NO: 9;
ii. a CDR2 that is the amino acid sequence of SEQ ID NO: 13 or an amino acid sequence with 2 or 1 amino acid difference(s) with SEQ ID NO: 13; and
iii. a CDR3 that is the amino acid sequence of SEQ ID NO: 17 or an amino acid sequence with 2 or 1 amino acid difference(s) with SEQ ID NO: 17.

Embodiment 30. The polypeptide according to any of embodiments 28 to 29, wherein the ISVD binding to human serum albumin comprises a CDR1 being is the amino acid sequence of SEQ ID NO: 9, a CDR2 being the amino acid sequence of SEQ ID NO: 13 and a CDR3 being the amino acid sequence of SEQ ID NO: 17.

Embodiment 31. The polypeptide according to any of embodiments 28 to 30, wherein the amino acid sequence of said ISVD binding to human serum albumin exhibits a sequence identity of more than 90% with SEQ ID NO: 5.

Embodiment 32. The polypeptide according to any of embodiments 28 to 31, wherein said ISVD binding to human serum albumin consists of the amino acid sequence of SEQ ID NO: 5.

Embodiment 33. A nucleic acid comprising a nucleotide sequence that encodes a polypeptide according to any of embodiments 1 to 32, preferably according to any of embodiments 1 to 15.

Embodiment 34. A host or host cell comprising a nucleic acid according to embodiment 33.

Embodiment 35. A method for producing a polypeptide according to any of embodiments 1 to 32, preferably according to any of embodiments 1 to 15, said method at least comprising the steps of:
a) expressing, in a suitable host cell or host organism or in another suitable expression system, a nucleic acid according to embodiment 33; optionally followed by:

b) isolating and/or purifying the polypeptide according to any of embodiments 1 to 32, preferably according to any of embodiments 1 to 15.

Embodiment 36. A composition comprising at least one polypeptide according to any of embodiments 1 to 32, preferably according to any of embodiments 1 to 15, or a nucleic acid according to embodiment 33.

Embodiment 37. The composition according to embodiment 36, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 38. A polypeptide according to any of embodiments 1 to 32, preferably according to any of embodiments 1 to 15, or a composition according to embodiment 36 or 37, for use as a medicament.

Embodiment 39. A polypeptide according to any of embodiments 1 to 32, preferably according to any of embodiments 1 to 15, or a composition according to embodiment 36 or 37, for use in the treatment of cancer, preferably liver cancer or lung cancer.

Embodiment 40. The polypeptide or composition for use according to embodiment 39, wherein the liver cancer is hepatocellular carcinoma (HCC).

Embodiment 41. The polypeptide or composition for use according to embodiment 39, wherein the lung cancer is non-small cell lung cancer (NSCLC), preferably squamous cell carcinoma (SCC).

Embodiment 42. A method of treating cancer, preferably liver cancer or lung cancer, wherein said method comprises administering, to a subject in need thereof, a pharmaceutically active amount of a polypeptide according to any of embodiments 1 to 32, preferably according to any of embodiments 1 to 15, or a composition according to embodiment 36 or 37.

Embodiment 43. The method according to embodiment 42, wherein the liver cancer is hepatocellular carcinoma.

Embodiment 44. The method according to embodiment 42, wherein the lung cancer is non-small cell lung cancer (NSCLC), preferably squamous cell carcinoma (SCC).

Embodiment 45. Use of a polypeptide according to any of embodiments 1 to 32, preferably according to any of embodiments 1 to 15, or a composition according to embodiment 36 or 37, in the preparation of a medicament.

Embodiment 46. Use of a polypeptide according to any of embodiments 1 to 32, preferably according to embodiments 1 to 15, or a composition according to embodiment 36 or 37, in the preparation of a pharmaceutical composition for treating cancer, preferably liver cancer or lung cancer.

Embodiment 47. Use of the polypeptide or a composition according to embodiment 46, wherein the liver cancer is hepatocellular carcinoma.

Embodiment 48. Use of the polypeptide or the composition according to embodiment 46, wherein the lung cancer is non-small cell lung cancer (NSCLC), preferably squamous cell carcinoma (SCC).

4 BRIEF DESCRIPTION OF THE DRAWINGS

Figure 1B:
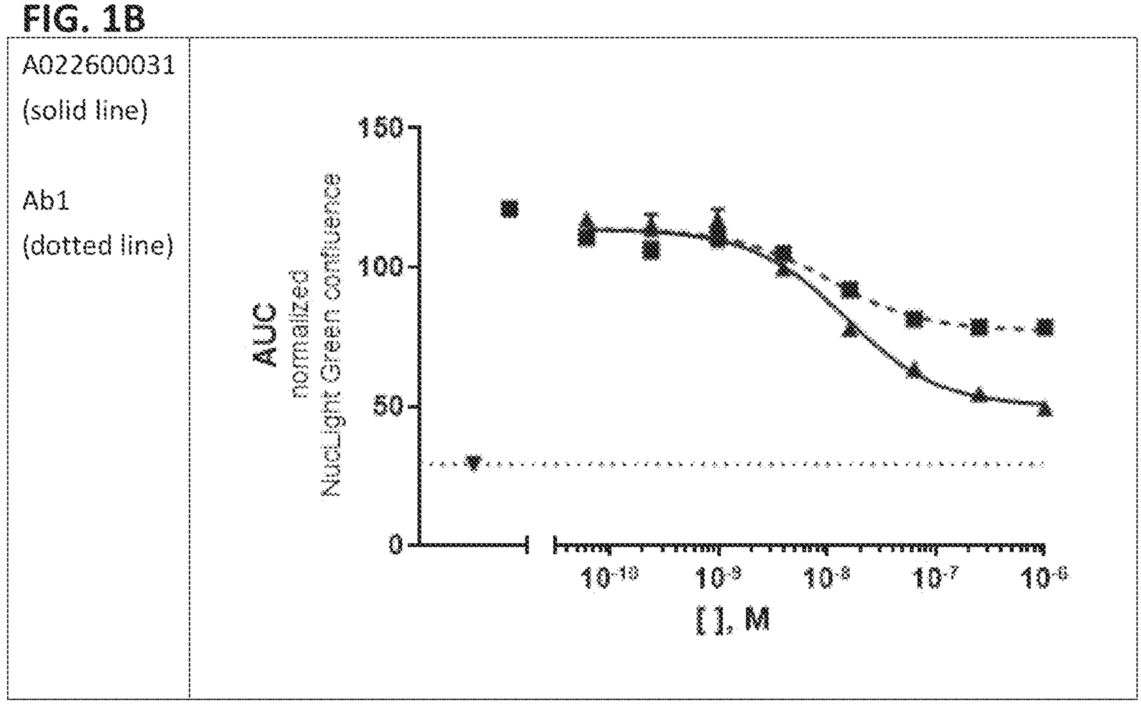

FIGS. 1A-1B: Dose-dependent killing of the trispecific GPC3 T-cell engagers A022600027 (FIG. 1A), A022600031 (FIG. 1B solid line) and a construct with the reference Ab1 (FIG. 1B dotted line) in the Incucyte based human TDC (T-cell dependent cytotoxicity) HepG2-Nuclight green assay using an effector to target ratio of 15:1, analyzed at 60 h after seeding. Controls (left) are: (solid square) No compound and (solid triangle) Brefeldin A 1 μM for 100% killing.

Figure 2:
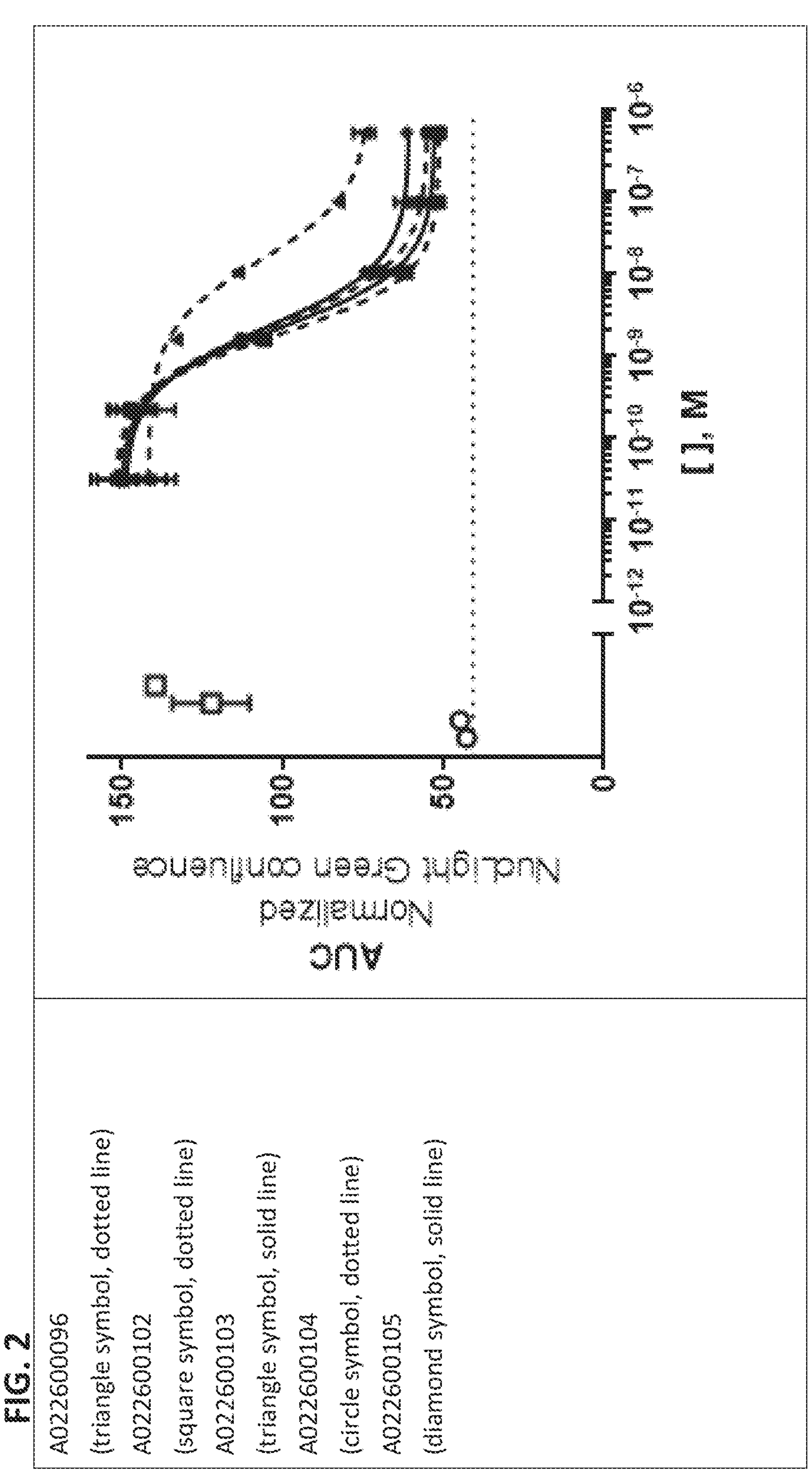

FIG. 2: Dose-dependent killing of the trispecific GPC3 ISVD T-cell engagers in the Incucyte based human TDC HepG2-Nuclight green assay using an effector to target ratio of 15:1, analyzed at 72 h after seeding. The figure represents Step 1 of format optimization where trispecific trivalent T-cell engager formats differ in linker length between anti-TCR ISVD and anti-GPC3 ISVD. Controls (left) are: No compound (open square) and reference for 100% killing (open circle).

Figure 3:
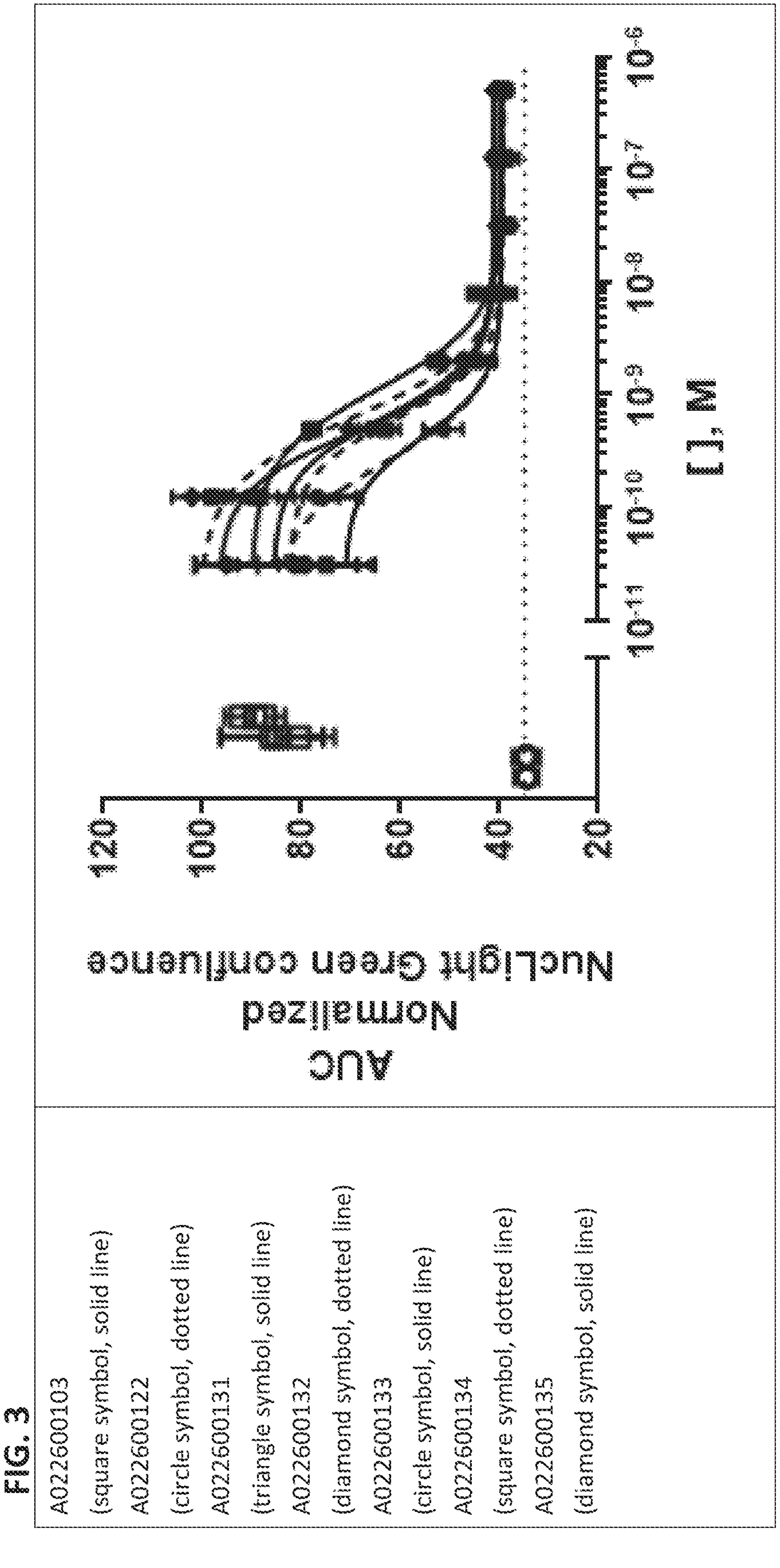

FIG. 3: Dose-dependent killing of the trispecific GPC3 ISVD T-cell engagers in the Incucyte based human TDC HepG2-Nuclight green assay using an effector to target ratio of 15:1, analyzed at 60 h after seeding. The Figure represents Step 2 of format optimization where trispecific tetravalent T-cell engager formats differ in the orientation of and the linker length between the biparatopic GPC3 binding ISVDs. Controls (left) are: No compound (open square) and reference for 100% killing (open circle).

FIGS. 4A-4B: Step 3 of GPC3 T-cell engager format optimization: the anti-TCR ISVD T017000624 was substituted by the sequenced optimized variant TCE01 in the trivalent and tetravalent formats. Dose-dependent killing of the trispecific GPC3 ISVD T-cell engagers in the Incucyte based human TDC HepG2-Nuclight green assay (FIG. 4A) and in the xCELLigence based human TDC Huh7 assay (FIG. 4B), using an effector to target ratio of 15:1, analyzed at 60 h after seeding. Controls (left) are: No compound (open square) and reference for 100% killing (open circle).

FIGS. 5A-5B: Dose-dependent killing of the trispecific GPC3 ISVD T-cell engagers in the Incucyte based human TDC HepG2-Nuclight green assay (FIG. 5A) and in the xCELLigence based human TDC Huh7 assay (FIG. 5B), using an effector to target ratio of 15:1, analyzed at 60 h after seeding. Step 4 of GPC3 T-cell engager format optimization is represented where the orientation of the anti-TCR ISVD was changed with the anti-GPC3 ISVD or the orientation of anti-GPC3 ISVD was changed with anti-Albumin ISVD. Controls (left) are: (open square) No compound and (open circle) reference for 100% killing.

FIGS. 6A-6B: Dose-dependent killing of the trispecific GPC3 ISVD T-cell engagers in the Incucyte based human TDC HepG2-Nuclight green assay (FIG. 6A) and, in the xCELLigence based human TDC Huh7 assay (FIG. 6B), using an effector to target ratio of 15:1, analyzed at 60 h after seeding. Step 5 of GPC3 T-cell engager format optimization is represented where the linker lengths are varied. Controls (left) are: (open square) No compound and (open circle) reference for 100% killing.

Figure 7A:
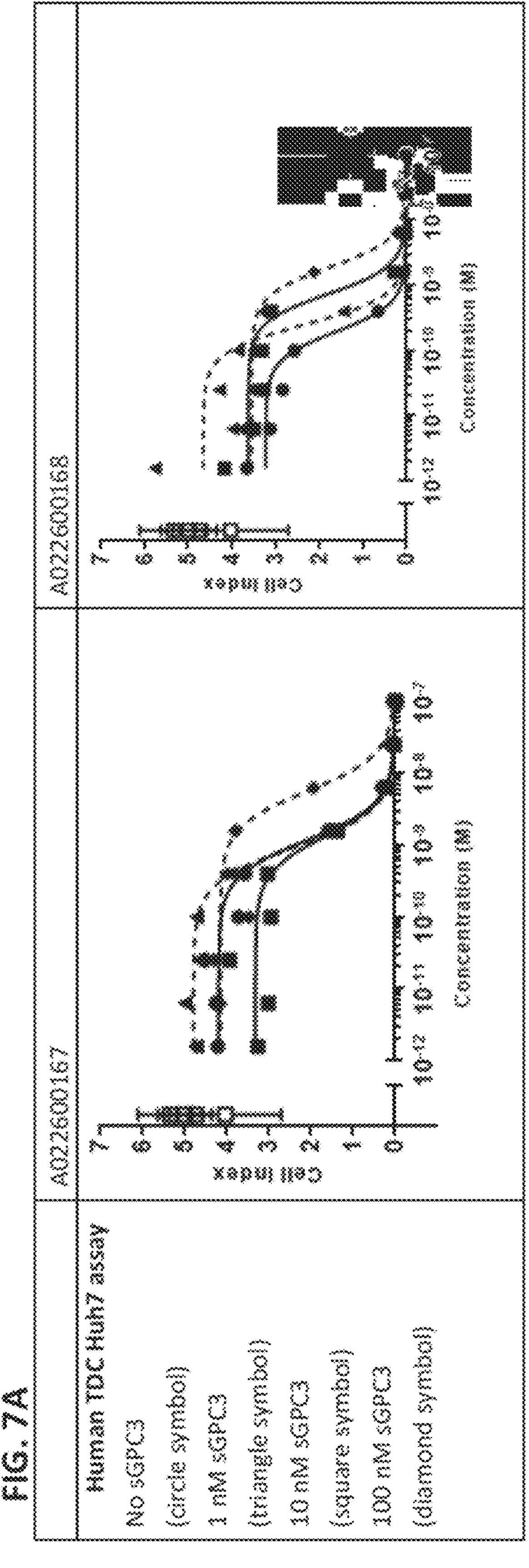
Figure 7B:
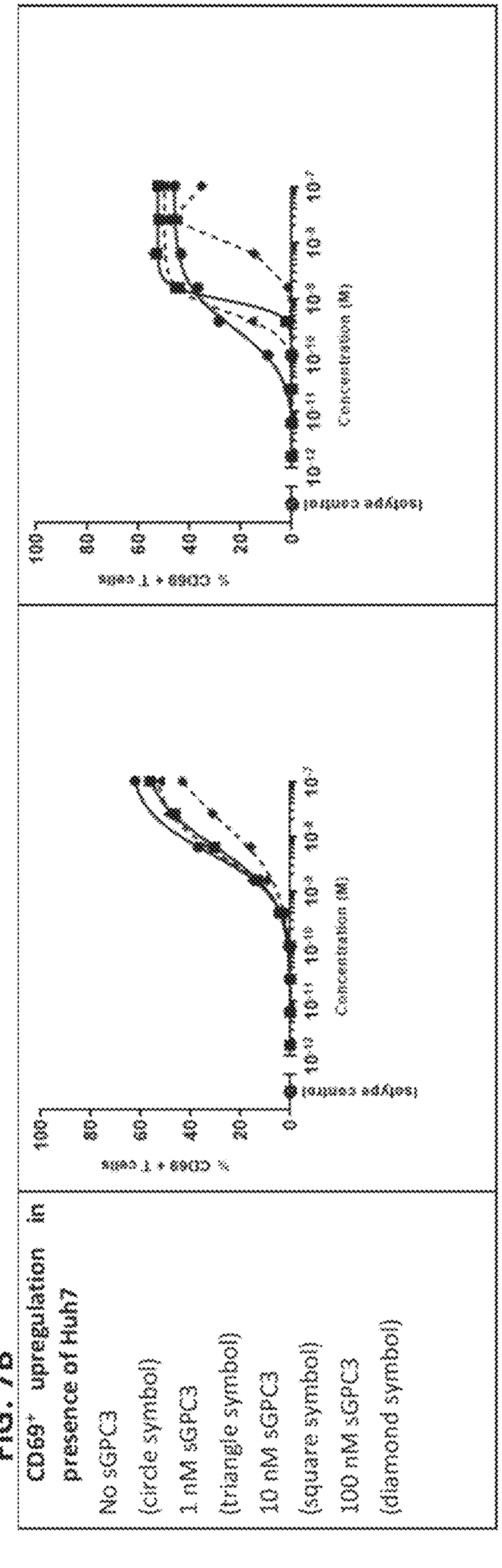
Figure 7C:
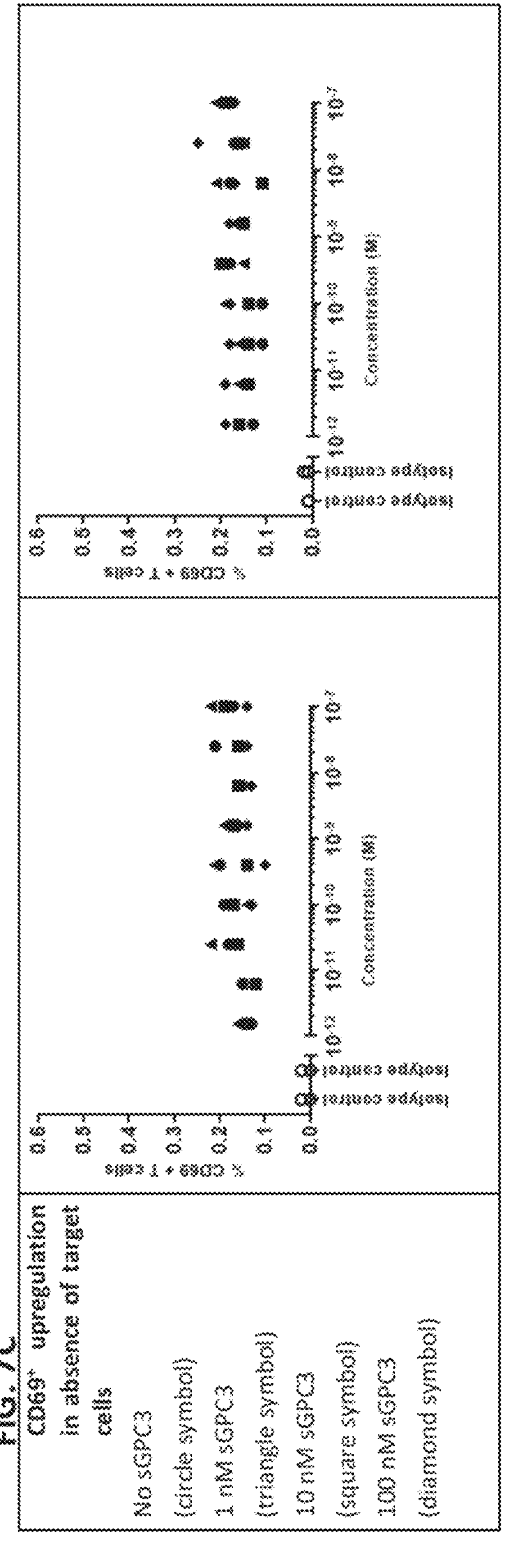

FIGS. 7A-7C: Assessment of impact of soluble GPC3 (sGPC3) on cytotoxicity of the trispecific GPC3 ISVD T-cell engagers in the xCELLigence based human TDC Huh7 assay using an effector to target ratio of 15:1, analyzed at 60 h after seeding (FIG. 7A), and on T-cell activation by the trispecific GPC3 ISVD T-cell engagers in the presence (FIG. 7B) and absence (FIG. 7C) of target cells (Huh7). Controls (left) are: No compound (open circle, FIG. 7A) and isotype control (open circle, FIGS. 7B and 7C).

Figure 8A:
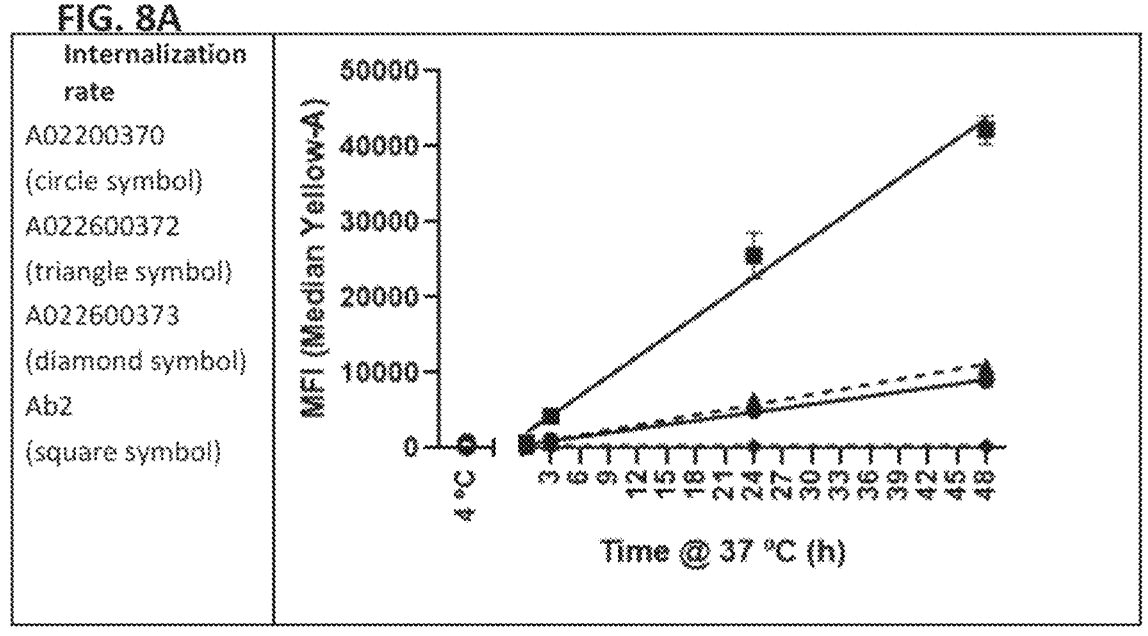
Figure 8B:
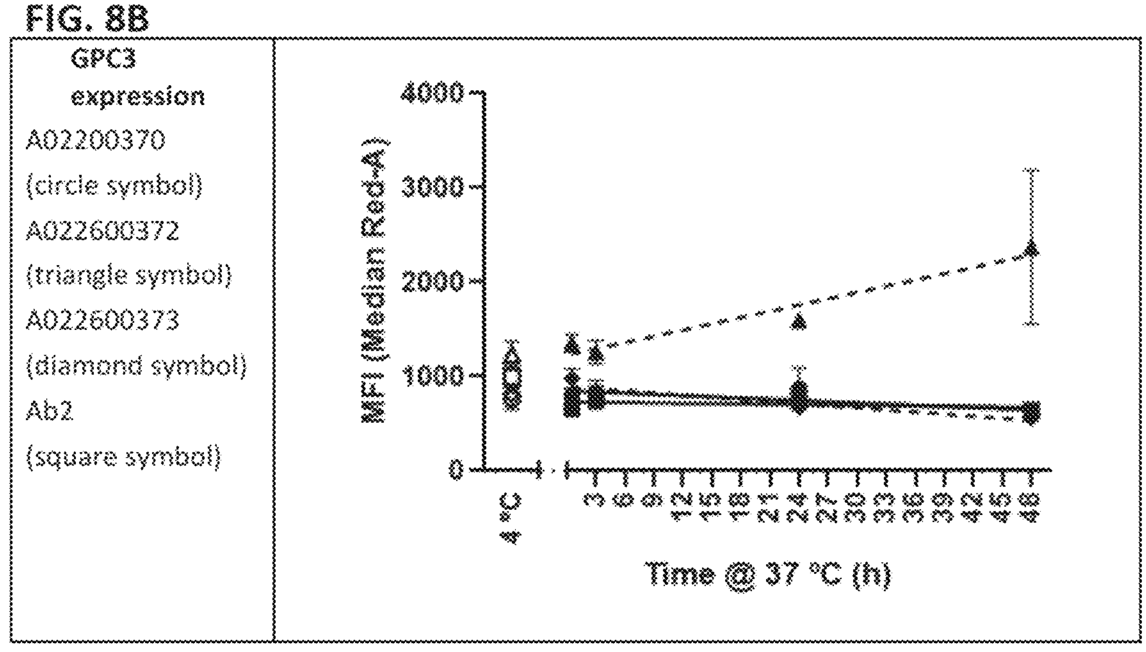

FIGS. 8A-8B: Time-course of T-cell engager internalization (FIG. 8A) and GPC3 expression (FIG. 8B) measured at 37° C. at time points 0.5 h, 3 h, 24 h and 48 h. Controls (left) are measurements at 0.5 h for each compound at 4° C.

Figures 9A, 9B:
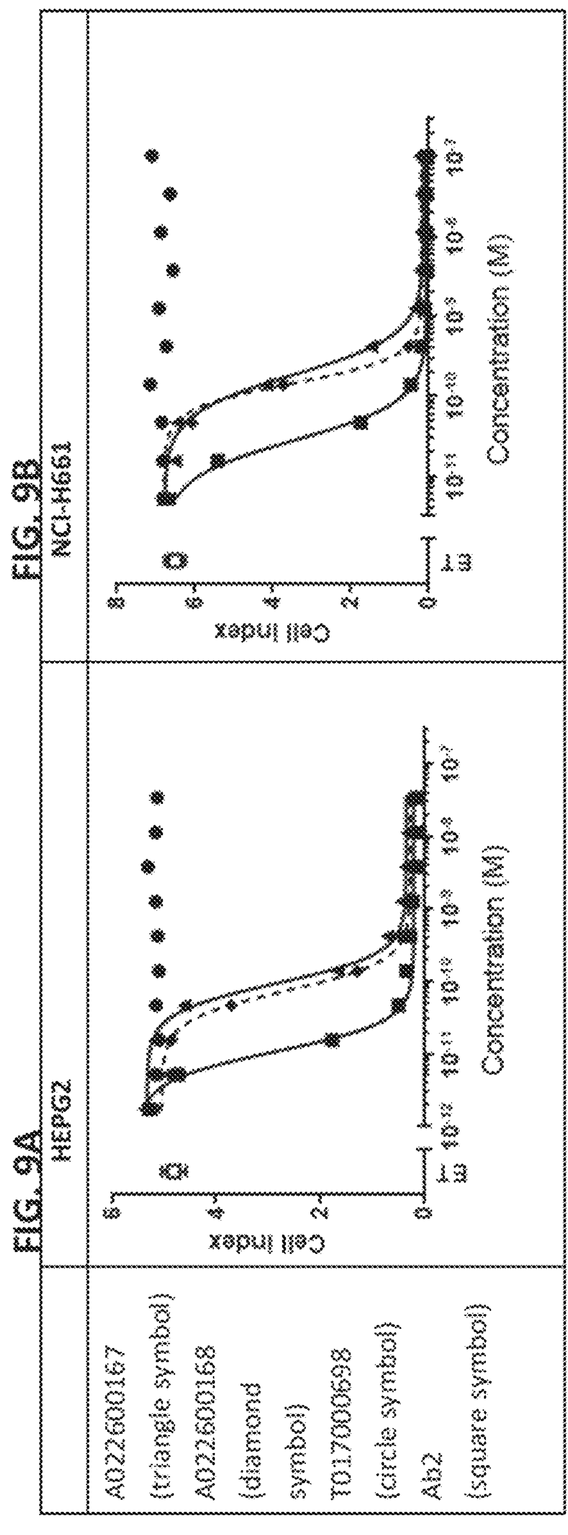
Figures 9C, 9D:
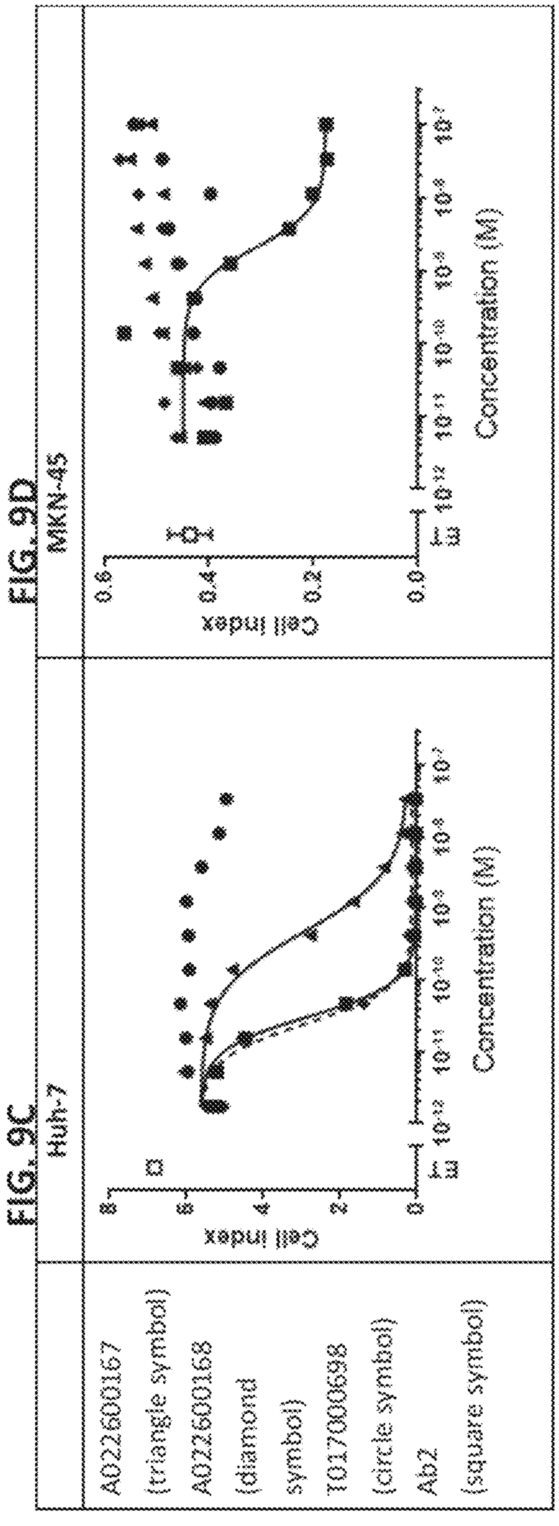
Figures 9E, 9F:
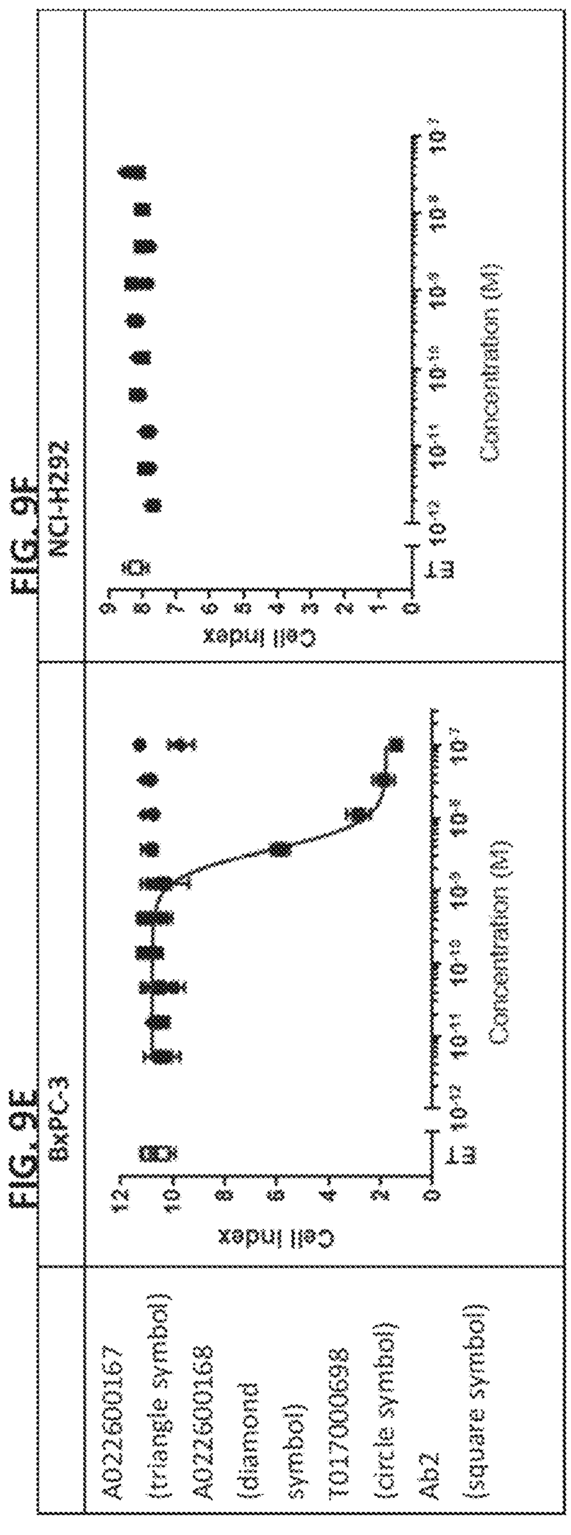

FIGS. 9A-9F: Dose-dependent killing of the trispecific GPC3 T-cell engagers in the xCELLigence based human TDC assay on different tumor cell lines expressing decreasing expression levels of GPC3 using an effector to target ratio of 15:1: HepG2 analysed at 60 h (FIG. 9A), NCI-H661 analysed at 75 h (FIG. 9B), Huh-7 analysed at 60 h (FIG. 9C), MKN-45 analysed at 65 h (FIG. 9D), BxPC-3 analysed at 65 h (FIG. 9E), NCI-H292 analysed at 60 h (FIG. 9F). Controls (left) are: (open square) No compound (effector and T cells only).

FIGS. 10A-10B: Dose-dependent killing of the five selected trispecific GPC3 ISVD based T-cell engagers in the xCELLigence based human TDC assay on two tumor cell lines using an effector to target ratio of 15:1 and analyzed at 60 h, NCI-H661 (FIG. 10A) and BxPC-3 (FIG. 10B). Controls (left) are: No compound (open square, effector and T cells only) and T017000698 at 30 nM (open diamond).

Figure 11A:
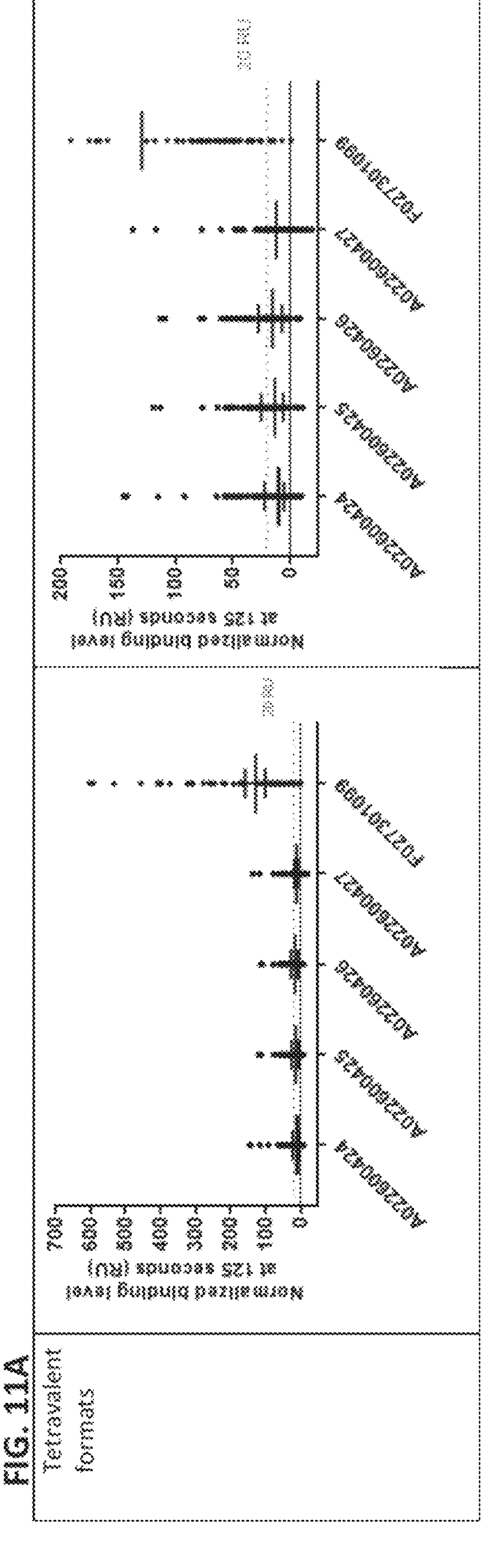
Figure 11B:
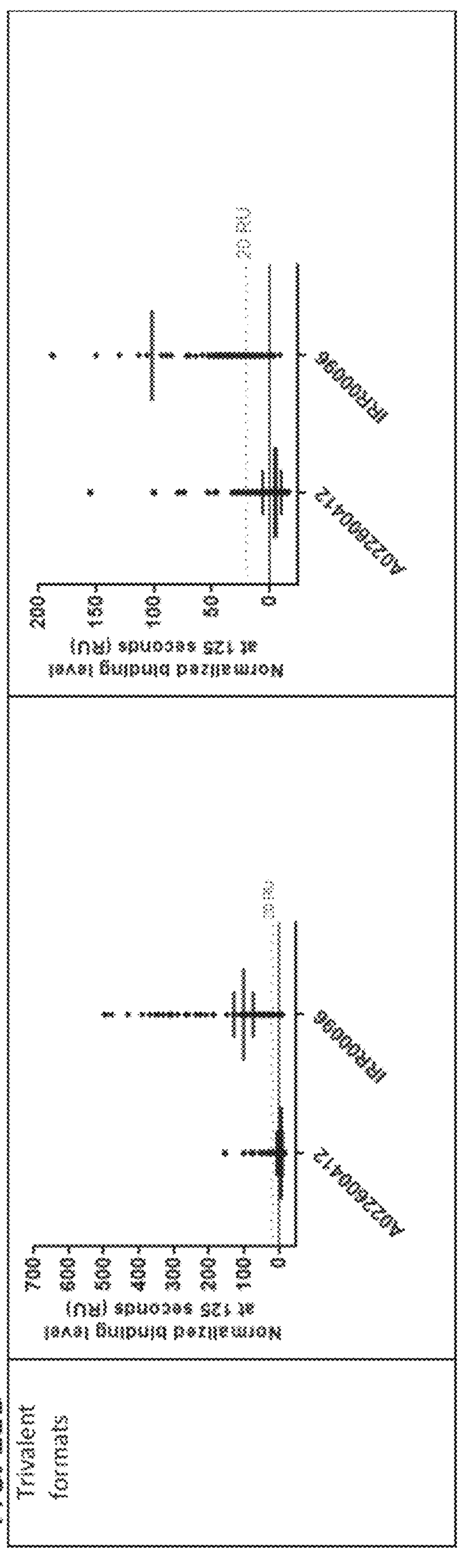

FIGS. 11A-11B: Median and interquartile range of the pre-existing antibody reactivity from 96 normal human serum samples on tetravalent (FIG. 11A) and trivalent (FIG. 11B) selected ISVD based GPC3 T-cell engager formats.

FIG. 12: Study design for efficacy model. Huh-7 tumor cells were subcutaneously injected in NOG mice. The tumors grew until the mean tumor volume of approximately 150 $mm^3$ was reached. At this point, in vitro expanded T cells were injected into each mouse intraperitoneally (DO). The treatment with A022600424 injected intravenously started on DO, 3 h after T cell injection and continued on D3, D6, D9 and D12 (q3d). Four dose levels of A022600424 were tested (0.1 mg/kg, 0.2 mg/kg, 0.7 mg/kg and 2 mg/kg). The control T017000698 was injected in a control group at 2 mg/kg on DO, D3, D6, D9 and D12 (q3d). Survival blood sampling was done on D6 and D12 prior to administration of test compounds. All mice were sacrificed on D15, blood and tumor samples were collected.

Figure 13:
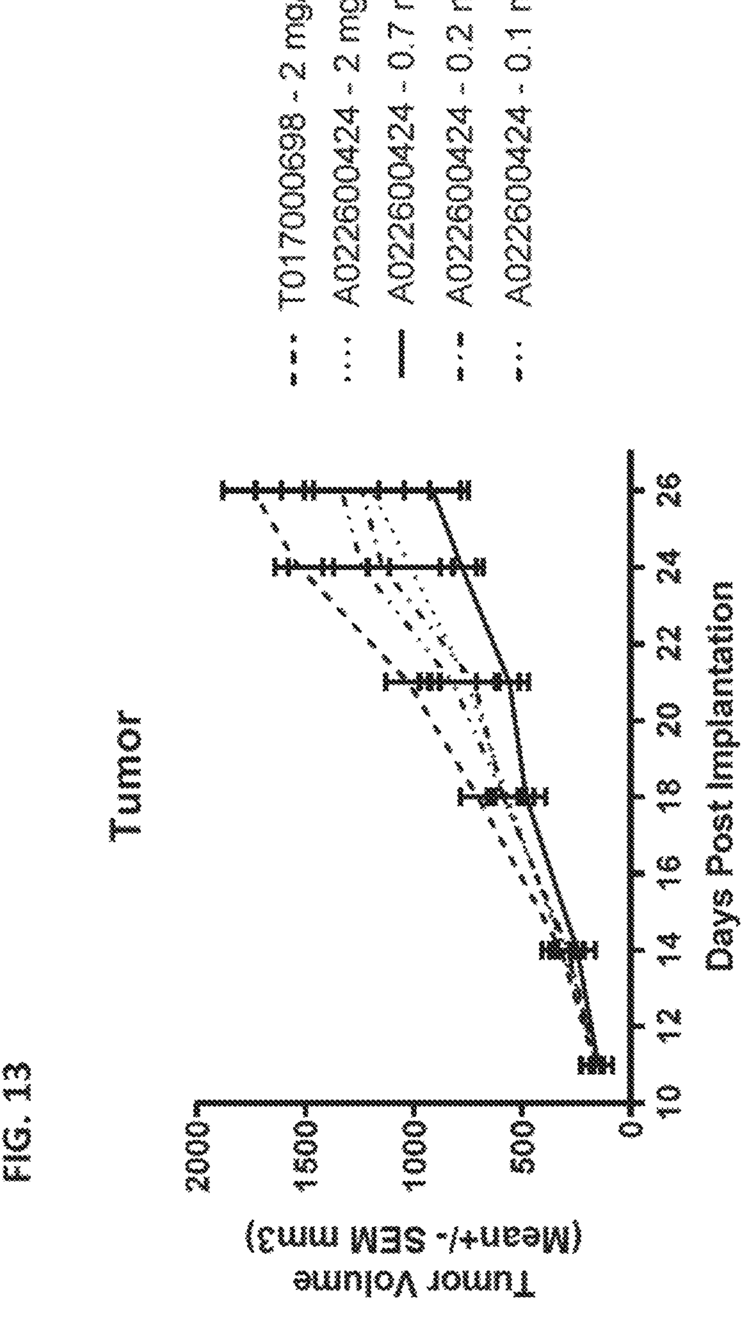

FIG. 13: Results of the efficacy model. Four dose levels of A022600424 were tested (0.1 mg/kg, 0.2 mg/kg, 0.7 mg/kg and 2 mg/kg). The control T017000698 was injected in a control group at 2 mg/kg.

DETAILED DESCRIPTION OF THE INVENTION

The present technology aims at providing a novel type of drug for treating cancer, such as liver cancer or lung cancer.

The present inventors found that a polypeptide targeting specifically GPC3 and TCR at the same time leads to efficient T cell-mediated killing of GPC3 expressing cells in vitro. Said polypeptides could be efficiently produced (e.g. in microbial hosts). Furthermore, such polypeptides could be shown to exhibit limited reactivity to pre-existing antibodies in the subject to be treated (i.e., antibodies present in the subject before the first treatment with the antibody construct). In preferred embodiments such polypeptides exhibit a half-life in the subject to be treated that is long enough such that consecutive treatments can be conveniently spaced apart. Moreover, such polypeptides showed only limited activity against cells expressing no or low levels of GPC3. This suggests the possibility of inducing a highly specific T cell-mediated cytotoxic response against GPC3 positive target cells.

Apart from the above, the GPC3-binding ISVDs disclosed herein provide high affinity-binding to human and cyno GPC3 and can thus be readily used in monovalent or multivalent form for other applications in which binding to GPC3 is required.

5.1 Polypeptides

Monospecific-Monovalent Polypeptides

In one aspect, the polypeptide is monospecific and monovalent.

The term "monospecific" refers to the binding to one (specific) type of target molecule(s). A monospecific polypeptide thus specifically binds to GPC3.

The term "monovalent" indicates the presence of only one binding units/building block that (specifically) targets a molecule, such as an ISVDs.

Accordingly, in one aspect the present technology provides a monospecific-monovalent polypeptide comprising or consisting of one ISVD that specifically binds to GPC3, preferably human GPC3, which comprises three complementarity determining regions (CDR1 to CDR3, respectively). The ISVD can be selected from an ISVD comprising:

a) a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15; or b) a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of GVA or an amino acid sequence with 2 or 1 amino acid difference(s) with GVA.

Preferably, the ISVD specifically binding to GPC3 is selected from an ISVD comprising:

a) a CDR1 that is the amino acid sequence of SEQ ID NO: 7, a CDR2 that is the amino acid sequence of SEQ ID NO: 11 and a CDR3 that is the amino acid sequence of SEQ ID NO: 15; or b) a CDR1 that is the amino acid sequence of SEQ ID NO: 8, a CDR2 that is the amino acid sequence of SEQ ID NO: 12 and a CDR3 that is the amino acid sequence of GVA.

In a further embodiment of this aspect of the technology, the ISVD specifically binding to GPC3 is selected from an ISVD comprising:

a) an amino acid sequence with a sequence identity of more than 90% with SEQ ID NO: 3, preferably wherein the ISVD comprises or consists of the amino acid sequence of SEQ ID NO: 3; or b) an amino acid sequence with a sequence identity of more than 90% with SEQ ID NO: 4, preferably wherein the ISVD comprises or consists of the amino acid sequence of SEQ ID NO: 4.

In another aspect the present technology provides a monospecific-monovalent polypeptide comprising or consisting of one ISVD that specifically binds to the constant domain of a TCR on a T cell, preferably human TCR, which comprises three complementarity determining regions (CDR1 to CDR3, respectively). The ISVD can be an ISVD comprising a CDR1 that is the amino acid sequence of SEQ ID NO: 6 or an amino acid sequence with 2 or 1 amino acid difference(s) with SEQ ID NO: 6, a CDR2 that is the amino acid sequence of SEQ ID NO: 10 or an amino acid sequence with 2 or 1 amino acid difference(s) with SEQ ID NO: 10, and a CDR3 that is the amino acid sequence of SEQ ID NO:

14 or an amino acid sequence with 2 or 1 amino acid difference(s) with SEQ ID NO: 14.

Preferably, the ISVD specifically binding to TCR is an ISVD comprising a CDR1 that is the amino acid sequence of SEQ ID NO: 6, a CDR2 that is the amino acid sequence of SEQ ID NO: 10 and a CDR3 that is the amino acid sequence of SEQ ID NO: 14.

In a further embodiment of this aspect of the technology, the ISVD specifically binding to TCR is an ISVD comprising an amino acid sequence with a sequence identity of more than 90% with SEQ ID NO: 2, preferably wherein the ISVD comprises or consists of the amino acid sequence of SEQ ID NO: 2.

These monovalent compounds can also serve as building blocks for multivalent and/or multispecific polypeptides.

An ISVD located at the N-terminus of a (monovalent or multivalent) polypeptide comprising the same preferably does not exhibit glutamic acid (E) at its N-terminal end. Therefore, glutamic acid (E) at position 1 is typically substituted by aspartic acid (D) in an ISVD located at the N-terminus of the polypeptide. Thus, for example, if SEQ ID NOs: 3, 4 or 5 are located at the N-terminus of the polypeptide, these sequences will typically exhibit a E1D substitution. Conversely, if SEQ ID NO: 2 is not located at the N-terminus, this sequence will typically exhibit a D1E mutation. Thus, generally, the first position of SEQ ID NOs: 2-5 can be E or D, depending on whether these sequences are located at the N-terminus or not. In a preferred embodiment, the first amino acid of the first ISVD comprised in the polypeptide of the present technology is an aspartic acid (D).

Monospecific-Multivalent Polypeptides

In another aspect, the polypeptide is monospecific and at least bivalent, but can also be e.g., trivalent, tetravalent, pentavalent, hexavalent, etc.

The terms “bivalent”, “trivalent”, “tetravalent”, “pentavalent”, or “hexavalent” all fall under the term “multivalent” and indicate the presence of two, three, four, five or six binding units/building blocks, respectively, such as ISVDs.

Accordingly, in one aspect the present technology provides a monospecific-bivalent polypeptide comprising or consisting of two ISVDs that specifically bind to GPC3, preferably human GPC3, wherein each of the two ISVDs comprises three complementarity determining regions (CDR1 to CDR3, respectively), wherein the two ISVDs are preferably linked via one or more peptidic linkers, and wherein:

a) a first and a second ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15;

b) a first and a second ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of GVA or an amino acid sequence with 2 or 1 amino acid difference (s) with GVA;

c) a first ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15, and a second ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of GVA or an amino acid sequence with 2 or 1 amino acid difference(s) with GVA; or d) a first ISVD comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of GVA or an amino acid sequence with 2 or 1 amino acid difference(s) with GVA, and a second ISVD comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15.

Preferably, the monospecific-bivalent polypeptide comprises or consists of two ISVDs that specifically bind to GPC3, wherein:

a) the first and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15;

b) the first and the second ISVD comprises a CDR1 being the amino acid sequence of SEQ ID NO: 8, a CDR2 being the amino acid sequence of SEQ ID NO: 12 and a CDR3 being the amino acid sequence of GVA;

c) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 8, a CDR2 being the amino acid sequence of SEQ ID NO: 12 and a CDR3 being the amino acid sequence of GVA; or d) the first ISVD comprises a CDR1 being the amino acid sequence of SEQ ID NO: 8, a CDR2 being the amino acid sequence of SEQ ID NO: 12 and a CDR3 being the amino acid sequence of GVA, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15.

In a further embodiment of this aspect of the technology, the monospecific-bivalent polypeptide comprises or consists of two ISVDs that specifically bind to GPC3, wherein:

a) the amino acid sequence of the first and the second ISVD exhibits a sequence identity of more than 90% with SEQ ID NO: 3, wherein the first and the second ISVD preferably consists of the amino acid sequence of SEQ ID NO: 3;

b) the amino acid sequence of the first and the second ISVD exhibits a sequence identity of more than 90% with SEQ ID NO: 4, wherein the first and the second ISVD preferably consists of the amino acid sequence of SEQ ID NO: 4:

c) the amino acid sequence of the first ISVD exhibits a sequence identity of more than 90% with SEQ ID NO: 3 and the second ISVD exhibits a sequence identity of more than 90% identity with SEQ ID NO: 4, preferably wherein the first ISVD consists of the amino acid sequence of SEQ ID NO: 3 and the second ISVD consists of the amino acid sequence of SEQ ID NO: 4; or d) the amino acid sequence of the first ISVD exhibits a sequence identity of more than 90% with SEQ ID NO: 4 and the second ISVD exhibits a sequence identity of more than 90% identity with SEQ ID NO: 3, preferably wherein the first ISVD consists of the amino acid sequence of SEQ ID NO: 4 and the second ISVD consists of the amino acid sequence of SEQ ID NO: 3.

The terms "first ISVD" and "second ISVD" in this regard only indicate the relative position of the specifically recited ISVDs binding to GPC3 to each other, wherein the numbering is started from the N-terminus of the polypeptide. The "first ISVD" is thus closer to the N-terminus than the "second ISVD". Accordingly, the "second ISVD" is thus closer to the C-terminus than the "first ISVD". Since the numbering is not absolute and only indicates the relative position of the two ISVDs it does not exclude the possibility that additional binding units/building blocks such as ISVDs binding to GPC3, TCR or serum albumin, respectively, can be present in the polypeptide. Moreover, it does not exclude the possibility that other binding units/building blocks such as ISVDs can be placed in between. For instance, as described further below (see in particular, section "multi-specific-multivalent polypeptides" and 5.4 "(In vivo) half-life extension"), the polypeptide can further comprise another ISVD binding to human serum albumin that can even be located between the "first ISVD" and "second ISVD" (such a construct is then referred to as multispecific as described in the subsequent section).

In a preferred embodiment, the (at least two) ISVDs of the monospecific-multivalent polypeptides, in particular of the above described monospecific-bivalent polypeptides, are linked via peptidic linkers. The use of peptidic linkers to connect two or more (poly)peptides is well known in the art. Exemplary peptidic linkers that can be used with the monospecific-multivalent polypeptides, in particular with the above described monospecific-bivalent polypeptides, are shown in Table A-5. One often used class of peptidic linkers is known as the "Gly-Ser" or "GS" linkers. These are linkers that essentially consist of glycine (G) and serine (S) residues, and usually comprise one or more repeats of a peptide motif such as the GGGGS (SEQ ID NO: 100) motif (for example, exhibiting the formula (Gly-Gly-Gly-Gly-Ser)$_n$ in which n may be 1, 2, 3, 4, 5, 6, 7 or more). Some often used examples of such GS linkers are 9GS linkers (GGGGSGGGS, SEQ ID NO: 103) 15GS linkers (n=3) and 35GS linkers (n=7). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In one embodiment, the ISVDs of the monospecific-multivalent polypeptides, in particular the monospecific-bivalent polypeptides are linked via a linker set forth in Table A-5. In one embodiment, the (at least) two ISVDs are linked via a 35GS or a 9GS linker. In a preferred embodiment, the (at least) two ISVDs are linked via a 9GS linker(s).

Multispecific-Multivalent Polypeptides

In a further aspect, the polypeptide is at least bispecific, but can also be e.g., trispecific, tetraspecific, pentaspecific, etc. Moreover, the polypeptide is at least bivalent, but can also be e.g., trivalent, tetravalent, pentavalent, hexavalent, etc.

The terms "bispecific", "trispecific", "tetraspecific", "pentaspecific", etc., all fall under the term "multispecific" and refer to binding to two, three, four, five, etc., different target molecules, respectively.

The terms "bivalent", "trivalent", "tetravalent", "pentavalent", "hexavalent", etc. all fall under the term "multivalent" and indicate the presence of two, three, four, five, six, etc., binding units/building blocks, respectively, such as ISVDs.

For example, the polypeptide may be bispecific-bivalent, such as a polypeptide comprising or consisting of two ISVDs, wherein one ISVD specifically binds to GPC3 and one ISVD specifically binds to the constant domain of a TCR on a T cell, wherein the GPC3 and TCR are preferably human GPC3 and human TCR. The polypeptide may also be bispecific-trivalent, such as a polypeptide comprising or consisting of three ISVDs, wherein two ISVD specifically bind to GPC3 and one ISVD specifically binds to the constant domain of a TCR on a T cell, wherein the GPC3 and TCR are preferably human GPC3 and human TCR. In another example, the polypeptide may be trispecific-tetravalent, such as a polypeptide comprising or consisting of four ISVDs, wherein two ISVDs specifically bind to human GPC3, one ISVD specifically binds to the constant domain of a human TCR on a T cell and one ISVD binds to human serum albumin. Such a polypeptide may at the same time be biparatopic, for example if two ISVDs bind two different epitopes on human GPC3. The term "biparatopic" refers to binding to two different parts (e.g., epitopes) of the same target molecule. A preferred trispecific-tetravalent polypeptide is e.g., ISVD construct A022600424, comprising two ISVDs specifically binding to human GPC3, one ISVD specifically binding to the constant domain of a human TCR on a T cell, one ISVD binding to human serum albumin, and which is biparatopic for binding to GPC3.

In one embodiment, the present technology provides a bispecific-bivalent polypeptide comprising or consisting of at least two ISVDs, wherein each of said ISVDs comprises three complementarity determining regions (CDR1 to CDR3, respectively), wherein the at least two ISVDs are optionally linked via one or more peptidic linkers, and wherein:

a) a first ISVD comprises
   i. a CDR1 that is the amino acid sequence of SEQ ID NO: 6 or an amino acid sequence with 2 or 1 amino acid difference(s) with SEQ ID NO: 6;
   ii. a CDR2 that is the amino acid sequence of SEQ ID NO: 10 or an amino acid sequence with 2 or 1 amino acid difference(s) with SEQ ID NO: 10; and
   iii. a CDR3 that is the amino acid sequence of SEQ ID NO: 14 or an amino acid sequence with 2 or 1 amino acid difference(s) with SEQ ID NO: 14, and a second ISVD comprises
   iv. a CDR1 that is the amino acid sequence of SEQ ID NO: 7 or an amino acid sequence with 2 or 1 amino acid difference(s) with SEQ ID NO: 7;

v. a CDR2 that is the amino acid sequence of SEQ ID NO: 11 or an amino acid sequence with 2 or 1 amino acid difference(s) with SEQ ID NO: 11; and vi. a CDR3 that is the amino acid sequence of SEQ ID NO: 15 or an amino acid sequence with 2 or 1 amino acid difference(s) with SEQ ID NO: 15, b) a first ISVD comprises i. a CDR1 that is the amino acid sequence of SEQ ID NO: 7 or an amino acid sequence with 2 or 1 amino acid difference(s) with SEQ ID NO: 7;

ii. a CDR2 that is the amino acid sequence of SEQ ID NO: 11 or an amino acid sequence with 2 or 1 amino acid difference(s) with SEQ ID NO: 11; and iii. a CDR3 that is the amino acid sequence of SEQ ID NO: 15 or an amino acid sequence with 2 or 1 amino acid difference(s) with SEQ ID NO: 15, and a second ISVD comprises iv. a CDR1 that is the amino acid sequence of SEQ ID NO: 6 or an amino acid sequence with 2 or 1 amino acid difference(s) with SEQ ID NO: 6;

v. a CDR2 that is the amino acid sequence of SEQ ID NO: 10 or an amino acid sequence with 2 or 1 amino acid difference(s) with SEQ ID NO: 10; and vi. a CDR3 that is the amino acid sequence of SEQ ID NO: 14 or an amino acid sequence with 2 or 1 amino acid difference(s) with SEQ ID NO: 14, c) a first ISVD comprises i. a CDR1 that is the amino acid sequence of SEQ ID NO: 6 or an amino acid sequence with 2 or 1 amino acid difference(s) with SEQ ID NO: 6;

ii. a CDR2 that is the amino acid sequence of SEQ ID NO: 10 or an amino acid sequence with 2 or 1 amino acid difference(s) with SEQ ID NO: 10; and iii. a CDR3 that is the amino acid sequence of SEQ ID NO: 14 or an amino acid sequence with 2 or 1 amino acid difference(s) with SEQ ID NO: 14, and a second ISVD comprises iv. a CDR1 that is the amino acid sequence of SEQ ID NO: 8 or an amino acid sequence with 2 or 1 amino acid difference(s) with SEQ ID NO: 8;

v. a CDR2 that is the amino acid sequence of SEQ ID NO: 12 or an amino acid sequence with 2 or 1 amino acid difference(s) with SEQ ID NO: 12; and vi. a CDR3 that is the amino acid sequence of GVA or an amino acid sequence with 2 or 1 amino acid difference(s) with GVA, or d) a first ISVD comprises i. a CDR1 that is the amino acid sequence of SEQ ID NO: 8 or an amino acid sequence with 2 or 1 amino acid difference(s) with SEQ ID NO: 8;

ii. a CDR2 that is the amino acid sequence of SEQ ID NO: 12 or an amino acid sequence with 2 or 1 amino acid difference(s) with SEQ ID NO: 12; and iii. a CDR3 that is the amino acid sequence of GVA or an amino acid sequence with 2 or 1 amino acid difference(s) with GVA, and a second ISVD comprises iv. a CDR1 that is the amino acid sequence of SEQ ID NO: 6 or an amino acid sequence with 2 or 1 amino acid difference(s) with SEQ ID NO: 6;

v. a CDR2 that is the amino acid sequence of SEQ ID NO: 10 or an amino acid sequence with 2 or 1 amino acid difference(s) with SEQ ID NO: 10; and vi. a CDR3 that is the amino acid sequence of SEQ ID NO: 14 or an amino acid sequence with 2 or 1 amino acid difference(s) with SEQ ID NO: 14.

In a preferred embodiment, such a polypeptide comprises or consists of at least two ISVDs, wherein each of said ISVDs comprises three complementarity determining regions (CDR1 to CDR3, respectively), wherein the at least two ISVDs are optionally linked via one or more peptidic linkers, and wherein a) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, b) the first ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, c) the first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14, and the second ISVD comprises a CDR1 being the amino acid sequence of SEQ ID NO: 8, a CDR2 being the amino acid sequence of SEQ ID NO: 12 and a CDR3 being the amino acid sequence of GVA, or d) the first ISVD comprises a CDR1 being the amino acid sequence of SEQ ID NO: 8, a CDR2 being the amino acid sequence of SEQ ID NO: 12 and a CDR3 being the amino acid sequence of GVA, and the second ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14.

Thus, such a polypeptide can be a polypeptide, wherein:

a) the amino acid sequence of the first ISVD exhibits a sequence identity of more than 90% with SEQ ID NO: 2, and the second ISVD exhibits a sequence identity of more than 90% identity with SEQ ID NO: 3, b) the amino, acid sequence of the first ISVD exhibits a sequence identity of more than 90% with SEQ ID NO: 3, and the second ISVD exhibits a sequence identity of more than 90% identity with SEQ ID NO: 2 c) the amino acid sequence of the first ISVD exhibits a sequence identity of more than 90% with SEQ ID NO: 2, and the second ISVD exhibits a sequence identity of more than 90% identity with SEQ ID NO: 4, or d) the amino acid sequence of the first ISVD exhibits a sequence identity of more than 90% with SEQ ID NO: 4, and the second ISVD exhibits a sequence identity of more than 90% identity with SEQ ID NO: 2.

Preferably, in such a polypeptide:

a) the first ISVD consists of the amino acid sequence of SEQ ID NO: 2, and the second ISVD consists of the amino acid sequence of SEQ ID NO: 3, b) the first ISVD consists of the amino acid sequence of SEQ ID NO: 3, and the second ISVD consists of the amino acid sequence of SEQ ID NO: 2, c) the first ISVD consists of the amino acid sequence of SEQ ID NO: 2, and the second ISVD consists of the amino acid sequence of SEQ ID NO: 4, or d) the first ISVD consists of the amino acid sequence of SEQ ID NO: 4, and the second ISVD consists of the amino acid sequence of SEQ ID NO: 2.

In another aspect, the present technology provides a trispecific-trivalent polypeptide comprising the bispecific-bivalent polypeptides described above and a third ISVD binding to human serum albumin as described in detail below (section 5.4; "(In vivo) half-life extension").

In one embodiment, the present technology provides a bispecific-trivalent polypeptide comprising or consisting of at least three ISVDs, wherein each of said ISVDs comprises three complementarity determining regions (CDR1 to CDR3, respectively), wherein the at least three ISVDs are optionally linked via one or more peptidic linkers, and wherein:

a) a first ISVD specifically binds the constant domain of a TCR on a T cell and comprises a CDR1 that is the amino acid sequence of SEQ ID NO: 6 or an amino acid sequence with 2 or 1 amino acid difference(s) with SEQ ID NO: 6, a CDR2 that is the amino acid sequence of SEQ ID NO: 10 or an amino acid sequence with 2 or 1 amino acid difference(s) with SEQ ID NO: 10, and a CDR3 that is the amino acid sequence of SEQ ID NO: 14 or an amino acid sequence with 2 or 1 amino acid difference(s) with SEQ ID NO: 14;
b) a second ISVD specifically binds GPC3 and comprises a CDR1 that is the amino acid sequence of SEQ ID NO: 7 or an amino acid sequence with 2 or 1 amino acid difference(s) with SEQ ID NO: 7, a CDR2 that is the amino acid sequence of SEQ ID NO: 11 or an amino acid sequence with 2 or 1 amino acid difference(s) with SEQ ID NO: 11, and a CDR3 that is the amino acid sequence of SEQ ID NO: 15 or an amino acid sequence with 2 or 1 amino acid difference(s) with SEQ ID NO: 15; and
c) a third ISVD specifically binds GPC3 and comprises a CDR1 that is the amino acid sequence of SEQ ID NO: 8 or an amino acid sequence with 2 or 1 amino acid difference(s) with SEQ ID NO: 8, a CDR2 that is the amino acid sequence of SEQ ID NO: 12 or an amino acid sequence with 2 or 1 amino acid difference(s) with SEQ ID NO: 12, and a CDR3 that is the amino acid sequence of GVA or an amino acid sequence with 2 or 1 amino acid difference(s) with GVA, wherein the TCR and GPC3 bound by said polypeptide is preferably human TCR and human GPC3, respectively.

In a preferred embodiment of the multispecific-multivalent polypeptide:

a) said first ISVD comprises a CDR1 being the amino acid sequence of SEQ ID NO: 6, a CDR2 being the amino acid sequence of SEQ ID NO: 10 and a CDR3 being the amino acid sequence of SEQ ID NO: 14;
b) said second ISVD comprises a CDR1 being the amino acid sequence of SEQ ID NO: 7, a CDR2 being the amino acid sequence of SEQ ID NO: 11 and a CDR3 being the amino acid sequence of SEQ ID NO: 15; and
c) said third ISVD comprises a CDR1 being the amino acid sequence of SEQ ID NO: 8, a CDR2 being the amino acid sequence of SEQ ID NO: 12 and a CDR3 being the amino acid sequence of GVA.

In a further aspect of the multispecific-multivalent polypeptide:

a) the amino acid sequence of said first ISVD exhibits a sequence identity of more than 90% with SEQ ID NO: 2, wherein preferably said first ISVD consists of the amino acid sequence of SEQ ID NO: 2;
b) the amino acid sequence of said second ISVD exhibits a sequence identity of more than 90% with SEQ ID NO: 3, wherein preferably said second ISVD consists of the amino acid sequence of SEQ ID NO: 3; and
c) the amino acid sequence of said third ISVD exhibits a sequence identity of more than 90% identity with SEQ ID NO: 4, wherein preferably said third ISVD consists of the amino acid sequence of SEQ ID NO: 4.

The terms "first ISVD", "second ISVD", "third ISVD", etc., in this regard only indicate the relative position of the ISVDs to each other, wherein the numbering is started from the N-terminus of the polypeptide. The "first ISVD" is thus closer to the N-terminus than the "second ISVD", whereas the "second ISVD" is closer to the N-terminus than the "third ISVD". Accordingly, the ISVD arrangement is inverse when considered from the C-terminus. Since the numbering is not absolute and only indicates the relative position of the at least four ISVDs it is not excluded that other binding units/building blocks such as additional ISVDs binding to GPC3, or ISVDs binding to another target may be present in the polypeptide. Moreover, it does not exclude the possibility that other binding units/building blocks such as ISVDs can be placed in between. For instance, as described further below (see in particular, section 5.4 "(In vivo) half-life extension" below), the polypeptide can further comprise another ISVD binding to human serum albumin that can even be located between e.g. the "third ISVD" and "fourth ISVD".

In a further aspect the present technology thus provides a trispecific-tetravalent polypeptide comprising the bispecific-trivalent polypeptides described above and a fourth ISVD binding to human serum albumin as described in detail below (section 5.4; "(In vivo) half-life extension").

In a preferred embodiment, the first ISVD binding to TCR is positioned at the N-terminus of the polypeptide.

In another aspect the present technology provides a bispecific-bivalent polypeptide comprising an ISVD that specifically binds to GPC3 as described in detail for the monospecific-monovalent polypeptides above (section 5.1; "Monospecific-monovalent polypeptides") and an ISVD binding to human serum albumin as described in detail below (section 5.4; "(In vivo) half-life extension").

In another aspect the present technology provides a bispecific-trivalent polypeptide comprising the monospecific-bivalent polypeptides above (section 5.1; "monospecific-bivalent polypeptides") and an ISVD binding to human serum albumin as described in detail below (section 5.4; "(In vivo) half-life extension").

The components, preferably ISVDs, of said multispecific-multivalent polypeptides described herein may be linked to each other by one or more suitable linkers, such as peptidic linkers.

The use of linkers to connect two or more (poly)peptides is well known in the art. Exemplary peptidic linkers are shown in Table A-5. One often used class of peptidic linker are known as the "Gly-Ser" or "GS" linkers. These are linkers that essentially consist of glycine (G) and serine (S) residues, and usually comprise one or more repeats of a peptide motif such as the GGGGS (SEQ ID NO: 100) motif (for example, exhibiting the formula (Gly-Gly-Gly-Gly-Ser)$_n$ in which n may be 1, 2, 3, 4, 5, 6, 7 or more). Some often used examples of such GS linkers are 9GS linkers (GGGGSGGGS, SEQ ID NO: 103) 15GS linkers (n=3) and 35GS linkers (n=7). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In the polypeptide(s) disclosed herein, the use of 5GS and 9GS linkers to link the components of the polypeptide to each other is preferred. Preferably, a linker of less than 10 amino acids, such as less than 6 amino acids, in particular a 5GS linker, is used to link a first ISVD specifically binding to TCR to a second ISVD specifically binding to GPC3.

In one aspect of the multispecific-multivalent polypeptide, the polypeptide comprising or consisting of at least three ISVDs, comprises the at least two ISVDs specifically binding to GPC3 and one ISVD specifically binding to TCR. In this aspect of the technology, the ISVD binding to TCR is linked to one of the at least two ISVDs binding to GPC3 via a 5GS linker, whereas the at least two ISVDs specifically binding to GPC3 are linked to each other via a 9GS linker. In further aspect, the multispecific-multivalent polypeptide further comprises an ISVD binding to albumin, which is further linked via a 9 GS linker to the ISVD binding to GPC3 that is not linked to the ISVD binding to TCR (as described in section 5.4 "(In vivo) half-life extension" below). The inventors surprisingly found that such a configuration can increase the efficiency of the polypeptide in eliciting a T cell-mediated cytotoxic response.

Accordingly, it is preferred that the polypeptide comprises or consists of the following, in the order starting from the N-terminus of the polypeptide: a first ISVD specifically binding to TCR, a second ISVD specifically binding to GPC3, a third ISVD specifically binding to GPC3, and an optional binding unit providing the polypeptide with increased half-life as defined herein. The binding unit providing the polypeptide with increased half-life is preferably an ISVD, that preferably binds to serum albumin.

It is even more preferred that the polypeptide comprises or consists of the following, in the order starting from the N-terminus of the polypeptide: an ISVD specifically binding to TCR, a linker, a second ISVD specifically binding to GPC3, a linker, a third ISVD specifically binding to GPC3, a linker, and an ISVD binding to human serum albumin, wherein the linker between the first and second ISVDs is preferably a 5GS linker, whereas the other linkers are preferably 9GS linkers.

Such configurations of the polypeptide can provide for strong potencies with regard to treating cancer as well as low binding to pre-existing antibodies.

Preferably, the multispecific-multivalent polypeptide exhibits reduced binding by pre-existing antibodies in human serum. To this end, in one embodiment, the polypeptide exhibits a valine (V) at amino acid position 11 and a leucine (L) at amino acid position 89 (according to Kabat numbering) in at least one ISVD (and preferably the ISVD at the C-terminal end of the polypeptide), but preferably in each ISVD. In another embodiment, the polypeptide exhibits an extension of 1 to 5 (preferably naturally occurring) amino acids, such as a single alanine (A) extension, at the C-terminus of the C-terminal ISVD. The C-terminus of an ISVD is normally VTVSS (SEQ ID NO: 116). In another embodiment, the polypeptide exhibits a lysine (K) or glutamine (Q) at position 110 (according to Kabat numbering) in at least one ISVD. In another embodiment, the ISVD exhibits a lysine (K) or glutamine (Q) at position 112 (according to Kabat numbering) in at least on ISVD. In these embodiments, the C-terminus of the ISVD is VKVSS (SEQ ID NO: 117), VQVSS (SEQ ID NO: 118), VTVKS (SEQ ID NO: 119), VTVQS (SEQ ID NO: 120), VKVKS (SEQ ID NO: 121), VKVQS (SEQ ID NO: 122), VQVKS (SEQ ID NO: 123), or VQVQS (SEQ ID NO: 124) such that after addition of a single alanine the C-terminus of the polypeptide for example exhibits the sequence VTVSSA (SEQ ID NO: 125), VKVSSA (SEQ ID NO: 126), VQVSSA (SEQ ID NO: 127), VTVKSA (SEQ ID NO: 128), VTVQSA (SEQ ID NO: 129), VKVKSA (SEQ ID NO: 130), VKVQSA (SEQ ID NO: 131), VQVKSA (SEQ ID NO: 132), or VQVQSA (SEQ ID NO: 133), preferably VTVSSA (see Table A-7). In another embodiment, the polypeptide exhibits a valine (V) at amino acid position 11 and a leucine (L) at amino acid position 89 (according to Kabat numbering) in at least the C-terminal ISVD, optionally a lysine (K) or glutamine (Q) at position 110 (according to Kabat numbering) in at least one ISVD, and exhibits an extension of 1 to 5 (preferably naturally occurring) amino acids, such as a single alanine (A) extension, at the C-terminus of the C-terminal ISVD (such that the C-terminus of the polypeptide for example consists of the sequence VTVSSA, VKVSSA or VQVSSA, preferably VTVSSA). See e.g. WO2012/175741 and WO2015/173325 for further information in this regard.

In a preferred embodiment, the multispecific-multivalent polypeptide comprises or consists of an amino acid sequence exhibiting a sequence identity of more than 90%, such as more than 95% or more than 99%, with SEQ ID NO: 1, wherein more preferably the CDRs of the four ISVDs are as defined in items A to D using the Abm definition (or A' to D' if using the Kabat definition) set forth in sections "5.2 Immunoglobulin single variable domains" and "5.4 (In vivo) half-life extension" below, respectively, wherein in particular:

- the first ISVD specifically binding to the constant domain of a TCR on a T cell comprises a CDR1 being the amino acid sequence of SEQ ID NO: 6, a CDR2 being the amino acid sequence of SEQ ID NO: 10 and a CDR3 being the amino acid sequence of SEQ ID NO: 14;
- the second ISVD specifically binding to GPC3 comprises a CDR1 being the amino acid sequence of SEQ ID NO: 7, a CDR2 being the amino acid sequence of SEQ ID NO: 11 and a CDR3 being the amino acid sequence of SEQ ID NO: 15;
- the third ISVD specifically binding to GPC3 comprises a CDR1 being the amino acid sequence of SEQ ID NO: 8, a CDR2 being the amino acid sequence of SEQ ID NO: 12 and a CDR3 being the amino acid sequence of GVA; and
- the fourth ISVD binding to human serum albumin comprises a CDR1 being the amino acid sequence of SEQ ID NO: 9, a CDR2 being the amino acid sequence of SEQ ID NO: 13 and a CDR3 being the amino acid sequence of SEQ ID NO: 17, or alternatively if using the Kabat definition:

- the first ISVD specifically binding to TCR comprises a CDR1 being the amino acid sequence of SEQ ID NO: 31, a CDR2 being the amino acid sequence of SEQ ID NO: 35 and a CDR3 being the amino acid sequence of SEQ ID NO: 14;
- the second ISVD specifically binding to GPC3 comprises a CDR1 being the amino acid sequence of SEQ ID NO: 32, a CDR2 being the amino acid sequence of SEQ ID NO: 36 and a CDR3 being the amino acid sequence of SEQ ID NO: 15;
- the third ISVD specifically binding to GPC3 comprises a CDR1 being the amino acid sequence of SEQ ID NO: 33, a CDR2 being the amino acid sequence of SEQ ID NO: 37 and a CDR3 being the amino acid sequence of GVA; and
- the fourth ISVD binding to human serum albumin comprises a CDR1 being the amino acid sequence of SEQ ID NO: 34, a CDR2 being the amino acid sequence of SEQ ID NO: 38 and a CDR3 being the amino acid sequence of SEQ ID NO: 17.

In some aspects, the polypeptide comprises or consists of an amino acid sequence selected from SEQ ID NOs: 1, 49-72 and 78-81.

Preferably, the polypeptide comprises or consists of the amino acid sequence of SEQ ID NO: 1 (see Table A-3). In a most preferred embodiment, the polypeptide consists of the amino acid sequence of SEQ ID NO: 1.

The polypeptide preferably exhibits at least half the binding affinity, more preferably at least the same binding affinity, to human TCR and to human GPC3 as compared to a polypeptide consisting of the amino acid of SEQ ID NO: 1 wherein the binding affinity is measured using the same method, such as Surface Plasmon Resonance (SPR).

5.2 Immunoglobulin Single Variable Domains

The term "immunoglobulin single variable domain" (ISVD), interchangeably used with "single variable domain", defines immunoglobulin molecules wherein the antigen binding site is present on, and formed by, a single immunoglobulin domain. This sets immunoglobulin single variable domains apart from "conventional" immunoglobulins (e.g. monoclonal antibodies) or their fragments (such as Fab, Fab', $F(ab')_2$, scFv, di-scFv), wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a $F(ab')_2$ fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single $V_H$, a single $V_{HH}$ or single $V_L$ domain.

As such, the single variable domain may be a light chain variable domain sequence (e.g., a $V_L$-sequence) or a suitable fragment thereof; or a heavy chain variable domain sequence (e.g., a $V_H$-sequence or $V_H$H sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

An immunoglobulin single variable domain (ISVD) can for example be a heavy chain ISVD, such as a $V_H$, $V_{HH}$, including a camelized $V_H$ or humanized $V_{HH}$. Preferably, it is a $V_{HH}$, including a camelized $V_H$ or humanized $V_{HH}$. Heavy chain ISVDs can be derived from a conventional four-chain antibody or from a heavy chain antibody.

For example, the immunoglobulin single variable domain may be a single domain antibody (or an amino acid sequence that is suitable for use as a single domain antibody), a "dAb" or dAb (or an amino acid sequence that is suitable for use as a dAb); other single variable domains, or any suitable fragment of any one thereof.

In particular, the immunoglobulin single variable domain may be an immunoglobulin single variable domain (such as a $V_{HH}$, including a humanized $V_{HH}$ or camelized $V_H$) or a suitable fragment thereof. Nanobody®, Nanobodies® and Nanoclone® are registered trademarks of Ablynx N.V.

"$V_{HH}$ domains", also known as $V_{HH}$S, $V_{HH}$ antibody fragments, and $V_{HH}$ antibodies, have originally been described as the antigen binding immunoglobulin variable domain of "heavy chain antibodies" (i.e., of "antibodies devoid of light chains"; Hamers-Casterman et al. Nature 363: 446-448, 1993). The term "$V_{HH}$ domain" has been chosen in order to distinguish these variable domains from the heavy chain variable domains that are present in conventional 4-chain antibodies (which are referred to herein as "$V_H$ domains") and from the light chain variable domains that are present in conventional 4-chain antibodies (which are referred to herein as "$V_L$ domains"). For a further description of $V_{HH}$'s, reference is made to the review article by Muyldermans (Reviews in Molecular Biotechnology 74: 277-302, 2001).

Typically, the generation of immunoglobulins involves the immunization of experimental animals, fusion of immunoglobulin producing cells to create hybridomas and screening for the desired specificities. Alternatively, immunoglobulins can be generated by screening of naïve or synthetic libraries e.g. by phage display.

The generation of immunoglobulin sequences has been described extensively in various publications, among which WO 94/04678, Hamers-Casterman et al. 1993 and Muyldermans et al. 2001 can be exemplified. In these methods, camelids are immunized with the target antigen in order to induce an immune response against said target antigen. The repertoire of VHHs obtained from said immunization is further screened for VHHs that bind the target antigen.

In these instances, the generation of antibodies requires purified antigen for immunization and/or screening. Antigens can be purified from natural sources, or in the course of recombinant production.

Immunization and/or screening for immunoglobulin sequences can be performed using peptide fragments of such antigens.

The present technology may use immunoglobulin sequences of different origin, comprising mouse, rat, rabbit, donkey, human and camelid immunoglobulin sequences. The technology also includes fully human, humanized or chimeric sequences. For example, the technology comprises camelid immunoglobulin sequences and humanized camelid immunoglobulin sequences, or camelized domain antibodies, e.g. camelized dAb as described by Ward et al (see for example WO 94/04678 and Davies and Riechmann (1994 and 1996)). Moreover, the technology also uses fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin sequences comprising tags or other functional moieties, e.g. toxins, labels, radiochemicals, etc., which are derivable from the immunoglobulin sequences of the present technology.

A "humanized $V_{HH}$" comprises an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art (e.g. WO 2008/020079). Again, it should be noted that such humanized $V_{HH}$S can be obtained in any suitable manner known per se and thus are not strictly limited to polypeptides that have been obtained using a polypeptide that comprises a naturally occurring VHH domain as a starting material.

A "camelized $V_H$" comprises an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein and the prior art (e.g. WO 2008/020079). Such "camelizing" substitutions are preferably inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). Preferably, the $V_H$ sequence that is used as a starting material or starting point for generating or designing the camelized $V_H$ is preferably a $V_H$ sequence from a mammal, more preferably the $V_H$ sequence of a human being, such as a $V_{H3}$ sequence. However, it should be noted that such camelized $V_H$ can be obtained in any suitable manner known per se and thus are not strictly limited to polypeptides that have been obtained using a polypeptide that comprises a naturally occurring $V_H$ domain as a starting material.

A preferred structure of an immunoglobulin single variable domain sequence can be considered to be comprised of four framework regions ("FRs"), which are referred to in the art and herein as "Framework region 1" ("FR1"); as "Framework region 2" ("FR2"); as "Framework region 3" ("FR3"); and as "Framework region 4" ("FR4"), respectively; which framework regions are interrupted by three complementary determining regions ("CDRs"), which are referred to in the art and herein as "Complementarity Determining Region 1" ("CDR1"); as "Complementarity Determining Region 2" ("CDR2"); and as "Complementarity Determining Region 3" ("CDR3"), respectively.

As further described in paragraph q) on pages 58 and 59 of WO 08/020079, the amino acid residues of an immunoglobulin single variable domain can be numbered according to the general numbering for $V_H$ domains given by Kabat et al. ("Sequence of proteins of immunological interest", US Public Health Services, NIH Bethesda, MD, Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for $V_H$H domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a $V_H$ domain and a $V_{HH}$ domain will usually be in the range of from 110 to 120, often between 112 and 115. It should however be noted that smaller and longer sequences may also be suitable for the purposes described herein.

In the present application, unless indicated otherwise, CDR sequences were determined according to the AbM definition as described in Kontermann and Dobel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Determination of CDR regions may also be done according to different methods. In the CDR determination according to Kabat, FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

In such an immunoglobulin sequence, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence or $V_{HH}$ sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

In particular, the framework sequences present in the ISVD sequence used in the technology may contain one or more of hallmark residues (as defined herein), such that the ISVD sequence is a $V_{HH}$, including a humanized $V_{HH}$ or camelized $V_H$. Some preferred, but non-limiting examples of (suitable combinations of) such framework sequences will become clear from the further disclosure herein.

Again, as generally described herein for the immunoglobulin sequences, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived).

However, it should be noted that the technology is not limited as to the origin of the ISVD sequence (or of the nucleotide sequence used to express it), nor as to the way that the ISVD sequence or nucleotide sequence is (or has been) generated or obtained. Thus, the ISVD sequences may be naturally occurring sequences (from any suitable species) or synthetic or semi-synthetic sequences. In a specific but non-limiting aspect, the ISVD sequence is a naturally occurring sequence (from any suitable species) or a synthetic or semi-synthetic sequence, including but not limited to "humanized" (as defined herein) immunoglobulin sequences (such as partially or fully humanized mouse or rabbit immunoglobulin sequences, and in particular partially or fully humanized $V_{HH}$ sequences), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

Similarly, nucleotide sequences may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

As described above, an ISVD may be a Nanobody® or a suitable fragment thereof. For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_{H3}$ class such as DP-47, DP-51 or DP-29). It should however be noted that the technology in its broadest sense can generally use any type of Nanobody, and for example also uses the Nanobodies belonging to the so-called "$V_H4$ class" (i.e. Nanobodies with a high degree of sequence homology to human germline sequences of the $V_{H4}$ class such as DP-78), as for example described in WO 2007/118670.

Generally, Nanobodies (in particular $V_{HH}$ sequences, including (partially) humanized $V_{HH}$ sequences and camelized $V_H$ sequences) can be characterized by the presence of one or more "Hallmark residues" (as described herein) in one or more of the framework sequences (again as further described herein). Thus, generally, a Nanobody can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

one or more of the amino acid residues at positions 11, 37, 44, 45, 47, 83, 84, 103, 104 and 108 according to the Kabat numbering are chosen from the Hallmark residues mentioned in Table A-0 below.

TABLE A-0

Hallmark Residues in Nanobodies

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | F[(1)], Y, V, L, A, H, S, I, W, C, N, G, D, T, P, preferably F[(1)] or Y |
| 44[(8)] | G | E[(3)], Q[(3)], G[(2)], D, A, K, R, L, P, S, V, H, T, N, W, M, I; preferably G[(2)], E[(3)] or Q[(3)]; most preferably G[(2)] or Q[(3)]. |
| 45[(8)] | L | L[(2)], R[(3)], P, H, F, G, Q, S, E, T, Y, C, I, D, V; preferably L[(2)] or R[(3)] |
| 47[(8)] | W, Y | F[(1)], L[(1)] or W[(2)] G, I, S, A, V, M, R, Y, E, P, T, C, H, K, Q, N, D; preferably W[(2)], L[(1)] or F[(1)] |
| 83 | R or K; usually R | R, K[(5)], T, E[(5)], Q, N, S, I, V, G, M, L, A, D, Y, H; preferably K or R; most preferably K |

TABLE A-0-continued

| Hallmark Residues in Nanobodies | | |
|---|---|---|
| Position | Human $V_H3$ | Hallmark Residues |
| 84 | A, T, D; predominantly A | P[5], S, H, L, A, V, I, T, F, D, R, Y, N, Q, G, E; preferably P |
| 103 | W | W[4], R[6], G, S, K, A, M, Y, L, F, T, N, V, Q, P[6], E, C; preferably W |
| 104 | G | G, A, S, T, D, P, N, E, C, L; preferably G |
| 108 | L, M or T; predominantly L | Q, L[7], R, P, E, K, S, T, M, A, H; preferably Q or L[7] |

Notes:

(1)In particular, but not exclusively, in combination with KERE or KQRE at positions 43-46.

(2)Usually as GLEW at positions 44-47.

(3)Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.

(4)With both GLEW at positions 44-47 and KERE or KQRE at positions 43-46.

(5)Often as KP or EP at positions 83-84 of naturally occurring $V_{HH}$ domains.

(6)In particular, but not exclusively, in combination with GLEW at positions 44-47.

(7)With the proviso that when positions 44-47 are GLEW, position 108 is always Q in (non-humanized) $V_{HH}$ sequences that also contain a W at 103.

(8)The GLEW group also contains GLEW-like sequences at positions 44-47, such as for example GVEW, EPEW, GLER, DQEW, DLEW, GIEW, ELEW, GPEW, EWLP, GPER, GLER and ELEW.

The technology inter alia uses ISVDs that can bind to the constant domain of a TCR or GPC3. In the context of the present technology, "binding to" a certain target molecule has the usual meaning in the art as understood in the context of antibodies and their respective antigens.

The multispecific-multivalent polypeptide may comprise one or more ISVDs specifically binding to GPC3. For example, the polypeptide may comprise two ISVDs that specifically bind to GPC3 and an ISVD that specifically binds to TCR.

The ISVDs used in the technology can form part of a polypeptide, which comprises or consists of at least two ISVDs, such that the polypeptide can specifically bind to GPC3 and TCR.

Accordingly, the target molecules of the ISVDs used in the technology are GPC3 and the constant domain of the TCR, respectively. Binding to TCR can be achieved, for example, by binding to the TCRalpha subunit and/or the TCR beta subunit. Examples are mammalian GPC3 and TCR. While human GPC3 (Uniprot accession P51654, see Table A-8) and human TCR (see Table A-8) are preferred, the versions from other species are also amenable to the present technology, for example GPC3 and TCR from mice, rats, rabbits, cats, dogs, goats, sheep, horses, pigs, non-human primates, such as cynomolgus monkeys (also referred to herein as "cyno"), or camelids, such as llama or alpaca.

Specific examples of ISVDs specifically binding to the constant domain of a TCR on a T cell that can be used in the technology are as described in the following item A:

A. An ISVD that specifically binds to human TCR and comprises
   i. a CDR1 that is the amino acid sequence of SEQ ID NO: 6 or an amino acid sequence with 2 or 1 amino acid difference(s) with SEQ ID NO: 6;
   ii. a CDR2 that is the amino acid sequence of SEQ ID NO: 10 or an amino acid sequence with 2 or 1 amino acid difference(s) with SEQ ID NO: 10; and
   iii. a CDR3 that is the amino acid sequence of SEQ ID NO: 14 or an amino acid sequence with 2 or 1 amino acid difference(s) with SEQ ID NO: 14,
   preferably a CDR1 being the amino acid sequence of SEQ ID NO: 6, a CDR2 being the amino acid sequence of SEQ ID NO: 10 and a CDR3 being the amino acid sequence of SEQ ID NO: 14.

In a preferred embodiment, the ISVD binds to the constant domain of a human TCR-α of SEQ ID NO: 135 and/or of a TCR-3 of SEQ ID NO: 136, or polymorphic variants or isoforms thereof.

Preferred examples of such an ISVD that specifically binds to human TCR comprise one or more (and preferably all) framework regions as indicated for ISVD TCE01 in Table A-2 (in addition to the CDRs as defined in the preceding item A), and most preferred is an ISVD that consists of the full amino acid sequence of ISVD TCE01 (SEQ ID NO: 2; see Table A-1 and A-2).

Also, in a preferred embodiment, the amino acid sequence of the ISVD specifically binding to human TCR may exhibit a sequence identity of more than 90%, such as more than 95% or more than 99%, with SEQ ID NO: 2, wherein the CDRs are as defined in the preceding item A. In particular, the ISVD specifically binding to TCR most preferably is the amino acid sequence of SEQ ID NO: 2.

When such an ISVD binding to TCR exhibits 2 or 1 amino acid difference in at least one CDR relative to a corresponding reference CDR sequence (item A above), the ISVD preferably exhibits at least half the binding affinity, more preferably at least the same binding affinity to human TCR as the construct TCE01 set forth in SEQ ID NO: 2, wherein the binding affinity is measured using the same method, such as SPR.

Specific examples of ISVDs-specifically binding to GPC3 that can be used in the technology are as described in the following items B and C:

B. An ISVD that specifically binds to human GPC3 and comprises
   i. a CDR1 that is the amino acid sequence of SEQ ID NO: 7 or an amino acid sequence with 2 or 1 amino acid difference(s) with SEQ ID NO: 7;
   ii. a CDR2 that is the amino acid sequence of SEQ ID NO: 11 or an amino acid sequence with 2 or 1 amino acid difference(s) with SEQ ID NO: 11; and
   iii. a CDR3 that is the amino acid sequence of SEQ ID NO: 15 or an amino acid sequence with 2 or 1 amino acid difference(s) with SEQ ID NO: 15,
   preferably a CDR1 being the amino acid sequence of SEQ ID NO: 7, a CDR2 being the amino acid sequence of SEQ ID NO: 11 and a CDR3 being the amino acid sequence of SEQ ID NO: 15.

C. An ISVD that specifically binds to human GPC3 and comprises
   i. a CDR1 that is the amino acid sequence of SEQ ID NO: 8 or an amino acid sequence with 2 or 1 amino acid difference(s) with SEQ ID NO: 8;
   ii. a CDR2 that is the amino acid sequence of SEQ ID NO: 12 or an amino acid sequence with 2 or 1 amino acid difference(s) with SEQ ID NO: 12; and
   iii. a CDR3 that is the amino acid sequence of GVA or an amino acid sequence with 2 or 1 amino acid difference(s) with GVA,
   preferably a CDR1 being the amino acid sequence of SEQ ID NO: 8, a CDR2 being the amino acid sequence of SEQ ID NO: 12 and a CDR3 being the amino acid sequence of GVA.

In a preferred embodiment, the ISVD binds to human GPC3 of SEQ ID NO: 134.

Preferred examples of such an ISVD that specifically binds to human GPC3 comprise one or more (and preferably all) framework regions as indicated for ISVD A022600351 and A022600314, respectively, in Table A-2 (in addition to the CDRs as defined in the preceding items B and C, respectively), and most preferred is an ISVD that consists of the full amino acid sequence of ISVD A022600351 or A022600314 (SEQ ID NOs: 3 or 4, see Table A-1 and A-2).

Also, in a preferred embodiment, the amino acid sequence of an ISVD(s) specifically binding to human GPC3 may exhibit a sequence identity of more than 90%, such as more than 95% or more than 99%, with SEQ ID NO: 3 or 4, respectively, wherein the CDRs are as defined in the preceding item B or C, respectively. In particular, the ISVD binding to human GPC3 most preferably is the amino acid sequence of SEQ ID NOs: 3 or 4.

When such an ISVD binding to human GPC3 exhibits 2 or 1 amino acid difference in at least one CDR relative to a corresponding reference CDR sequence (item B or C above), the ISVD preferably exhibits at least half the binding affinity, more preferably at least the same binding affinity to human GPC3 as construct A022600351 or A022600314 set forth in SEQ ID NO: 3 and 4, respectively, wherein the binding affinity is measured using the same method, such as SPR.

Preferably, each of the ISVDs as defined under items A to C above is comprised in the polypeptide.

Such a polypeptide comprising each of the ISVDs as defined under items A to C above preferably exhibits at least half the binding affinity, more preferably at least the same binding affinity, to human TCR and to human GPC3 as a polypeptide consisting of the amino acid of SEQ ID NO: 1, wherein the binding affinity is measured using the same method, such as SPR.

The SEQ ID NOs referred to in the above items A to C and item D below (see section 5.4 "(In vivo) half-life extension") are based on the CDR definition according to the AbM definition (see Table A-2). It is noted that the SEQ ID NOs defining the same CDRs according to the Kabat definition (see Table A-2-1) can likewise be used in the above items A to C and item D below (see section 5.4 "(In vivo) half-life extension").

Accordingly, the specific examples of ISVDs specifically binding to the constant domain of a TCR on a T cell or GPC3 that can be used in the technology are as described above using the AbM definition can be also described using the Kabat definition as set forth in items A' to C' below:

A'. An ISVD that specifically binds to human TCR and comprises
   i. a CDR1 that is the amino acid sequence of SEQ ID NO: 31 or an amino acid sequence with 2 or 1 amino acid difference(s) with SEQ ID NO: 31;
   ii. a CDR2 that is the amino acid sequence of SEQ ID NO: 35 or an amino acid sequence with 2 or 1 amino acid difference(s) with SEQ ID NO: 35; and
   iii. a CDR3 that is the amino acid sequence of SEQ ID NO: 14 or an amino acid sequence with 2 or 1 amino acid difference(s) with SEQ ID NO: 14,
   preferably a CDR1 being the amino acid sequence of SEQ ID NO: 31, a CDR2 being the amino acid sequence of SEQ ID NO: 35 and a CDR3 being the amino acid sequence of SEQ ID NO: 14.

Preferred examples of such an ISVD that specifically binds to human TCR comprise one or more (and preferably all) framework regions as indicated for ISVD TCE01, respectively, in Table A-2-1 (in addition to the CDRs as defined in the preceding item A'), and most preferred is an ISVD that consists of the full amino acid sequence of ISVD TCE01 (SEQ ID NO: 2; see Table A-1 and A-2-1).

B'. An ISVD that specifically-binds to human GPC3 and comprises
   i. a CDR1 that is the amino acid sequence of SEQ ID NO: 32 or an amino acid sequence with 2 or 1 amino acid difference(s) with SEQ ID NO: 32;
   ii. a CDR2 that is the amino acid sequence of SEQ ID NO: 36 or an amino acid sequence with 2 or 1 amino acid difference(s) with SEQ ID NO: 36; and
   iii. a CDR3 that is the amino acid sequence of SEQ ID NO: 15 or an amino acid sequence with 2 or 1 amino acid difference(s) with SEQ ID NO: 15,
   preferably a CDR1 being the amino acid sequence of SEQ ID NO: 32, a CDR2 being the amino acid sequence of SEQ ID NO: 36 and a CDR3 being the amino acid sequence of SEQ ID NO: 15.

C'. An ISVD that specifically binds to human GPC3 and comprises
   i. a CDR1 that is the amino acid sequence of SEQ ID NO: 33 or an amino acid sequence with 2 or 1 amino acid difference(s) with SEQ ID NO: 33;
   ii. a CDR2 that is the amino acid sequence of SEQ ID NO: 37 or an amino acid sequence with 2 or 1 amino acid difference(s) with SEQ ID NO: 37; and
   iii. a CDR3 that is the amino acid sequence of GVA or an amino acid sequence with 2 or 1 amino acid difference(s) with GVA,
   preferably a CDR1 being the amino acid sequence of SEQ ID NO: 33, a CDR2 being the amino acid sequence of SEQ ID NO: 37 and a CDR3 being the amino acid sequence of GVA.

Preferred examples of such an ISVD(s) that specifically binds to human GPC3 comprise one or more (and preferably all) framework regions as indicated for ISVD A022600351 and A022600314, respectively, in Table A-2-1 (in addition to the CDRs as defined in the preceding items B' and C', respectively), and most preferred is an ISVD that consists of the full amino acid sequence of ISVD A022600351 or A022600314 (SEQ ID NOs: 3 or 4, see Table A-1 and A-2-1).

The percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (i.e. at a single position).

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

An "amino acid difference" as used herein refers to a deletion, insertion or substitution of a single amino acid residue vis-à-vis a reference sequence, and preferably is a substitution.

Amino acid substitutions are preferably conservative substitutions. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

5.3 Specificity

The terms "specificity", "binding specifically" or "specific binding" refer to the number of different target molecules, such as antigens, from the same organism to which a particular binding unit, such as an ISVD, can bind with sufficiently high affinity (see below). "Specificity", "binding specifically" or "specific binding" are used interchangeably herein with "selectivity", "binding selectively" or "selective binding". Binding units, such as ISVDs, preferably specifically bind to their designated targets.

The specificity/selectivity of a binding unit can be determined based on affinity. The affinity denotes the strength or stability of a molecular interaction. The affinity is commonly given as by the KD, or dissociation constant, which is expressed in units of mol/liter (or M). The affinity can also be expressed as an association constant, KA, which equals 1/KD and is expressed in units of $(\text{mol/liter})^{-1}$ (or $M^{-1}$).

The affinity is a measure for the binding strength between a moiety and a binding site on the target molecule: the lower the value of the KD, the stronger the binding strength between a target molecule and a targeting moiety.

Typically, binding units used in the present technology (such as ISVDs) will bind to their targets with a dissociation constant (KD) of $10^{-5}$ to $10^{-12}$ moles/liter or less, and preferably $10^{-1}$ to $10^{-12}$ moles/liter or less and more preferably $10^{-8}$ to $10^{-12}$ moles/liter (i.e. with an association constant (KA) of $10^{5}$ to $10^{12}$ liter/moles or more, and preferably $10^{7}$ to $10^{12}$ liter/moles or more and more preferably $10^{8}$ to $10^{12}$ liter/moles).

Any KD value greater than $10^{-4}$ mol/liter (or any KA value lower than $10^{4}$ liters/mol) is generally considered to indicate non-specific binding.

The KD for biological interactions, such as the binding of immunoglobulin sequences to an antigen, which are considered specific are typically in the range of $10^{-5}$ moles/liter (10000 nM or 10 μM) to $10^{-12}$ moles/liter (0.001 nM or 1 pM) or less.

Accordingly, specific/selective binding may mean that—using the same measurement method, e.g. SPR—a binding unit (or polypeptide comprising the same) binds to TCR and/or GPC3 with a KD value of $10^{-5}$ to $10^{12}$ moles/liter or less and binds to related targets with a KD value greater than $10^{-4}$ moles/liter. Examples of related targets for GPC3 are GPC1, GPC2, GPC4, GPC5 or GPC6. Thus, in an embodiment of the technology, the ISVDs comprised in the polypeptide that bind to GPC3, bind to GPC3 with a KD value of $10^{-5}$ to $10^{-12}$ moles/liter or less and bind to GPC1, GPC2, GPC4, GPC5 and GPC6 of the same species with a KD value greater than $10^{-4}$ moles/liter.

Thus, the polypeptide preferably exhibits at least half the binding affinity, more preferably at least the same binding affinity, to human TCR and to human GPC3 as compared to a polypeptide consisting of the amino acid of SEQ ID NO: 1, wherein the binding affinity is measured using the same method, such as SPR.

Specific binding to a certain target from a certain species does not exclude that the binding unit can also specifically bind to the analogous target from a different species. For example, specific binding to human TCR does not exclude that the binding unit (or a polypeptide comprising the same) can also specifically bind to TCR from cynomolgus monkeys. Likewise, for example, specific binding to human GPC3 does not exclude that the binding unit (or a polypeptide comprising the same) can also specifically bind to GPC3 from cynomolgus monkeys ("cyno").

The ISVD with SEQ ID NO: 2 that binds to human TCR and that is comprised in the polypeptides of the current technology, exhibits improved binding characteristics compared to ISVD T0170056G05, which is described in WO 2016/180969 A1. More specifically, the ISVD with SEQ ID NO:2 is derived from T017056G05 and comprises specific mutations in CDR1 and CDR3 which result in improved cross-reactivity for binding to human and non-human primate (such as cynomolgus monkey) TCR compared to ISVD T0170056G05.

When an ISVD is said to exhibit "improved cross-reactivity for binding to human and non-human primate TCR" compared to another ISVD, it means that for said ISVD the ratio of the binding activity (such as expressed in terms of KD or $k_{off}$) for human TCR and for non-human primate TCR is lower than that same ratio calculated for the other ISVD in the same assay.

Good cross-reactivity for binding to human and non-human primate TCR allows for the assessment of toxicity of a multispecific T cell engaging polypeptide in preclinical studies conducted on non-human primates.

Specific binding of a binding unit to its designated target can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned below. In this respect, it will also be clear that it may not be possible to measure dissociation constants of more than $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity of a molecular interaction between two molecules can be measured via different techniques known perse, such as the well-known surface plasmon resonance (SPR) biosensor technique (see for example Ober et al. 2001, Intern. Immunology 13: 1551-1559). The term “surface plasmon resonance”, as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ). For further descriptions, see Jonsson et al. (1993, Ann. Biol. Clin. 51: 19-26), Jonsson et al. (1991 Biotechniques 11: 620-627), Johnsson et al. (1995, J. Mol. Recognit. 8: 125-131), and Johnnson et al. (1991, Anal. Biochem. 198: 268-277).

Another well-known biosensor technique to determine affinities of biomolecular interactions is bio-layer interferometry (BLI) (see for example Abdiche et al. 2008, Anal. Biochem. 377: 209-217). The term “bio-layer Interferometry” or “BLI”, as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term “KinExA”, as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

The GYROLAB® immunoassay system provides a platform for automated bioanalysis and rapid sample turnaround (Fraley et al. 2013, Bioanalysis 5: 1765-74).

5.4 (In Vivo) Half-Life Extension

The polypeptide may further comprise one or more other groups, residues, moieties or binding units, optionally linked via one or more peptidic linkers, in which said one or more other groups, residues, moieties or binding units provide the polypeptide with increased (in vivo) half-life, compared to the corresponding polypeptide without said one or more other groups, residues, moieties or binding units. In vivo half-life extension means, for example, that the polypeptide exhibits an increased half-life in a mammal, such as a human subject, after administration. Half-life can be expressed for example as t½beta.

The type of groups, residues, moieties or binding units is not generally restricted and may for example be chosen from the group consisting of a polyethylene glycol molecule, serum proteins or fragments thereof, binding units that can bind to serum proteins, an Fc portion, and small proteins or peptides that can bind to serum proteins.

More specifically, said one or more other groups, residues, moieties or binding units that provide the polypeptide with increased half-life can be chosen from the group consisting of binding units that can bind to serum albumin, such as human serum albumin, or a serum immunoglobulin, such as IgG, and preferably is a binding unit that can bind to human serum albumin. The binding unit is preferably an ISVD.

For example, WO 04/041865 describes Nanobodies® binding to serum albumin (and in particular against human serum albumin) that can be linked to other proteins (such as one or more other Nanobodies binding to a desired target) in order to increase the half-life of said protein.

The international application WO 06/122787 describes a number of Nanobodies® against (human) serum albumin. These Nanobodies® include the Nanobody® called Alb-1 (SEQ ID NO: 52 in WO 06/122787) and humanized variants thereof, such as Alb-8 (SEQ ID NO: 62 in WO 06/122787). Again, these can be used to extend the half-life of therapeutic proteins and polypeptide and other therapeutic entities or moieties.

Moreover, WO2012/175400 describes a further improved version of Alb-1, called Alb-23.

In a preferred embodiment, the polypeptide comprises a serum albumin binding moiety selected from Alb-1, Alb-3, Alb-4, Alb-5, Alb-6, Alb-7, Alb-8, Alb-9, Alb-10 and Alb-23, preferably Alb-8 or Alb-23 or its variants, as shown in pages 7-9 of WO2012/175400 and the albumin binders described in WO 2012/175741, WO2015/173325, WO2017/080850, WO2017/085172, WO2018/104444, WO2018/134235, WO2018/134234. Some preferred serum albumin binders are also shown in Table A-4. A particularly preferred further component of the polypeptide is as described in item D:

D. An ISVD that binds to human serum albumin and comprises
   i. a CDR1 that is the amino acid sequence of SEQ ID NO: 9 or an amino acid sequence with 2 or 1 amino acid difference(s) with SEQ ID NO: 9;
   ii. a CDR2 that is the amino acid sequence of SEQ ID NO: 13 or an amino acid sequence with 2 or 1 amino acid difference(s) with SEQ ID NO: 13; and
   iii. a CDR3 that is the amino acid sequence of SEQ ID NO: 17 or an amino acid sequence with 2 or 1 amino acid difference(s) with SEQ ID NO: 17;

preferably a CDR1 being the amino acid sequence of SEQ ID NO: 9, a CDR2 being the amino acid sequence of SEQ ID NO: 13 and a CDR3 being the amino acid sequence of SEQ ID NO: 17.

Preferred examples of such an ISVD that binds to human serum albumin comprise one or more (and preferably all) framework regions as indicated for ISVD ALB23002 in Table A-2 (in addition to the CDRs as defined in the preceding item D), and most preferred is an ISVD that consists of the full amino acid sequence of ISVD ALB23002 (SEQ ID NO: 5, see Table A-1 and A-2).

Item D can be also described using the Kabat definition as:

D'. An ISVD that binds to human serum albumin and comprises
   i. a CDR1 that is the amino acid sequence of SEQ ID NO: 34 or an amino acid sequence with 2 or 1 amino acid difference(s) with SEQ ID NO: 34;
   ii. a CDR2 that is the amino acid sequence of SEQ ID NO: 38 or an amino acid sequence with 2 or 1 amino acid difference(s) with SEQ ID NO: 38; and
   iii. a CDR3 that is the amino acid sequence of SEQ ID NO: 17 or an amino acid sequence with 2 or 1 amino acid difference(s) with SEQ ID NO: 17;
   preferably a CDR1 being the amino acid sequence of SEQ ID NO: 34, a CDR2 being the amino acid sequence of SEQ ID NO: 38 and a CDR3 being the amino acid sequence of SEQ ID NO: 17.

Preferred examples of such an ISVD that binds to human serum albumin comprise one or more (and preferably all) framework regions as indicated for ISVD ALB23002 in Table A-2-1 (in addition to the CDRs as defined in the preceding item D'), and most preferred is an ISVD consists of the full amino acid sequence of ISVD ALB23002 (SEQ ID NO: 5, see Table A-1 and A-2-1).

Also, in a preferred embodiment, the amino acid sequence of an ISVD binding to human serum albumin may exhibit a sequence identity of more than 90%, such as more than 95% or more than 99%, with SEQ ID NO: 5, wherein the CDRs are as defined in the preceding item D or D'. In particular, the ISVD binding to human serum albumin preferably is the amino acid sequence of SEQ ID NO: 5.

When such an ISVD binding to human serum albumin exhibits 2 or 1 amino acid difference in at least one CDR relative to a corresponding reference CDR sequence (item D or D' above), the ISVD exhibits at least half the binding affinity, preferably at least the same binding affinity to human serum albumin as construct ALB23002 set forth in SEQ ID NO: 5, wherein the binding affinity is measured using the same method, such as SPR.

When such an ISVD binding to human serum albumin is at a C-terminal position it can exhibit a C-terminal alanine (A) or glycine (G) extension (preferably A) and is preferably selected from SEQ ID NOs: 83, 85, 87, 89, 91, 93, 95, 96 and 98, most preferably SEQ ID NO: 96, which represents SEQ ID NO: 5 with a single alanine extension (see table A-4 below). In some embodiments, the ISVD binding to human serum albumin is at another position than the C-terminal position (i.e. is not the C-terminal ISVD of the polypeptide) and is selected from SEQ ID NOs: 5, 82, 84, 86, 88, 90, 92, 94 and 97 (see table A-4 below).

5.5 Nucleic Acid Molecules

Also provided is a nucleic acid molecule encoding the polypeptide as disclosed herein.

A "nucleic acid molecule" (used interchangeably with "nucleic acid") is a chain of nucleotide monomers linked to each other via a phosphate backbone to form a nucleotide sequence. A nucleic acid may be used to transform/transfect a host cell or host organism, e.g. for expression and/or production of a polypeptide. Suitable hosts or host cells for production purposes will be clear to the skilled person, and may for example be any suitable fungal, prokaryotic or eukaryotic cell or cell line or any suitable fungal, prokaryotic or eukaryotic organism. A host or host cell comprising a nucleic acid encoding the polypeptide is also encompassed by the technology.

A nucleic acid may be for example DNA, RNA, or a hybrid thereof, and may also comprise (e.g. chemically) modified nucleotides, like PNA. It can be single- or double-stranded, and is preferably in the form of double-stranded DNA. For example, the nucleotide sequences may be genomic DNA or cDNA.

The nucleic acids can be prepared or obtained in a manner known per se, and/or can be isolated from a suitable natural source. Nucleotide sequences encoding naturally occurring (poly)peptides can for example be subjected to site-directed mutagenesis, so as to provide a nucleic acid molecule encoding polypeptide with sequence variation. Also, as will be clear to the skilled person, to prepare a nucleic acid, also several nucleotide sequences, such as at least one nucleotide sequence encoding a targeting moiety and for example nucleic acids encoding one or more linkers can be linked together in a suitable manner.

Techniques for generating nucleic acids will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers.

5.6 Vectors

Also provided is a vector comprising the nucleic acid molecule encoding the polypeptide as disclosed herein. A vector as used herein is a vehicle suitable for carrying genetic material into a cell. A vector includes naked nucleic acids, such as plasmids or mRNAs, or nucleic acids embedded into a bigger structure, such as liposomes or viral vectors.

Vectors generally comprise at least one nucleic acid that is optionally linked to one or more regulatory elements, such as for example one or more suitable promoter(s), enhancer(s), terminator(s), etc.). The vector preferably is an expression vector, i.e. a vector suitable for expressing an encoded polypeptide or construct under suitable conditions, e.g. when the vector is introduced into a (e.g. human) cell. For DNA-based vectors, this usually includes the presence of elements for transcription (e.g. a promoter and a polyA signal) and translation (e.g. Kozak sequence).

Preferably, in the vector, said at least one nucleic acid and said regulatory elements are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

Preferably, any regulatory elements of the vector are such that they are capable of providing their intended biological function in the intended host cell or host organism.

For instance, a promoter, enhancer or terminator should be "operable" in the intended host cell or host organism, by which is meant that for example said promoter should be capable of initiating or otherwise controlling/regulating the transcription and/or the expression of a nucleotide sequence—e.g. a coding sequence—to which it is operably linked.

5.7 Compositions

The technology also provides a composition comprising at least one polypeptide as disclosed herein, at least one nucleic acid molecule encoding a polypeptide as disclosed herein or at least one vector comprising such a nucleic acid molecule. The composition may be a pharmaceutical composition. The composition may further comprise at least one pharmaceutically acceptable carrier, diluent or excipient and/or adjuvant, and optionally comprise one or more further pharmaceutically active polypeptides and/or compounds.

5.8 Host Organisms

The technology also pertains to host cells or host organisms comprising the polypeptide as disclosed herein, the nucleic acid encoding the polypeptide as disclosed herein, and/or the vector comprising the nucleic acid molecule encoding the polypeptide as disclosed herein.

Suitable host cells or host organisms are clear to the skilled person, and are for example any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. The most preferred host is *Pichia pastoris*.

5.9 Methods and Uses of the Polypeptide

The technology also provides a method for producing the polypeptide as disclosed herein. The method may comprise transforming/transfecting a host cell or host organism with a nucleic acid encoding the polypeptide, expressing the polypeptide in the host, optionally followed by one or more isolation and/or purification steps. Specifically, the method may comprise:

a) expressing, in a suitable host cell or host organism or in another suitable expression system, a nucleic acid sequence encoding the polypeptide; optionally followed by:
b) isolating and/or purifying the polypeptide.

Suitable host cells or host organisms for production purposes will be clear to the skilled person, and may for example be any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. The most preferred host is *Pichia pastoris*.

The polypeptide, a nucleic acid molecule or vector as described, or a composition comprising the polypeptide, nucleic acid molecule or vector—preferably the polypeptide or a composition comprising the same—are useful as a medicament.

Accordingly, the technology provides the polypeptide, nucleic acid molecule or vector as described, or a composition comprising the polypeptide, nucleic acid molecule or vector for use as a medicament.

Also provided is the polypeptide, nucleic acid molecule or vector as described, or a composition comprising the polypeptide, nucleic acid molecule or vector for use in the treatment of cancer.

Further provided is a method of treating cancer, wherein said method comprises administering, to a subject in need thereof, a pharmaceutically active amount of the polypeptide, nucleic acid molecule or vector as described, or a composition comprising the polypeptide, nucleic acid molecule or vector.

Further provided is the use of the polypeptide, nucleic acid molecule or vector as described, or a composition comprising the polypeptide, nucleic acid molecule or vector in the preparation of a medicament.

Further provided is the use of the polypeptide, nucleic acid molecule or vector as described, or a composition comprising the polypeptide, nucleic acid molecule or vector in the preparation of a pharmaceutical composition, preferably for treating cancer.

The cancer can be any type of GPC3 expressing cancer. The cancer preferably is liver cancer or lung cancer, preferably liver cancer. Liver cancer is preferably hepatocellular carcinoma. Lung cancer is preferably non-small cell lung cancer (NSCLC), most preferably squamous cell carcinoma (SCC).

Preferably, the GPC3 expressing cancer cells express (on average) at least half the amount of GPC3 protein, preferably at least the same amount of GPC3 protein as Huh7 cells (on average). Huh7 cells are publicly available from e.g. the National Institutes of Biomedical Innovation, Health and Nutrition, JCRB Cell Bank, under accession number JCRB0403.

The expressed GPC3 preferably refers to cell surface-exposed GPC3. The expression of (cell surface-exposed) GPC3 on a cell (and the amount thereof) can be readily determined by routine methods commonly known in the art, such as flow cytometry, immunohistochemistry or as described in the examples.

A "subject" as referred to in the context of the technology can be any animal, preferably a mammal. Among mammals, a distinction can be made between humans and non-human mammals. Non-human animals may be for example companion animals (e.g. dogs, cats), livestock (e.g. bovine, equine, ovine, caprine, or porcine animals), or animals used generally for research purposes and/or for producing antibodies (e.g. mice, rats, rabbits, cats, dogs, goats, sheep, horses, pigs, non-human primates, such as cynomolgus monkeys, or camelids, such as llama or alpaca).

In the context of prophylactic and/or therapeutic purposes, the subject can be any animal, and more specifically any mammal, but preferably is a human subject.

Substances (including polypeptides, nucleic acid molecules and vectors) or compositions may be administered to a subject by any suitable route of administration, for example by enteral (such as oral or rectal) or parenteral (such as epicutaneous, sublingual, buccal, nasal, intra-articular, intradermal, intramuscular, intraperitoneal, intravenous, subcutaneous, transdermal, or transmucosal) administration. Parenteral administration, such as intramuscular, subcutaneous or intradermal, administration is preferred. Most preferred is subcutaneous administration.

An effective amount of a polypeptide, a nucleic acid molecule or vector as described, or a composition comprising the polypeptide, nucleic acid molecule or vector can be administered to a subject in order to provide the intended treatment results.

One or more doses can be administered. If more than one dose is administered, the doses can be administered in suitable intervals in order to maximize the effect of the polypeptide, composition, nucleic acid molecule or vector.

TABLE A-1

Amino acid sequences of the different monovalent ISVD building blocks identified within the pentavalent polypeptide A022600424 ("ID" refers to the SEQ ID NO as used herein)

| Name | ID | Amino acid sequence |
|---|---|---|
| TCE01 | 2 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSS |
| A022600351* | 3 | EVQLVESGGGVVQPGGSLRLSCAASGFTFSSFAMTWVRRPPGKGLEWVA TITNKGVTSYADSVKGRFTISRDNAKNTLYLQMNSLRPEDTALYICANARRT GPRAPTDIGSYRGQGTLVTVSS |
| A022600314° | 4 | EVQLVESGGGVVQPGGSLRLSCAASGSIFRSVFSSSTMEWYRQAPGKKREL VARIAPGEGTYYGALYADSVKGRFTISRDNAKNTVYLQMNSLRPEDTALYY CASGVAWGQGTLVTVSS |
| ALB23002 | 5 | EVQLVESGGGVVQPGGSLRLSCAASGFTFRSFGMSWVRQAPGKGPEWVS SISGSGSDTLYADSVKGRFTISRDNSKNTLYLQMNSLRPEDTALYYCTIGGSL SRSSQGTLVTVSS |

*Sequence optimized variant of A02260018C08 (SEQ ID NO: 48)
°Sequence optimized variant of A02260015A08 (SEQ ID NO: 47)

TABLE A-2

Sequences for CDRs and frameworks ("ID" refers to the given SEQ ID NO)

| ID | ISVD | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | TCE01 | 18 | DVQLVESGG GVVQPGGSL RLSCVAS | 6 | GYVHKI NFYG | 20 | WYRQAPG KEREKVA | 10 | HISIGD QTD | 24 | YADSAKGRFTISRDE SKNTVYLQMNSLRPE DTAAYYCRA | 14 | LSRIWPYDY | 28 | WGQGT LVTVSS |
| 3 | A022600351* | 19 | EVQLVESGG GVVQPGGSL RLSCAAS | 7 | GFTFSSF AMT | 21 | WVRRPPGK GLEWVA | 11 | TITNKG VTS | 25 | YADSVKGRFTISRDN AKNTLYLQMNSLRPE DTALYICAN | 15 | ARRTGPRAP TDIGSY | 29 | RGQGTL VTVSS |
| 4 | A022600314° | 19 | EVQLVESGG GVVQPGGSL RLSCAAS | 8 | GSIFRSV FSSSTM E | 22 | WYRQAPG KKRELVA | 12 | RIAPGE GTYYG AL | 26 | YADSVKGRFTISRDN AKNTVYLQMNSLRPE DTALYYCAS | 16 | GVA | 28 | WGQGT LVTVSS |
| 5 | ALB23002 | 19 | EVQLVESGG GVVQPGGSL RLSCAAS | 9 | GFTFRSF GMS | 23 | WVRQAPG KGPEWVS | 13 | SISGSG SDTL | 27 | YADSVKGRFTISRDN SKNTLYLQMNSLRPE DTALYYCTI | 17 | GGSLSR | 30 | SSQGTL VTVSS |

*Sequence optimized variant of A02260018C08 (SEQ ID NO: 48)
°Sequence optimized variant of A02260015A08 (SEQ ID NO: 47)

TABLE A-2-1

Sequences for CDRs and frameworks ("ID" refers to the given SEQ ID NO)

| ID | ISVD | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | TCE01 | 39 | DVQLVESGG GVVQPGGSL RLSCVASGY VHK | 31 | INFYG | 20 | WYRQAPG KEREKVA | 35 | HISIGD QTDYA DSAKG | 43 | RFTISRDESKNTVY LQMNSLRPEDTAAY YCRA | 14 | LSRIWPYDY | 28 | WGQGT LVTVSS |
| 3 | A022600351* | 40 | EVQLVESGG GVVQPGGSL RLSCAASGF TFS | 32 | SFAMT | 21 | WVRRPPG KGLEWVA | 36 | TITNKG VTSYA DSVKG | 44 | RFTISRDNAKNTLY LQMNSLRPEDTALY ICAN | 15 | ARRTGPRAP TDIGSY | 29 | RGQGTL VTVSS |
| 4 | A022600314° | 41 | EVQLVESGG GVVQPGGSL RLSCAASGS IFR | 33 | SVFSSST ME | 22 | WYRQAPG KKRELVA | 37 | RIAPGE GTYYG ALYADS VKG | 45 | RFTISRDNAKNTVY LQMNSLRPEDTALY YCAS | 16 | GVA | 28 | WGQGT LVTVSS |
| 5 | ALB23002 | 42 | EVQLVESGG GVVQPGGSL | 34 | SFGMS | 23 | WVRQAPG KGPEWVS | 38 | SISGSG SDTLYA | 46 | RFTISRDNSKNTLY LQMNSLRPEDTALY | 17 | GGSLSR | 30 | SSQGTL VTVSS |

TABLE A-2-1-continued

| Sequences for CDRs and frameworks ("ID" refers to the given SEQ ID NO) | | | | | | | | | | | | | | | |
|---|---|---|---|---|---|---|---|---|---|---|---|---|---|---|---|
| ID | ISVD | ID | FR1 | ID | CDR1 | ID | FR2 | ID | CDR2 | ID | FR3 | ID | CDR3 | ID | FR4 |
| | | | RLSCAASGF<br>TFR | | | | | | DSVKG | | YCTI | | | | |

*Sequence optimized variant of A02260018C08 (SEQ ID NO: 48)
°Sequence optimized variant of A02260015A08 (SEQ ID NO: 47)

TABLE A-3

| Amino acid sequences of selected multivalent ISVD | | |
|---|---|---|
| Name | ID | Amino acid sequence |
| A022600424 | 1 | DVQLVESGGGVVQPGGSLRLSCVASGYVHKINFYGWYRQAPGKEREKVAHISIGDQTDYADSAKGRFTISRDESKNTVYLQMNSLRPEDTAAYYCRALSRIWPYDYWGQGTLVTVSSGGGGSEVQLVESGGGVVQPGGSLRLSCAASGFTFSSFAMTWVRRPPGKGLEWVATITNKGVTSYADSVKGRFTISRDNAKNTLYLQMNSLRPEDTALYICANARRTGPRAPTDIGSYRGQGTLVTVSSGGGGSGGGSEVQLVESGGGVVQPGGSLRLSCAASGSIFRSVFSSSTMEWYRQAPGKKRELVARIAPGEGTYYGALYADSVKGRFTISRDNAKNTVYLQMNSLRPEDTALYYCASGVAWGQGTLVTVSSGGGGSGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |

TABLE A-4

| Serum albumin binding ISVD sequences ("ID" refers to the SEQ ID NO as used herein) | | |
|---|---|---|
| Name | ID | Amino acid sequence |
| Alb8 | 82 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb8-A | 83 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| Alb23 | 84 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb23-A | 85 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSA |
| Alb83 | 86 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSS |
| Alb83-A | 87 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSSA |
| Alb132 | 88 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSS |
| Alb132-A | 89 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSSA |
| Alb73 | 90 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSS |
| Alb73-A | 91 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |

TABLE A-4-continued

| Serum albumin binding ISVD sequences ("ID" refers to the SEQ ID NO as used herein) | | |
|---|---|---|
| Name | ID | Amino acid sequence |
| Alb82 | 92 | EVQLVESGGGVVQPGNSLRLSCAASGFTFSSFGMSWVRQAPGKGLEWVSS ISGSGSDTLYADSVKGRFTISRDNAKTTLYLQMNSLRPEDTALYYCTIGGSLSR SSQGTLVTVSS |
| Alb82-A | 93 | EVQLVESGGGVVQPGNSLRLSCAASGFTFSSFGMSWVRQAPGKGLEWVSS ISGSGSDTLYADSVKGRFTISRDNAKTTLYLQMNSLRPEDTALYYCTIGGSLSR SSQGTLVTVSSA |
| Alb199 | 94 | EVQLVESGGGVVQPGNSLRLSCAASGFTFSSFGMSWVRQAPGKGLEWVSS ISGSGSDTLYADSVKGRFTISRDNAKTTLYLQMNSLRPEDTALYYCTIGGSLSR SSQGTLVKVSS |
| Alb199-A | 95 | EVQLVESGGGVVQPGNSLRLSCAASGFTFSSFGMSWVRQAPGKGLEWVSS ISGSGSDTLYADSVKGRFTISRDNAKTTLYLQMNSLRPEDTALYYCTIGGSLSR SSQGTLVKVSSA |
| Alb23002 | 5 | EVQLVESGGGVVQPGGSLRLSCAASGFTFRSFGMSWVRQAPGKGPEWVSS ISGSGSDTLYADSVKGRFTISRDNSKNTLYLQMNSLRPEDTALYYCTIGGSLSR SSQGTLVTVSS |
| Alb223 | 96 | EVQLVESGGGVVQPGGSLRLSCAASGFTFRSFGMSWVRQAPGKGPEWVSS ISGSGSDTLYADSVKGRFTISRDNSKNTLYLQMNSLRPEDTALYYCTIGGSLSR SSQGTLVTVSSA |
| Alb216 | 97 | EVQLVESGGGVVQPGGSLRLSCAASGFTFRSFGMSWVRQAPGKGPEWVSS ISGSGSDTLYADSVKGRFTISRDNSKNTLYLQMNSLRPEDTALYYCTIGGSLSR SSQGTLVKVSS |
| Alb216-A | 98 | EVQLVESGGGVVQPGGSLRLSCAASGFTFRSFGMSWVRQAPGKGPEWVSS ISGSGSDTLYADSVKGRFTISRDNSKNTLYLQMNSLRPEDTALYYCTIGGSLSR SSQGTLVKVSSA |

TABLE A-5

| Linker sequences ("ID" refers to the SEQ ID NO as used herein) | | |
|---|---|---|
| Name | ID | Amino acid sequence |
| 3A linker | 99 | AAA |
| 5GS linker | 100 | GGGGS |
| 7GS linker | 101 | SGGSGGS |
| 8GS linker | 102 | GGGGSGGS |
| 9GS linker | 103 | GGGGSGGGS |
| 10GS linker | 104 | GGGGSGGGGS |
| 15GS linker | 105 | GGGGSGGGGSGGGGS |
| 18GS linker | 106 | GGGGSGGGGSGGGGSGGS |
| 20GS linker | 107 | GGGGSGGGGSGGGGSGGGGS |
| 25GS linker | 108 | GGGGSGGGGSGGGGSGGGGSGGGGS |
| 30GS linker | 109 | GGGGSGGGGSGGGGSGGGGSGGGGSGGGGS |
| 35GS linker | 110 | GGGGSGGGGSGGGGSGGGGSGGGGSGGGGSGGGGS |
| 40GS linker | 111 | GGGGSGGGGSGGGGSGGGGSGGGGSGGGGSGGGGSGGGGS |
| G1 hinge | 112 | EPKSCDKTHTCPPCP |
| 9GS-G1 hinge | 113 | GGGGSGGGSEPKSCDKTHTCPPCP |
| Llama upper long hinge region | 114 | EPKTPKPQPAAA |

TABLE A-5-continued

| Linker sequences ("ID" refers to the SEQ ID NO as used herein) | | |
|---|---|---|
| Name | ID | Amino acid sequence |
| G3 hinge | 115 | ELKTPLGDTTHTCPRCPEPKSCDTPPPCPRCPEPKSCDTPPPCPRCPEPKSCDTPPPCPRCP |

TABLE A-6

| Amino acid sequences of selected multivalent polypeptides ("ID" refers to the given SEQ ID NO) | |
|---|---|
| SEQ ID | Sequence |
| 49 A022600027 | DVQLVESGGGLVQPGGSLRLSCVASGDVHKINFLGWYRQAPGKEREKVAHISIGDQTDYADSAKGRFTISRDESKNMVYLQMNSLKPEDTAVYFCRAFSRIYPYDYWGQGTLVTVSSGGGGSGGGGSGGGGSGGGGSGGGGSGGGGSGGGGSEVQLVESGGGLVQPGGSLRLSCVASGFTFSSFAMTWVRRPPGKGLEWVATITNGGVTSYRDSVKGRFTISRDNAKNTLYLEMTSLNPEDTAVYICANARRTGPRAPTDIGSYRGQGTLVTVSSGGGGSGGGGSGGGGSGGGGSGGGGSGGGGSGGGGSEVQLVESGGGVVQPGGSLRLSCAASGLTFSSYAMGWFRQAPGKERERVVSISRGGGYTYYADSVKGRFTISRDNSENTVYLQMNSLRPEDTALYYCAAARYWATGSEYEFDYWGQGTLVTVSS |
| 50 A022600031 | DVQLVESGGGLVQPGGSLRLSCVASGDVHKINFLGWYRQAPGKEREKVAHISIGDQTDYADSAKGRFTISRDESKNMVYLQMNSLKPEDTAVYFCRAFSRIYPYDYWGQGTLVTVSSGGGGSGGGGSGGGGSGGGGSGGGGSGGGGSGGGGSEVQLVESGGGLVQAGGSLRLSCVASGSIFRSVFSSSTMEWYRQPPGKKRELVARIAPGDGTNYGALYADSVKGRFTISRDDAKKTVDLQMNSLKPEDTGVYFCASGVAWGQGTLVTVSSGGGGSGGGGSGGGGSGGGGSGGGGSGGGGSGGGGSEVOLVESGGGVVQPGGSLRLSCAASGLTFSSYAMGWFRQAPGKERERVVSISRGGGYTYYADSVKGRFTISRDNSENTVYLQMNSLRPEDTALYYCAAARYWATGSEYEFDYWGQGTLVTVSS |
| 51 A022600096 | DVQLVESGGGLVQPGGSLRLSCVASGYVHKINFYGWYRQAPGKEREKVAHISIGDQTDYADSAKGRFTISRDESKNTVYLQMNSLRPEDTALYYCRALSRIWPYDYWGQGTLVTVSSGGGGSGGGGSGGGGSGGGGSGGGGSGGGGSGGGGSEVQLVESGGGLVQPGGSLRLSCVASGFTFSSFAMTWVRRPPGKGLEWVATITNGGVTSYRDSVKGRFTISRDNAKNTLYLEMTSLNPEDTAVYICANARRTGPRAPTDIGSYRGQGTLVTVSSGGGGSGGGGSGGGGSGGGGSGGGGSGGGGSGGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| 52 A022600102 | DVQLVESGGGVVQPGGSLRLSCVASGYVHKINFYGWYRQAPGKEREKVAHISIGDQTDYADSAKGRFTISRDESKNTVYLQMNSLRPEDTALYYCRALSRIWPYDYWGQGTLVTVSSAAAEVQLVESGGGLVQPGGSLRLSCVASGFTFSSFAMTWVRRPPGKGLEWVATITNGGVTSYRDSVKGRFTISRDNAKNTLYLEMTSLNPEDTAVYICANARRTGPRAPTDIGSYRGQGTLVTVSSGGGGSGGGGSGGGGSGGGGSGGGGSGGGGSGGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| 53 A022600103 | DVQLVESGGGVVQPGGSLRLSCVASGYVHKINFYGWYRQAPGKEREKVAHISIGDQTDYADSAKGRFTISRDESKNTVYLQMNSLRPEDTALYYCRALSRIWPYDYWGQGTLVTVSSGGGGSEVQLVESGGGLVQPGGSLRLSCVASGFTFSSFAMTWVRRPPGKGLEWVATITNGGVTSYRDSVKGRFTISRDNAKNTLYLEMTSLNPEDTAVYICANARRTGPRAPTDIGSYRGQGTLVTVSSGGGGSGGGGSGGGGSGGGGSGGGGSGGGGSGGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| 54 A022600104 | DVQLVESGGGVVQPGGSLRLSCVASGYVHKINFYGWYRQAPGKEREKVAHISIGDQTDYADSAKGRFTISRDESKNTVYLQMNSLRPEDTALYYCRALSRIWPYDYWGQGTLVTVSSGGGGSGGGSEVOLVESGGGLVQPGGSLRLSCVASGFTFSSFAMTWVRRPPGKGLEWVATITNGGVTSYRDSVKGRFTISRDNAKNTLYLEMTSLNPEDTAVYICANARRTGPRAPTDIGSYRGQGTLVTVSSGGGGSGGGGSGGGGSGGGGSGGGGSGGGGSGGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| 55 A022600105 | DVQLVESGGGVVQPGGSLRLSCVASGYVHKINFYGWYRQAPGKEREKVAHISIGDQTDYADSAKGRFTISRDESKNTVYLQMNSLRPEDTALYYCRALSRIWPYDYWGQGTLVTVSSGGGGSGGGGSGGGGSGGGGSEVQLVESGGGLVQPGGSLRLSCVASGFTFSSFAMTWVRRPPGKGLEWVATITNGGVTSYR |

TABLE A-6-continued

Amino acid sequences of selected multivalent polypeptides ("ID" refers to the given SEQ ID NO)

| SEQ ID | Sequence |
|---|---|
| | DSVKGRFTISRDNAKNTLYLEMTSLNPEDTAVYICANARRTGPRAPTDIGS YRGQGTLVTVSSGGGGSGGGGSGGGGSGGGGSGGGGSGGGGSGGGGS EVQLVESGGGVVQPGGSLRLSCAASGFTFRSFGMSWVRQAPGKGPEWV SSISGSGSDTLYADSVKGRFTISRDNSKNTLYLQMNSLRPEDTALYYCTIGG SLSRSSQGTLVTVSSA |
| 56 A022600122 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSGGGGSGGGGSGGGGSEVQLVESGGGLVQPGG SLRLSCVASGSIFRSVFSSSTMEWYRQPPGKKRELVARIAPGDGTNYGALY ADSVKGRFTISRDDAKKTVDLQMNSLKPEDTGVYFCASGVAWGQGTLVT VSSGGGGSGGGGSGGGGSGGGGSGGGGSGGGGSGGGGSEVQLVESGG GVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTL VTVSSA |
| 57 A022600131 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGGSGGGGSGGGGSEVQLVESGGGLVQPGGSLRLSCVASGSIFRSVFSS STMEWYRQPPGKKRELVARIAPGDGTNYGALYADSVKGRFTISRDDAKKT VDLQMNSLKPEDTGVYFCASGVAWGQGTLVTVSSGGGGSGGGGSGGG GSGGGGSGGGGSGGGGSGGGGSEVQLVESGGGVVQPGGSLRLSCAASG FTFRSFGMSWVRQAPGKGPEWVSSISGSGSDTLYADSVKGRFTISRDNSK NTLYLQMNSLRPEDTALYYCTIGGSLSRSSQGTLVTVSSA |
| 58 A022600132 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVQLVESGGGLVQPGGSLRLSCVASGFT FSSFAMTWVRRPPGKGLEWVATITNGGVTSYRDSVKGRFTISRDNAKNTL YLEMTSLNPEDTAVYICANARRTGPRAPTDIGSYRGQGTLVTVSSGGGGS GGGSEVQLVESGGGLVQPGGSLRLSCVASGSIFRSVFSSSTMEWYRQPPG KKRELVARIAPGDGTNYGALYADSVKGRFTISRDDAKKTVDLQMNSLKPE DTGVYFCASGVAWGQGTLVTVSSGGGGSGGGGSGGGGSGGGGSGGG GSGGGGSGGGGSEVQLVESGGGVVQPGGSLRLSCAASGFTFRSFGMSW VRQAPGKGPEWVSSISGSGSDTLYADSVKGRFTISRDNSKNTLYLQMNSL RPEDTALYYCTIGGSLSRSSQGTLVTVSSA |
| 59 A022600133 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVOLVESGGGLVQPGGSLRLSCVASGS1 FRSVFSSSTMEWYRQPPGKKRELVARIAPGDGTNYGALYADSVKGRFTISR DDAKKTVDLQMNSLKPEDTGVYFCASGVAWGQGTLVTVSSGGGGSGGG GSGGGGSGGGGSGGGGSGGGGSGGGGSEVQLVESGGGLVQPGGSLRL SCVASGFTFSSFAMTWVRRPPGKGLEWVATITNGGVTSYRDSVKGRFTIS RDNAKNTLYLEMTSLNPEDTAVYICANARRTGPRAPTDIGSYRGQGTLVT VSSGGGGSGGGGSGGGGSGGGGSGGGGSGGGGSGGGGSEVQLVESGG GVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTL VTVSSA |
| 60 A022600134 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVOLVESGGGLVQPGGSLRLSCVASGS1 FRSVFSSSTMEWYRQPPGKKRELVARIAPGDGTNYGALYADSVKGRFTISR DDAKKTVDLQMNSLKPEDTGVYFCASGVAWGQGTLVTVSSGGGGSGGG GSGGGGSGGGGSEVQLVESGGGLVQPGGSLRLSCVASGFTFSSFAMTWV RRPPGKGLEWVATITNGGVTSYRDSVKGRFTISRDNAKNTLYLEMTSLNPE DTAVYICANARRTGPRAPTDIGSYRGQGTLVTVSSGGGGSGGGGSGGGG SGGGGSGGGGSGGGGSGGGGSEVQLVESGGGVVQPGGSLRLSCAASGF TFRSFGMSWVRQAPGKGPEWVSSISGSGSDTLYADSVKGRFTISRDNSKN TLYLQMNSLRPEDTALYYCTIGGSLSRSSQGTLVTVSSA |
| 61 A022600135 | DVQLVESGGGVVQPGGSLRLSCVASGYVHKINFYGWYRQAPGKEREKVA HISIGDQTDYADSAKGRFTISRDESKNTVYLQMNSLRPEDTALYYCRALSRI WPYDYWGQGTLVTVSSGGGGSEVOLVESGGGLVQPGGSLRLSCVASGS1 FRSVFSSSTMEWYRQPPGKKRELVARIAPGDGTNYGALYADSVKGRFTISR DDAKKTVDLQMNSLKPEDTGVYFCASGVAWGQGTLVTVSSGGGGSGGG SEVQLVESGGGLVQPGGSLRLSCVASGFTFSSFAMTWVRRPPGKGLEWV ATITNGGVTSYRDSVKGRFTISRDNAKNTLYLEMTSLNPEDTAVYICANAR |

TABLE A-6-continued

Amino acid sequences of selected multivalent polypeptides ("ID" refers to the given SEQ ID NO)

| SEQ ID | Sequence |
|---|---|
| | RTGPRAPTDIGSYRGQGTLVTVSSGGGGSGGGGSGGGGSGGGGSGGGG<br>SGGGGSGGGGSEVQLVESGGGVVQPGGSLRLSCAASGFTFRSFGMSWV<br>RQAPGKGPEWVSSISGSGSDTLYADSVKGRFTISRDNSKNTLYLQMNSLR<br>PEDTALYYCTIGGSLSRSSQGTLVTVSSA |
| 62 A022600167 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGGSGGGGSGGGGSGGGGSGGGGSGGGGSGGGGSEVQLVESGGGVVQPGG<br>SLRLSCAASGFTFRSFGMSWVRQAPGKGPEWVSSISGSGSDTLYADSVKG<br>RFTISRDNSKNTLYLQMNSLRPEDTALYYCTIGGSLSRSSQGTLVTVSSA |
| 63 A022600168 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGGSGGGGSGGGGSGGGGSGGGGSGGGGSGGGGSEVQLVESGGGLVQPGG<br>SLRLSCVASGSIFRSVFSSSTMEWYRQPPGKKRELVARIAPGDGTNYGALY<br>ADSVKGRFTISRDDAKKTVDLQMNSLKPEDTGVYFCASGVAWGQGTLVT<br>VSSGGGGSGGGGSGGGGSGGGGSGGGGSGGGGSGGGGSEVQLVESGG<br>GVVQPGGSLRLSCAASGFTFRSFGMSWVRQAPGKGPEWVSSISGSGSDT<br>LYADSVKGRFTISRDNSKNTLYLQMNSLRPEDTALYYCTIGGSLSRSSQGTL<br>VTVSSA |
| 64 A022600169 | DVQLVESGGGLVQPGGSLRLSCVASGFTFSSFAMTWVRRPPGKGLEWVA<br>TITNGGVTSYRDSVKGRFTISRDNAKNTLYLEMTSLNPEDTAVYICANARRT<br>GPRAPTDIGSYRGQGTLVTVSSGGGGSEVQLVESGGGVVQPGGSLRLSCV<br>ASGYVHKINFYGWYRQAPGKEREKVAHISIGDQTDYADSAKGRFTISRDES<br>KNTVYLQMNSLRPEDTAAYYCRALSRIWPYDYWGQGTLVTVSSGGGGSE<br>VQLVESGGGLVQPGGSLRLSCVASGSIFRSVFSSSTMEWYRQPPGKKREL<br>VARIAPGDGTNYGALYADSVKGRFTISRDDAKKTVDLQMNSLKPEDTGVY<br>FCASGVAWGQGTLVTVSSGGGGSGGGGSGGGGSGGGGSGGGGSGGG<br>GSGGGGSEVQLVESGGGVVQPGGSLRLSCAASGFTFRSFGMSWVRQAP<br>GKGPEWVSSISGSGSDTLYADSVKGRFTISRDNSKNTLYLQMNSLRPEDTA<br>LYYCTIGGSLSRSSQGTLVTVSSA |
| 65 A022600170 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGGSGGGGSGGGGSGGGGSGGGGSGGGGSGGGGSEVQLVESGGGLVQPGG<br>SLRLSCVASGSIFRSVFSSSTMEWYRQPPGKKRELVARIAPGDGTNYGALY<br>ADSVKGRFTISRDDAKKTVDLQMNSLKPEDTGVYFCASGVAWGQGTLVT<br>VSSGGGGSGGGSEVQLVESGGGVVQPGGSLRLSCAASGFTFRSFGMSW<br>VRQAPGKGPEWVSSISGSGSDTLYADSVKGRFTISRDNSKNTLYLQMNSL<br>RPEDTALYYCTIGGSLSRSSQGTLVTVSSA |
| 66 A022600172 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGSEVQLVESGGGVVQPGGSLRLSCAASGFTFRSFGMSWVRQAPGKG<br>PEWVSSISGSGSDTLYADSVKGRFTISRDNSKNTLYLQMNSLRPEDTALYY<br>CTIGGSLSRSSQGTLVTVSSGGGGSGGGSEVQLVESGGGLVQPGGSLRLSC<br>VASGSIFRSVFSSSTMEWYRQPPGKKRELVARIAPGDGTNYGALYADSVK<br>GRFTISRDDAKKTVDLQMNSLKPEDTGVYFCASGVAWGQGTLVTVSSA |
| 67 A022600174 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGSEVQLVESGGGLVQPGGSLRLSCVASGSIFRSVFSSSTMEWYRQPPG<br>KKRELVARIAPGDGTNYGALYADSVKGRFTISRDDAKKTVDLQMNSLKPE<br>DTGVYFCASGVAWGQGTLVTVSSGGGGSGGGSEVQLVESGGGVVQPG<br>GSLRLSCAASGFTFRSFGMSWVRQAPGKGPEWVSSISGSGSDTLYADSVK<br>GRFTISRDNSKNTLYLQMNSLRPEDTALYYCTIGGSLSRSSQGTLVTVSSA |
| 68 A022600175 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI |

TABLE A-6-continued

Amino acid sequences of selected multivalent polypeptides ("ID" refers to the given SEQ ID NO)

| SEQ ID | Sequence |
|---|---|
| | WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGSEVQLVESGGGLVQPGGSLRLSCVASGSIFRSVFSSSTMEWYRQPPG<br>KKRELVARIAPGDGTNYGALYADSVKGRFTISRDDAKKTVDLQMNSLKPE<br>DTGVYFCASGVAWGQGTLVTVSSGGGGSGGGGSGGGGSGGGGSGGG<br>GSGGGGSGGGGSEVQLVESGGGVVQPGGSLRLSCAASGFTFRSFGMSW<br>VRQAPGKGPEWVSSISGSGSDTLYADSVKGRFTISRDNSKNTLYLQMNSL<br>RPEDTALYYCTIGGSLSRSSQGTLVTVSSA |
| 69 A022600178 | DVQLVESGGGLVQPGGSLRLSCVASGFTFSSFAMTWVRRPPGKGLEWVA<br>TITNGGVTSYRDSVKGRFTISRDNAKNTLYLEMTSLNPEDTAVYICANARRT<br>GPRAPTDIGSYRGQGTLVTVSSGGGGSEVQLVESGGGVVQPGGSLRLSCV<br>ASGYVHKINFYGWYRQAPGKEREKVAHISIGDQTDYADSAKGRFTISRDES<br>KNTVYLQMNSLRPEDTAAYYCRALSRIWPYDYWGQGTLVTVSSGGGGSG<br>GGGSGGGGSGGGGSGGGGSGGGGSGGGGSEVQLVESGGGVVQPGGSL<br>RLSCAASGFTFRSFGMSWVRQAPGKGPEWVSSISGSGSDTLYADSVKGRF<br>TISRDNSKNTLYLQMNSLRPEDTALYYCTIGGSLSRSSQGTLVTVSSA |
| 70 A022600179 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGLVQPGGSLRLSCVASGFT<br>FSSFAMTWVRRPPGKGLEWVATITNGGVTSYRDSVKGRFTISRDNAKNTL<br>YLEMTSLNPEDTAVYICANARRTGPRAPTDIGSYRGQGTLVTVSSGGGGS<br>GGGSEVQLVESGGGVVQPGGSLRLSCAASGFTFRSFGMSWVRQAPGKG<br>PEWVSSISGSGSDTLYADSVKGRFTISRDNSKNTLYLQMNSLRPEDTALYY<br>CTIGGSLSRSSQGTLVTVSSA |
| 71 A022600370 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGVVQPGGSLRLSCVASGF<br>TFSSFAMTWVRRPPGKGLEWVATITNGGVTSYRDSVKGRFTISRDNAKNT<br>LYLEMTSLRPEDTALYICANARRTGPRAPTDIGSYRGQGTLVTVSSGGGGS<br>GGGGSGGGGSGGGGSEVQLVESGGGVVQPGGSLRLSCAASGFTFRSFG<br>MSWVRQAPGKGPEWVSSISGSGSDTLYADSVKGRFTISRDNSKNTLYLQ<br>MNSLRPEDTALYYCTIGGSLSRSSQGTLVTVSSGGC |
| 72 A022600372 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGVVQPGGSLRLSCVASGF<br>TFSSFAMTWVRRPPGKGLEWVATITNGGVTSYRDSVKGRFTISRDNAKNT<br>LYLEMTSLRPEDTALYICANARRTGPRAPTDIGSYRGQGTLVTVSSGGGGS<br>GGGSEVQLVESGGGVVQPGGSLRLSCVASGSIFRSVFSSSTMEWYRQPPG<br>KKRELVARIAPGDGTNYGALYADSVKGRFTISRDDAKKTVDLQMNSLRPE<br>DTGLYFCASGVAWGQGTLVTVSSGGGGSGGGSEVQLVESGGGVVQPGG<br>SLRLSCAASGFTFRSFGMSWVRQAPGKGPEWVSSISGSGSDTLYADSVKG<br>RFTISRDNSKNTLYLQMNSLRPEDTALYYCTIGGSLSRSSQGTLVTVSSGGC |
| 73 A022600373 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSGGGGSGGGGSGGGGSEVQLVESGGG<br>VVQPGGSLRLSCAASGFTFRSFGMSWVRQAPGKGPEWVSSISGSGSDTL<br>YADSVKGRFTISRDNSKNTLYLQMNSLRPEDTALYYCTIGGSLSRSSQGTLV<br>TVSSGGC |
| 74 T017000698 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSGGGSEVOLVESGGGVVQPGGSLRLSCA<br>ASGFTFRSFGMSWVRQAPGKGPEWVSSISGSGSDTLYADSVKGRFTISRD<br>NSKNTLYLQMNSLRPEDTALYYCTIGGSLSRSSQGTLVTVSSA |
| 78 A022600412 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGVVQPGGSLRLSCAASGF<br>TFSSFAMTWVRRPPGKGLEWVATITNAGVTSYADSVKGRFTISRDNAKNT<br>LYLQMNSLRPEDTALYICANARRTGPRAPTDIGSYRGQGTLVTVSSGGGG<br>SGGGGSGGGGSGGGGSEVQLVESGGGVVQPGGSLRLSCAASGFTFRSFG<br>MSWVRQAPGKGPEWVSSISGSGSDTLYADSVKGRFTISRDNSKNTLYLQ<br>MNSLRPEDTALYYCTIGGSLSRSSQGTLVTVSSA |
| 1 A022600424 | DVQLVESGGGVVQPGGSLRLSCVASGYVHKINFYGWYRQAPGKEREKVA<br>HISIGDQTDYADSAKGRFTISRDESKNTVYLQMNSLRPEDTAAYYCRALSRI<br>WPYDYWGQGTLVTVSSGGGGSEVQLVESGGGVVQPGGSLRLSCAASGF<br>TFSSFAMTWVRRPPGKGLEWVATITNKGVTSYADSVKGRFTISRDNAKNT<br>LYLQMNSLRPEDTALYICANARRTGPRAPTDIGSYRGQGTLVTVSSGGGG |

TABLE A-6-continued

| Amino acid sequences of selected multivalent polypeptides ("ID" refers to the given SEQ ID NO) | |
|---|---|
| SEQ ID | Sequence |
| | SGGGSEVQLVESGGGVVQPGGSLRLSCAASGSIFRSVFSSSTMEWYRQAP GKKRELVARIAPGEGTYYGALYADSVKGRFTISRDNAKNTVYLQMNSLRPE DTALYYCASGVAWGQGTLVTVSSGGGGSGGGSEVQLVESGGGVVQPGG SLRLSCAASGFTFRSFGMSWVRQAPGKGPEWVSSISGSGSDTLYADSVKG RFTISRDNSKNTLYLQMNSLRPEDTALYYCTIGGSLSRSSQGTLVTVSSA |
| 79 A022600425 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSSGGGGSEVOLVESGGGVVQPGGSLRLSCAASGSI FRSVFSSSTMEWYRQAPGKKRELVARIAPGEGTYYGALYADSVKGRFTISR DNAKNTVYLQMNSLRPEDTALYYCASGVAWGQGTLVTVSSGGGGSGGG GSGGGGSGGGGSEVQLVESGGGVVQPGGSLRLSCAASGFTFSSFAMTW VRRPPGKGLEWVATITNAGVTSYADSVKGRFTISRDNAKNTLYLQMNSLR PEDTALYICANARRTGPRAPTDIGSYRGQGTLVTVSSGGGGSGGGSEVQL VESGGGVVQPGGSLRLSCAASGFTFRSFGMSWVRQAPGKGPEWVSSISG SGSDTLYADSVKGRFTISRDNSKNTLYLQMNSLRPEDTALYYCTIGGSLSRS SQGTLVTVSSA |
| 80 A022600426 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSSGGGGSEVOLVESGGGVVQPGGSLRLSCAASGSI FRSVFSSSTMEWYRQAPGKKRELVARIAPGEGTYYGALYADSVKGRFTISR DNAKNTVYLQMNSLRPEDTALYYCASGVAWGQGTLVTVSSGGGGSGGG GSGGGGSGGGGSEVQLVESGGGVVQPGGSLRLSCAASGFTFSSFAMTW VRRPPGKGLEWVATITNKGVTSYADSVKGRFTISRDNAKNTLYLQMNSLR PEDTALYICANARRTGPRAPTDIGSYRGQGTLVTVSSGGGGSGGGSEVQL VESGGGVVQPGGSLRLSCAASGFTFRSFGMSWVRQAPGKGPEWVSSISG SGSDTLYADSVKGRFTISRDNSKNTLYLQMNSLRPEDTALYYCTIGGSLSRS SQGTLVTVSSA |
| 81 A022600427 | DVQLVESGGGVVQPGGSLRLSCVASGYVHKINFYGWYRQAPGKEREKVA HISIGDQTDYADSAKGRFTISRDESKNTVYLQMNSLRPEDTAAYYCRALSRI WPYDYWGQGTLVTVSSGGGGSEVQLVESGGGVVQPGGSLRLSCAASGF TFSSFAMTWVRRPPGKGLEWVATITNAGVTSYADSVKGRFTISRDNAKNT LYLQMNSLRPEDTALYICANARRTGPRAPTDIGSYRGQGTLVTVSSGGGG SGGGSEVQLVESGGGVVQPGGSLRLSCAASGSIFRSVFSSSTMEWYRQAP GKKRELVARIAPGEGTYYGALYADSVKGRFTISRDNAKNTVYLQMNSLRPE DTALYYCASGVAWGQGTLVTVSSGGGGSGGGSEVQLVESGGGVVQPGG SLRLSCAASGFTFRSFGMSWVRQAPGKGPEWVSSISGSGSDTLYADSVKG RFTISRDNSKNTLYLQMNSLRPEDTALYYCTIGGSLSRSSQGTLVTVSSA |

TABLE A-7

| C-termini with or without C-terminal extensions ("ID" refers to the given SEQ ID NO as used herein) | |
|---|---|
| ID | Amino acid sequence |
| 116 | VTVSS |
| 117 | VKVSS |
| 118 | VQVSS |
| 119 | VTVKS |
| 120 | VTVQS |
| 121 | VKVKS |
| 122 | VKVQS |
| 123 | VQVKS |
| 124 | VQVQS |
| 125 | VTVSSA |
| 126 | VKVSSA |

TABLE A-7-continued

| C-termini with or without C-terminal extensions ("ID" refers to the given SEQ ID NO as used herein) | |
|---|---|
| ID | Amino acid sequence |
| 127 | VQVSSA |
| 128 | VTVKSA |
| 129 | VTVQSA |
| 130 | VKVKSA |
| 131 | VKVQSA |
| 132 | VQVKSA |
| 133 | VQVQSA |

TABLE A-8

Amino acid sequences related to GPC3 and TCR

| ID | description | Amino acid sequence |
|---|---|---|
| 134 | Human GPC3 (P51654) | MAGTVRTACLVVAMLLSLDFPGQAQPPPPPPDATCHQVRSFFQRLQPGL KWVPETPVPGSDLQVCLPKGPTCCSRKMEEKYQLTARLNMEQLLQSASM ELKFLIIQNAAVFQEAFEIVVRHAKNYTNAMFKNNYPSLTPQAFEFVGEFFT DVSLYILGSDINVDDMVNELFDSLFPVIYTQLMNPGLPDSALDINECLRGA RRDLKVFGNFPKLIMTQVSKSLQVTRIFLQALNLGIEVINTTDHLKFSKDCG RMLTRMWYCSYCQGLMMVKPCGGYCNVVMQGCMAGVVEIDKYWRE YILSLEELVNGMYRIYDMENVLLGLFSTIHDSIQYVQKNAGKLTTTIGKLCA HSQQRQYRSAYYPEDLFIDKKVLKVAHVEHEETLSSRRRELIQKLKSFISFYS ALPGYICSHSPVAENDTLCWNGQELVERYSQKAARNGMKNQFNLHELK MKGPEPVVSQIIDKLKHINQLLRTMSMPKGRVLDKNLDEEGFESGDCGDD EDECIGGSGDGMIKVKNQLRFLAELAYDLDVDDAPGNSQQATPKDNEIST FHNLGNVHSPLKLLTSMAISVVCFFFLVH |
| 135 | Human TCR alpha constant domain (derived from P01848) | PNIQNPDPAVYQLRDSKSSDKSVCLFTDFDSQTNVSQSKDSDVYITDKTVL DMRSMDFKSNSAVAWSNKSDFACANAFNNSIIPEDTFFPSPESSC |
| 136 | Human TCR beta constant domain (derived from P01850) | EDLNKVFPPEVAVFEPSEAEISHTQKATLVCLATGFFPDHVELSWWVNGK EVHSGVSTDPQPLKEQPALNDSRYALSSRLRVSATFWQNPRNHFRCQVQ FYGLSENDEWTQDRAKPVTQIVSAEAWGRADC |

6 EXAMPLES

6.1 Example 1: Discovery of ISVDs Specifically Binding to GPC3

2 Llamas and 1 alpaca were immunized with DNA double gene vector containing the sequence encoding the human glypican-3 isoform 2 precursor [NP_004475; 580 AA; *Homo sapiens*]. Later, the animals were boosted with recombinant human Glypican-3 (R&D Systems, cat nr. 2119-GP).

Following the final immunogen injection, blood samples were collected and peripheral blood mononuclear cells (PBMCs) were prepared using Ficoll-Hypaque according to the manufacturer's instructions (Amersham Biosciences, Piscataway, NJ, US) and total RNA was extracted and stored.

Total RNA was used as starting material for RT-PCR to amplify ISVD encoding gene fragments. These fragments were cloned into phagemid vector pAX212. Phage were prepared according to standard protocols (Antibody Phage Display: Methods and Protocols (First Edition, 2002, O'Brian and Aitken eds., Humana Press, Totowa, NJ) and stored after filter sterilization at 4° C. until further use. From each immunized animal a phage library was constructed, yielding library sizes of $3\times10^8$, $6\times10^8$ and $8\times10^8$ cfu.

The phage display libraries were probed using recombinant protein. Briefly, the phage particles were added to the biotinylated antigen (human GPC3 R&D Systems, cat nr. 2119-GP; cyno GPC3 DGPI DHS-HIS, in-house produced (accession number P51654; Q3-R358; 5359-H559, S495A, S509A); all biotinylated using standard protocols) at 50 nM (in PBS supplemented with 2% Marvel and 0.05% Tween 20). The biotinylated antigen was captured on streptavidin or anti-biotin coated magnetic beads (Invitrogen). Unbound phage were washed away (with PBS supplemented with 0.05% Tween 20); bound phage were eluted by addition of trypsin (1 mg/mL in PBS). Eluted phage were allowed to infect exponentially growing *E. coli* TG-1 cells to use for either a subsequent selection round (after rescue with helper phage), and/or for screening of individual clones after plating out on agar plates. For this, individual colonies were picked into 96-deep-well plates containing 0.5 mL medium and grown overnight. 80 μL of the overnight culture of each clone were mixed with 40 μL of 60% glycerol in 2×TY and stored at −80° C.

For small-scale production of ISVDs, 96 deep well plates (1 mL volume) were inoculated with the overnight cultures. ISVD expression was induced by adding IPTG to a final concentration of 1 mM. Periplasmic extracts were prepared by freezing the cell pellets and dissolving them in 100 μL PBS. Cell debris was removed by centrifugation.

Periplasmic extracts were screened in an ELISA for binding to human and cyno GPC3. 384-well high binding SpectraPlates (PerkinElmer, 6007509) were coated overnight at 4° C. with 1 μg/mL of protein (in PBS). The plates were then blocked for at least one hour (PBS, 1% casein) at RT. 1:10 dilutions (in PBS, 0.1% casein, 0.05% Tween 20) of periplasmic extracts were added for one hour at RT. Unbound periplasmic extracts were washed away (PBS supplemented with 0.05% Tween 20) and bound ISVDs were detected using mouse anti-FLAG-HRP (Sigma-Aldrich, cat nr A8592) and a subsequent enzymatic reaction in the presence of the substrate esTMB (3,3',5,5'-tetramentylbenzidine; SDT).

Positive hits in ELISA were DNA-sequenced and non-redundant clones were further analyzed for off-rates on human and cyno GPC3 as well as binding to cells expressing human and cyno GPC3.

Off-rates of ISVDs were determined on a ProteOn XPR36 instrument (Bio-Rad Laboratories, Inc.). ProteOn GLC Sensor Chips were coated with cyno Glypican-3 AGPI-HIS (in-house produced; accession number P51654; Q3-R358; 5359-H559) and human GPC3 (R&D Systems, cat nr. 2119-GP). Periplasmic extracts were diluted 1:10 in ProteOn PBS Tween buffer (PBS, pH 7.4, 0.005% Tween 20 (167-2720, BioRad)). Experiments were carried out at 25° C. Data obtained was double referenced by reference lane subtraction as well as subtraction of a blank buffer injection. Processed curves were used for off-rate analysis based on the Langmuir dissociation (off-rate analysis) model.

Periplasmic extracts were screened for human and cyno GPC3 binding in flow cytometry using CHO Flp-In cells (Invitrogen cat nr. K6010) expressing either human GPC3 (accession number P51654; Q25-R358, S359-H580) or cyno GPC3 (accession number P51654; Q3-R358; S359-H559), respectively. In brief, $1\times10^5$ cells were incubated in 1:5 diluted periplasmic extracts for 30 min at 4° C., and then washed 3 times. As a control, the parental CHO Flp-In cell line (Invitrogen cat nr. K6010) was included. Next, cells were incubated with 1 μg/mL monoclonal anti-FLAG© M2 antibody (Sigma-Aldrich, cat nr F1804) for 30 min at 4° C., washed again, and incubated for 30 min at 4° C. with goat anti-mouse PE labelled antibody (1:100; Jackson Immunoresearch, cat nr. 115-115-164). Samples were washed and resuspended in FACS Buffer (D-PBS (Gibco) with 10% FBS (Sigma) and 0.05% sodium azide (Merck)) supplemented with 5 nM TOPRO3 (Molecular Probes, cat nr T3605). Cell suspensions were then analyzed on a FACS Array. Gating was set on live, intact cells using forward/side scatter and TOPRO3 channel fluorescence parameters. Mean PE channel fluorescence values higher than those obtained for control conditions including a non-binding ISVD indicated a hit.

Based on off-rate analysis and binding to human and cyno GPC3-expressing CHO cells (Table 2), two ISVDs were selected (Table 1).

TABLE 1

Amino acid sequences of anti-GPC3 ISVDs

| ISVD ID | SEQUENCE |
|---|---|
| A0226015A08 (SEQ ID NO: 47) | EVQLVESGGGLVQAGGSLRLSCVASGSIFRSVFSSSTMEWYRQPPGKKRELV ARIAPGDGTNYGALYADSVKGRFTISRDDAKKTVDLQMNSLKPEDTGVYFC ASGVAWGQGTLVTVSS |
| A0226018C08 (SEQ ID NO: 48) | EVQLVESGGGLVQPGGSLRLSCVASGFTFSSFAMTWVRRPPGKGLEWVATI TNGGVTSYRDSVKGRFTISRDNAKNTLYLEMTSLNPEDTAVYICANARRTGP RAPTDIGSYRGQGTLVTVSS |

TABLE 2

Summary of the screening results of anti-GPC3 ISVDs A0226015A08 and A0226018C08

| ISVD ID | $k_{off}$ hGPC3 (1/s) | $k_{off}$ cyGPC3 (1/s) | Ratio MFI hGPC3 CHO/CHO | Ratio MFI cyGPC3 CHO/CHO |
|---|---|---|---|---|
| A0226015A08 | 3.3E−04 | 4.0E−04 | 58.2 | 13.7 |
| A0226018C08 | 9.7E−04 | 1.1E−03 | 158.9 | 19.9 |

6.2 Example 2: Generation of Trispecific GPC3 ISVD Based T-Cell Engager

The selected anti-GPC3 ISVDs (sequences in Table 1) were formatted in a trispecific construct with a fixed T-cell engager ISVD which binds to the constant domain of the TCR (T0170056G05, anti-TCR) at the N-terminus and a fixed albumin binding ISVD (ALBX00001) at the C-terminus. The building blocks in the construct are genetically linked by a flexible 35GS (GlySer linker), resulting in the format anti-TCR-35GS-anti-GPC3-35GS-ALBX00001 (Table 3). Amino acid sequences are shown in Table A-6.

Multivalent ISVDs were expressed in *Pichia pastoris. P. pastoris* NRRL Y-11430 cells containing ISVD constructs of interest were grown in BGCM medium. Subsequently, medium was switched to BMCM and the constructs were further grown and induced by stepwise addition of methanol. The cells were spun down and the supernatant (containing the secreted ISVD) was collected.

Multivalent ISVDs were purified on protein A resin followed by a desalting step and if necessary, preparative SEC in D-PBS.

TABLE 3

Sample ID and description of trispecific ISVDs constructs

| Sample ID | SEQ ID NO | Description |
|---|---|---|
| A022600027 | 49 | T0170056G05-35GS-A0226018C08-35GS-ALBX00001 |
| A022600031 | 50 | T0170056G05-35GS-A0226015A08-35GS-ALBX00001 |

6.3 Example 3: T-Cell Dependent Cytotoxicity of Trispecific GPC3 ISVD T-Cell Engagers The trispecific T-cell engagers containing the anti-GPC3 ISVDs (Table 3) were characterized in a T-cell dependent cytotoxicity assay (TDC). HepG2 (ATCC, clone HB8065), a liver cancer cell line with high expression of GPC3, was labelled with Nuclight Green (Essen Bioscience, cat no. 4624) and used as target for T-cell killing in the presence of the trispecific T-cell engager constructs comprising A0226015A08 or A0226018C08 (i.e. constructs A022600031 or A022600027, respectively) or in the presence of a construct with a reference GPC3 binding single domain antibody (Ab1) in the format anti-TCR-35GS-anti-GPC3-35GS-HLE (HLE=half-life extender). To this end, plates (96-well F-bottom, Greiner, cat no 655180) were pre-blocked with 200 L/well assay medium (2 h, 37° C.). Simultaneous addition of each assay component was performed in a total volume of 200 μL/well: (1) 50 μL of diluted/titrated compounds (Nbs; Brefeldin A (Sigma-Aldrich, cat no B7651); (2) 25 μL of diluted HSA (Sigma-Aldrich, cat no A8763-10G) (final concentration: 30 μM); (3) 25 μL of diluted Cytotox Red (Essen Bioscience, cat no 4632) (final concentration: 250 nM) (4) 50 μL of human T-cells (T cells were isolated from buffy coats (Red Cross) using the RosetteSep T cell enrichment cocktail (StemCell, cat no. 15061) and 50 μL of HepG2 Nuclight green (fresh in DNEM, High Glucose, GlutaMAX, Pyruvate, Life Technologies-Gibco, cat no 31966) in a 15:1 ratio. Plates were placed in an IncuCyte ZOOM for readout in all three channels (phase-contrast, green and red) with intervals of 4 or 6 hours, for a total of 72 h.

The tested trispecific GPC3 T-cell engagers induced human T-cell mediated killing of HepG2 Nuclight green in a dose-dependent manner as shown in FIG. 1. The IC50 values and maximum percentage of killing are shown in Table 4.

TABLE 4

IC50 (M) and maximum percentage of killing (%) of the trispecific GPC3 ISVD T-cell engagers in the Incucyte based human TDC HepG2-Nuclight green assay using an effector to target ratio of 15:1, analyzed at 60 h after seeding

| Sample ID | IC50 (M) | Max % of killing |
|---|---|---|
| A022600027 | 8.6E−09 | 80 |
| A022600031 | 1.5E−08 | 75 |
| Ab1 | 1.3E−08 | 40 |

6.4 Example 4: Epitope Binning of GPC3 Binders

Epitope binning of the anti-GPC3 ISVDs was done via flow cytometry allowing periplasmic extracts of the monovalent ISVDs A0226015A08 or A0226018C08 to compete with the ISVDs in the purified trispecific format. To this end, $4\times10^4$ human GPC3 CHO Flp-In cells (reference, see example 1) were incubated with 1/15 and 1/150 dilutions of periplasmic extracts, 150 nM competitor (trispecific ISVD format; oversaturating concentration) and 0.2 μg/mL of monoclonal anti-FLAG® M2 antibody (Sigma-Aldrich, cat nr F1804) and rat anti-mouse APC (BD-Pharmingen, cat no 550874), for 5 h at RT and 300 rpm. The samples were read in the iQue Screener. No competition was observed between A0226015A08 and A0226018C08 revealing that they bind to different, non-overlapping epitopes.

6.5 Example 5: Optimization of Format for GPC3 ISVD T-Cell Engagers

The GPC3 ISVD T-cell engagers in the format described in Table 3, do not reach full efficacy in the T-cell dependent cytotoxicity (TDC) HepG2 Nuclight green assay as indicated by the maximum percentage of killing (Example 3). To increase potency and efficacy, trispecific constructs were generated in which the anti-GPC3 ISVDs were combined with a sequence optimized variant of the anti-TCR ISVD T0170056G05, i.e. T017000624, at the N-terminus, an albumin binding ISVD, ALB23002-A (SEQ ID NO: 5 with C-terminal single alanine extension), at the C-terminus and the GPC3 binding ISVD(s) in the central position of the construct (Tables 5 and 6). The optimization encompassed two steps: Step 1—optimization of the linker length between the anti-TCR ISVD and an anti-GPC3 ISVD (trispecific trivalent format); Step 2—generation of biparatopic GPC3 ISVD T-cell engagers (trispecific tetravalent format) and optimization of the linker length between the two GPC3 binding ISVDs. Amino acid sequences are shown in Table A-6.

The generated formats were tested int TDC HepG2 Nuclight green assay, as described in Example 3. Analysis for the Step 1 and Step 2 formats was performed 72 h or 60 h after seeding, respectively.

Tables 5 and 6 show the IC50 values and the maximum % killing for the different formats in Step 1 and Step 2, respectively, of format optimization in the TDC HepG2 Nuclight green assay.

In Step 1, the trispecific GPC3 ISVD T-cell engagers showed cell tumor killing with increased efficacy (increased maximum killing) with decreasing length of the linker between the anti-TCR ISVD and anti-GPC3 ISVD, from 72% (35GS linker) to 94% (AAA linker) (FIG. 2). In Step 2, GPC3 biparatopic T-cell engagers were tested for which A0226018C08 and A0226015A08 were combined in the same construct and placed in different orientations and with different linker lengths between the two building blocks. Here, no impact of the tested variables on efficacy was observed (FIG. 3).

TABLE 5

IC50 (M) and maximum percentage of killing (%) of the trispecific GPC3 ISVD T-cell engagers in the Incucyte based human TDC HepG2-Nuclight green assay using an effector to target ratio of 15:1, analyzed at 72 h after seeding

| Step | Sample ID | SEQ ID NO | Description | IC50 (M) | Max % Killing |
|---|---|---|---|---|---|
| 1 | A022600096 | 51 | T017000624-35GS-A0226018C08-35GS-ALB23002-A | 1.4E−09 | 72 |
| | A022600105 | 55 | T017000624-20GS-A0226018C08-35GS-ALB23002-A | 2.14E−09 | 85 |
| | A022600104 | 54 | T017000624-9GS-A0226018C08-35GS-ALB23002-A | 2.13E−09 | 90 |
| | A022600103 | 53 | T017000624-5GS-A0226018C08-35GS-ALB23002-A | 2.04E−09 | 92 |
| | A022600102 | 52 | T017000624-AAA-A0226018C08-35GS-ALB23002-A | 1.72E−09 | 94 |

TABLE 6

IC50 (M) and maximum percentage of killing (%) of the trispecific GPC3 ISVD T-cell engagers in the Incucyte based human TDC HepG2-Nuclight green assay using an effector to target ratio of 15:1, analyzed at 72 h after seeding

| Step | Sample ID | SEQ ID NO | Description | IC50 (M) | Max % Killing |
|---|---|---|---|---|---|
| 2 | A022600103 | 53 | T017000624-5GS-A0226018C08-35GS-ALB23002-A | 5.43E−10 | 90 |
| | A022600122 | 56 | T017000624-5GS-A0226018C08-35GS-A0226015A08-35GS-ALB23002-A | 4.45E−10 | 92 |
| | A022600131 | 57 | T017000624-5GS-A0226018C08-20GS-A0226015A08-35GS-ALB23002-A | 4.44E−10 | 94 |
| | A022600132 | 58 | T017000624-5GS-A0226018C08-9GS-A0226015A08-35GS-ALB23002-A | 7.02E−10 | 91 |
| | A022600133 | 59 | T017000624-5GS-A0226015A08-35GS-A0226018C08-35GS-ALB23002-A | 4.08E−10 | 92 |
| | A022600134 | 60 | T017000624-5GS-A0226015A08-20GS-A0226018C08-35GS-ALB23002-A | 5.28E−10 | 92 |
| | A022600135 | 61 | T017000624-5GS-A0226015A08-9GS-A0226018C08-35GS-ALB23002-A | 6.11E−10 | 91 |

To evaluate the ability to kill a liver cancer cell line expressing medium levels of GPC3 compared to the high levels of HepG2, a TDC Huh7 assay was performed. To this end, the xCELLigence® (Acea) system was used. Firstly, 96-well E-plates (Acea, Cat no 5232368001) containing 50 µL of assay medium with a 4× concentration (120 µM) of Alburex 20 Human serum albumin (CSL Behring, Cat no 2160-979) (final assay concentration 30 µM) were placed inside the xCELLigence© for background measurement. After background measurement, simultaneous addition of each assay component was performed to a total volume of 200 µL/well: (1) 50 µL of diluted/titrated compounds; (2) 50 µL of single-cell suspensions of Huh7 (HSRRB, clone JCRB0403); (3) 50 µL of single suspensions of effector cells (human T-cells, obtained as described in Example 3) to match an effector:target ratio of 15:1. Plates were placed in the xCELLigence® with 400 sweeps at 15-minute intervals. At the appropriate timepoint (ca. 60 h), cell indexes (CI) were analyzed, where a CI of 0 represented 100% killing.

In a 3$^{rd}$ Step of GPC3 T-cell engager format optimization the anti-TCR ISVD T017000624 was substituted by the sequenced optimized variant T017000680 (TCE01, SEQ ID NO: 2) in the trivalent and tetravalent formats. Potency and efficacy was assessed in the HepG2 and Huh7 TDC assay, as described above. The formats, their description and functionality is summarized in Table 7. Data is depicted in FIG. 4. The third step of format optimization resulted in a further small increase in efficacy across constructs. From this exercise GPC3 T-cell engager formats A022600167 and A022600168 were taken forward.

Step 4 of GPC3 T-cell engager format optimization consisted in changing the orientation of the anti-TCR ISVD with the anti-GPC3 ISVD, but this had an influence on potency on efficacy (Table 8, FIG. 5). For the trivalent format the killing efficacy was lost. For the tetravalent formats functionality could still be observed, be it with a decrease in potency and efficacy; the killing efficacy decreased by 20% on HepG2 Nuclight green and by 40% on Huh7.

Moreover, changing orientation of anti-GPC3 ISVD with anti-Albumin ISVD also had an influence on efficacy of killing. From this exercise no changes were made to GPC3 T-cell engager formats A022600167 and A022600168.

Step 5 of GPC3 T-cell engager format optimization consisted in varying the linker lengths (Table 9, FIG. 6). Decreasing the linker length before the anti-Albumin ISVD in the trivalent format resulted in decreased efficacy. This is not seen in the tetravalent format, so in this case a choice can be made between 9GS and 35GS linker lengths.

From the set of GPC3 T-cell engager formats A022600167 and A022600168 represent the trispecific trivalent and tetravalent formats with the highest potency and efficacy in the TDC assays. While efficacies are comparable, the trivalent format A022600167 and the tetravalent format A022600168 differ in potency. In the HepG2 TDC assay, A022600167 is 5-fold less potent than A022600168 while in the Huh7 TDC assay the difference increases to 50-fold.

TABLE 7

Step 3 of GPC3 ISVD T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600103 | 53 | T017000624-5GS-A0226018C08-35GS-ALB23002-A | 1.23E−09 | 96 | 7.11E−09 | 71 |
| A022600167 | 62 | TCE01-5GS-A0226018C08-35GS-ALB23002-A | 1.92E−09 | 98 | 8.61E−09 | 91 |

TABLE 7-continued

Step 3 of GPC3 ISVD T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600122 | 56 | T017000624-5GS-A0226018C08-35GS-A0226015A08-35GS-ALB23002-A | 5.3E−10 | 93 | 2.61E−10 | 101 |
| A022600168 | 63 | TCE01-5GS-A0226018C08-35GS-A0226015A08-35GS-ALB23002-A | 3.67E−10 | 103 | 1.98E−10 | 107 |
| A022600132 | 58 | T017000624-5GS-A0226018C08-9GS-A0226015A08-35GS-ALB23002-A | 6.83E−10 | 83 | 2.9E−10 | 95 |
| A022600175 | 68 | TCE01-5GS-A0226018C08-9GS-A0226015A08-35GS-ALB23002-A | 5.27E−10 | 96 | 5.86E−11 | 99 |

TABLE 8

Step 4 of GPC3 ISVD T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600167 | 62 | TCE01-5GS-A0226018C08-35GS-ALB23002-A | 1.92E−09 | 98 | 8.61E−09 | 91 |
| A022600178 | 69 | A0226018C08-5GS-TCE01-35GS-ALB23002-A | no effect | | no effect | |
| A022600168 | 63 | TCE01-5GS-A0226018C08-35GS-A0226015A08-35GS-ALB23002-A | 3.67E−10 | 103 | 1.98E−10 | 107 |
| A022600169 | 64 | A0226018C08-5GS-TCE01-5GS-A0226015A08-35GS-ALB23002-A | 6.41E−10 | 81 | 1.02E−09 | 61 |
| A022600174 | 67 | TCE01-5GS-A0226018C08-9GS-A0226015A08-9GS-ALB23002-A | 6.73E−10 | 96 | 6.26E−11 | 99 |
| A022600172 | 66 | TCE01-5GS-A0226018C08-9GS-ALB23002-9GS-A0226015A08-A | 6.01E−10 | 81 | 6.70E−11 | 90 |

TABLE 9

Step 5 of GPC3 T-cell engager format optimization. IC50 (M) and maximum percentage of killing (%) of trispecific GPC3 ISVD T-cell engagers in the Incucyte based human TDC HepG2-Nuclight green assay and in the xCELLigence based human TDC Huh7 assay, using an effector to target ratio of 15:1, analyzed at 60 h after seeding

| Sample ID | SEQ ID NO | Description | HepG2 on Incucyte IC50 (M) | HepG2 on Incucyte Max % killing | Huh7 on xCELLigence IC50 (M) | Huh7 on xCELLigence Max % killing |
|---|---|---|---|---|---|---|
| A022600167 | 62 | TCE01-5GS-A0226018C08-35GS-ALB23002-A | 1.92E−09 | 98 | 8.61E−09 | 91 |
| A022600179 | 70 | TCE01-5GS-A0226018C08-9GS-ALB23002-A | 2.92E−09 | 76 | 6.13E−09 | 66 |
| A022600168 | 63 | TCE01-5GS-A0226018C08-35GS-A0226015A08-35GS-ALB23002-A | 3.67E−10 | 103 | 1.98E−10 | 107 |
| A022600170 | 65 | TCE01-5GS-A0226018C08-35GS-A0226015A08-9GS-ALB23002-A | 3.19E−10 | 97 | 1.86E−10 | 103 |
| A022600175 | 68 | TCE01-5GS-A0226018C08-9GS-A0226015A08-35GS-ALB23002-A | 5.27E−10 | 96 | 5.86E−11 | 99 |
| A022600174 | 67 | TCE01-5GS-A0226018C08-9GS-A0226015A08-9GS-ALB23002-A | 6.73E−10 | 96 | 6.26E−11 | 99 |

6.6 Example 6: Assessment of T-Cell Activation Induction in the Presence of Soluble GPC3

GPC3 can be released into circulation in a soluble form, with levels increased in up to 50% of HCC patients. Soluble GPC3 antibody aggregates in circulation could lead to immune complex deposition and related toxicities. Thus, it is important to assess the effect on T cell activation of soluble GPC3 in presence of the GPC3 T-cell engager.

Reported serum levels of GPC3 can vary between 10 to 300 ng/mL, which corresponds to 0.1 to 10 nM. The assessment was done using 1, 10 and 100 nM of soluble GPC3, in the presence of the trispecific GPC3 ISVD T-cell engagers A022600167 and 168, in three ways: (1) Cytotoxicity in the presence of target cells (Huh-7) and soluble GPC3 (FIG. 7A): no additional killing was observed compared to in the absence of soluble GPC3; (2) CD69 upregulation in presence of target cells and soluble GPC3 (FIG. 7B): no additional T-cell activation was observed compared to in the absence of soluble GPC3; (3) CD69 upregulation in absence of target cells and presence of soluble GPC3 (FIG. 7C): no T-cell activation was seen. The risk of toxicity effects due to increased serum levels of soluble GPC3 is therefore considered low.

The cytotoxicity assay on Huh-7 was performed as described in Example 5. CD69 expression on T-cells was determined by flow cytometry using an anti-CD69 antibody (BD Pharmigen, cat no. 557050) and anti-mouse IgG1 antibody (BD Pharmigen, cat no. 556650).

6.7 Example 7: GPC3 Mediated T-Cell Engager Internalization

GPC3 is known to internalize and its internalization rate may have an impact on the efficacy of the compound. The internalization rate and the GPC3 receptor density in the presence of the trispecific GPC3 ISVD T-cell engagers equivalent to A022600167 and A022600168 and of a reference CD3-GPC3 bispecific T-cell engager antibody (Ab2) (Table 10) were assessed in Huh-7 cells over a time course of 48 h.

Internalization was determined by labeling A022600167 and A022600168 and Ab2 with pHAb (Promega, cat no. G9841), a pH sensor dye with low fluorescence at pH>7 and a strong increase in fluorescence as the pH of the solution becomes acidic. For this labeling, formats with an extra -GGC at the C-terminus were generated in order to have a single site incorporation of the label (Table 10): A022600167-GGC corresponds to A022600370, A022600168-GGC corresponds to A022600372 and as a control a format without a GPC3 ISVD, A022600373 was generated. The assay was read on a BD FACSArray with a yellow laser (pHAb: excitation maximum at 532 nm, emission maximum at 560 nm). The internalization rate was determined by quantifying the internalization at 37° C. at different timepoints (0.5 h, 3 h, 24 h and 48 h) compared to 4° C. at 0.5 h (Table 10, FIG. 8A).

The receptor expression was determined using a fixed concentration of a 3×FLAG-His6-tagged ISVD (20 nM) that binds to a different GPC3 epitope than A02260018C08 and A02260015A08 in combination with APC labelled anti-FLAG for detection on a BD FACSArray with a red laser (Table 10, FIG. 8B).

The internalization rate was calculated as the slope of the kinetic curve with arbitrary units. The trispecific GPC3 ISVD T-cell engagers show a slower internalization rate than the reference bispecific T-cell engager Ab2. Internalization of the GPC3 ISVD T-cell engagers is GPC3 mediated as the control format without a GPC3 binding ISVD (A022600373) does not show internalization. No decrease of GPC3 cell surface expression within 48 h was observed (Table 10, FIG. 8).

TABLE 10

Internalization rate of pHAb labelled trispecific GPC3 T-cell engagers

| Sample ID | SEQ ID NO | Description | pHAb degree of labeling | Internalization rate (normalized slope n = 2) |
|---|---|---|---|---|
| A022600370 | 71 | TCE01-5GS-A0226018C08-35GS-ALB23002-GGC | 1 | 194 |
| A022600372 | 72 | TCE01-5GS-A0226018C08-35GS-A0226015A08-35GS-ALB23002-GGC | 1 | 297 |
| A022600373 | 73 | TCE01-20GS-ALB23002-GGC | 1 | 2 |
| Ab2 | — | — | 1.4 | 597 |

6.8 Example 8: GPC3 Expression Profiling of Cancer Cell Lines and Correlation with Functionality of GPC3 T-Cell Engagers GPC3 protein expression levels for a panel of cancer cell lines was determined both by immunocytochemistry (ICC) and using the QIFIKIT® (Dako, Cat no K0078) according to the manufacturer's instructions (Table 11). Additionally, immunohistochemistry (IHC) was performed on hepatocellular carcinoma and normal kidney samples.

ICC and IHC was performed using the Ventana discovery XT robot (Ventana medical system, Roche). The cell lines and the tissue samples were first fixed on 4% formalin and subsequently paraffin embedded. After deparaffinization, cells were conditioned with buffer CC1 standard (Ventana, Cat no 950-124) at a temperature of 95° C. for 48 minutes, followed by a blocking step of 4 minutes with each of Blocker A and B (Ventana, Cat no 760-104). Mouse monoclonal IgG2a anti-GPC3 antibody (Ventana, Cat no 790-4564) was applied for 60 minutes at room temperature, followed by 4 minutes of fixation with 0.05% Glutaraldehyde in 5M NaCl (Prolabo, Cat no 20879-238). Biotinylated goat anti-mouse IgG2a antibody (Southern Biotech, Cat no 1080-080) at 1/200 dilution in antibody diluent (Ventana; Cat no 760-108) was applied for 32 minutes at room temperature. Detection was performed with the DABMap Kit (Ventana; Cat no 760-124). Sections were counterstained for 4 minutes with Hematoxylin II (Ventana, Cat no 790-2208) and post-counterstained for 4 minutes with bluing agent (Ventana, Cat no 760-2037), followed by deshydratation and mounting with Cytoseal XYL (Richard-Allan Scientific, Cat no 8312-4). Immunohistochemical staining was evaluated by a semi-quantitative assessment of both the intensity of staining of the cells (graded as 0: no staining, 1 (or +): weak, 2 (or ++): moderate; 3 (or +++): strong) and percentage of positive cells in every intensity categories. Histoscore (H-score) was calculated according to following formula:

$$H\text{-}score = 3\times(\text{cell \% with grade 3}) + 2\times(\text{cell \% with grade 2}) + 1\times(\text{cell \% with grade 1}).$$

The range of the possible score was from 0 to 300, as described in literature (Detre et al., J Clin Pathol 1995; 48:876-878 and Lui et al., Journal of Latex Class filed, august 2015, vol 14, No. 8). Determination of H-score in HCC was based on evaluation of membranous expression of GPC3.

Within the panel of cell lines tested, as determined with the QIFIKIT®, Hep-G2 (ATCC, clone HB-8065; 5.2E5 receptors/cell) showed the highest level of expression of GPC3 followed by NCI-H661 (ATCC, clone HTB-183; 3.4E5 receptors/cell) and Huh-7 (HSRRB, clone JCRB0403; 6.8E4 receptors/cell), the latter considered as medium expressing cell line. These cell lines originated from liver and lung cancers which are relevant GPC3 expressing solid tumors. The low or very low GPC3 expressing cell lines, which did not show any staining in ICC, were MKN-45 (DSMZ, clone ACC409; 1.5E4 receptors/cell), NCI-H23 (ATCC, clone CRL-5800; 2.6E3 receptors/cell), BxPC-3 (ATCC, clone CRL-1687; 1.5E3 receptors/cell) and NCI-H292 (ATCC, clone CRL-1848; 6E2 receptors/cell).

For comparison between the cancer cell lines and patient tumour samples, the H-scores were determined for both. GPC3 positive cancer cell lines in ICC, i.e. Huh-7, NCI-H661 and HepG2, showed H-scores of superior to 80 (Table 11), which corresponds to the average H-score determined for the GPC3 positive hepatocellular carcinoma (HCC) samples in IHC of 80.75 (Table 12). Normal kidney GPC3 positive samples show an average H-score of 0.75 (Table 12) while the cancer cell lines MKN-45, NCI-H23, BxPC-3 and NCI-H292 were negative for GPC3 staining (Table 11). These cell lines were taken as representatives of GPC3 normal-like expression level cells.

To assess the functionality of the trispecific GPC3 T-cell engagers with the same panel of cancer cell lines, TDC assays were performed using the xCELLigence system, as described in Example 5; results are shown in Table 13 and FIG. 9. For the GPC3 high expressing cell lines, Hep-G2 and NCI-H661, the trispecific GPC3 ISVD T-cell engagers A022600167 and A022600168 show similar potency (NCI-H661) and 10-fold lower potency (Hep-G2), compared to the bispecific T-cell engager Ab2. For the medium expressing cell line, Huh-7, A022600168, the tetravalent format with biparatopic binding to GPC3, shows the same potency as Ab2, while the potency of the trivalent format A022600167 is 10-fold lower. For the GPC3 low expressing cell lines, MKN-45 and BxPC-3, Ab2 shows a potency in the nM range, while the trispecific GPC3 ISVD T-cell engagers show no killing effect. For the very low GPC3 expressing cell line, NCI-H292, none of the compounds show an effect. The T-cell engager lacking a GPC3 binding ISVD, T017000698, does not show any killing effect on any cell line, confirming the GPC3 specific effect of the trispecific GPC3 T-cell engagers.

In conclusion, Ab2 is a potent T-cell engager able to kill cancer cell lines with GPC3 expression levels as low as a thousand receptors per cell and H-score 0. In comparison, the trispecific T-cell engager formats potently kill high and medium GPC3 expressing cancer cell lines with H-scores similar to HCC and large cell lung cancer samples while sparing cell lines expressing GPC3 levels below ten thousand receptors per cell and with H-scores below the average of normal kidney samples.

TABLE 11

GPC3 expression levels of different cancer cell lines.

| Cell line | Cancer tissue | Expression RNA FPKM | Expression protein #GPC3/cell | Expression protein ICC (H-score) |
|---|---|---|---|---|
| Hep-G2 | Liver | 2253 | 619006 | 70%+++, 25%++ (260) |
| NCI-H661 | Lung | 237 | 346756 | 40%++ (80) |
| Huh-7 | Liver | 549 | 78027 | 20%++, 40%+ (80) |
| MKN-45 | Stomach | 20.9 | 7453 | 0 |
| NCI-H23 | Lung | 3.17 | 2255 | 0 |
| BxPC3 | Pancreas | 5.3 | 1332 | 0 |
| NCI-H292 | Lung | 0.04 | 452 | 0 |

TABLE 12

GPC3 H-score determined by immunohistochemistry on Hepatocellular carcinoma and normal kidney samples (based on evaluation of membranous expression of GPC3).

| | Total cases | H-score | Total GPC3+ cases | H-score |
|---|---|---|---|---|
| HCC | 288 | 52.22 | 187 | 80.75 |
| Normal kidney | 35 | 0.17 | 8 | 0.75 |

TABLE 13

IC50 (M) of the GPC3 T-cell engagers in the xCELLigence based human TDC assay on different tumor cell lines expressing decreasing expression levels of GPC3 using an effector to target ratio of 15:1: HepG2 analysed at 60 h, NCI-H661 analysed at 75 h, Huh-7 analysed at 60 h, MKN-45 analysed at 65 h, BxPC-3 analysed at 65 h, NCI-H292 analysed at 60 h.

| Sample ID | SEQ ID NO | Description | Hep-G2 | NCI-H661 | Huh-7 | MKN-45 | BxPC-3 | NCI-H292 |
|---|---|---|---|---|---|---|---|---|
| A022600167 | 62 | TCE01-5GS-A0226018C08-35GS-ALB23002-A | 9.2E−11 | 1.8E−10 | 4.7E−10 | n.a. | n.a. | n.a. |
| A022600168 | 63 | TCE01-5GS-A0226018C08-35GS-A0226015A08-35GS-ALB23002-A | 7.3E−11 | 1.4E−10 | 2.4E−11 | n.a. | n.a. | n.a. |
| T017000698 | 74 | TCE01-9GS-ALB23002-A | n.a. | n.a. | n.a. | n.a. | n.a. | n.a. |
| Ab2 | — | Bispecific CD3-GPC3 | 1.1E−11 | 2.8E−11 | 3.0E−11 | 2.0E−09 | 3.6E−09 | n.a. |

n.a. = not available 6.9 Example 9: Sequence Optimization of A0226015A08 and A0226018C08

The ISVDs A0226015A08 and A0226018C08 were further sequence optimized.

Sequence optimization involves replacing one or more specific amino acid residues in the sequence in order to improve one or more (desired) properties of the ISVDs.

Some examples of such sequence optimization are mentioned in the further description herein and for example include, without limitation:

1) Substitutions in parental wild type ISVD sequences to yield ISVD sequences that are more identical to the human VH3-JH germline consensus sequences, a process called humanization. To this end, specific amino acids, with the exception of the so-called hallmark residues, in the FRs that differ between the ISVD and the human VH3-JH germline consensus are altered to the human counterpart in such a way that the protein structure, activity and stability are kept intact.
2) Substitutions towards the llama germline to increase the stability of the ISVD, which is defined as camelisation. To this end, the parental wild type ISVD amino acid sequence is aligned to the llama IGHV germline amino acid sequence of the ISVD (identified as the top hit from a BlastP analysis of the ISVD against the llama IGHV germlines).
3) Substitutions that improve long-term stability or properties under storage, substitutions that increase expression levels in a desired host cell or host organism, and/or substitutions that remove or reduce (undesired) post-translational modification(s) (such as glycosylation or phosphorylation), again depending on the desired host cell or host organism.
4) Mutations on position 11 towards Val and on position 89 towards Leu (according to Kabat) to minimize the binding of any naturally occurring pre-existing antibodies.

Sequence optimization of A0226015A08 yielded the final sequence optimized variant A022600314, which comprises 13 amino acid substitutions (i.e. L11V, A14P, V23A, P40A, D52cE, N54Y, D73N, K76N, D79Y, K83R, G88A, V89L, F91Y) (Table 14) compared to the parental ISVD clone A0226015A08.

Sequence optimization of A0226018C08 yielded two sequence optimized variants, A022600345, which comprises 8 amino acid substitutions (i.e. L11V, V23A, G54A, R60A, E81Q, T82aN, N83R, V89L) and A022600351, which comprises 8 amino acid substitutions (i.e. L11V, V23A, G54K, R60A, E81Q, T82aN, N83R, V89L) (Table 14), compared to the parental ISVD clone A0226018C08.

TABLE 14

Amino acid sequences of the sequence optimized versions of A0226015A08 and A0226018C08.

| Sample ID | SEQ ID NO | Description | Sequence |
|---|---|---|---|
| A022600314 | 75 (same as 4) | A0226015A08(L11V, A14P, V23A, P40A, D52cE, N54Y, D73N, K76N, D79Y, K83R, G88A, V89L, F91Y) | EVQLVESGGGVVQPGGSLRLSCAASGSIFRSVFSSSTMEWYRQAPGKKRELVARIAPGEGTYYGALYADSVKGRFTISRDNAKNTVYLQMNSLRPEDTALYYCASGVAWGQGTLVTVSS |
| A022600345 | 76 | A0226018C08(L11V, V23A, G54A, REDA, E81Q, T82aN, N83R, V89L) | EVQLVESGGGVVQPGGSLRLSCAASGFTFSSFAMTWVRRPPGKGLEWVATITNAGVTSYADSVKGRFTISRDNAKNTLYLQMNSLRPEDTALYICANARRTGPRAPTDIGSYRGQGTLVTVSS |
| A022600351 | 77 (same as 3) | A0226018C08(L11V, V23A, G54K, R60A, E81Q, T82aN, N83R, V89L) | EVQLVESGGGVVQPGGSLRLSCAASGFTFSSFAMTWVRRPPGKGLEWVATITNKGVTSYADSVKGRFTISRDNAKNTLYLQMNSLRPEDTALYICANARRTGPRAPTDIGSYRGQGTLVTVSS |

Properties of the sequence optimized variants in comparison to the parental ISVD were assessed as follows:

Variants were evaluated for binding to HepG2, Huh-7 and CHO Flip-In cyno-GPC3 cells by flow cytometry, as described in Example 1.

Thermal stability of the variants was tested in a thermal shift assay (TSA) using a Lightcycler (Roche). In this assay, the parental ISVDs and their variants are incubated at different pH in the presence of SYPRO™ orange and a temperature gradient is applied. When an ISVD starts denaturing, SYPRO™ orange binds leading to an increase in fluorescence, allowing determination of the melting temperature (Tm) for a certain pH.

Results are summarized in Table 15 and Table 16.

TABLE 15

Results of the analysis of the sequence optimization variant A0226000314 of the parental ISVD A0226015A08.

| Sample ID | Mutations | EC50 (M) HepG2 | EC50 (M) Huh-7 | EC50 (M) CHO-cGPC3 | Tm (° C.) at pH 7 TSA |
|---|---|---|---|---|---|
| A0226015A08 | WT | 7.5E−09 | 6.6E−09 | 7.8E−09 | 70 |
| A022600314 | L11V, A14P, V23A, P40A, D52cE, N54Y, D73N, K76N, D79Y, K83R, G88A, V89L, F91Y | 1.6E−08 | 9.3E−09 | 1.2E−08 | 65 |

TABLE 16

Results of the analysis of the sequence optimization variants A022600345 and A0226000351 of the parental ISVD A0226018C08.

| Sample ID | Mutations | EC50 (M) HepG2 | EC50 (M) Huh-7 | EC50 (M) CHO-cGPC3 | Tm (° C.) at pH 7 TSA |
|---|---|---|---|---|---|
| A0226018C08 | WT | 9.15E−10 | 6.96E−10 | 4.9E−10 | 67 |
| A022600345 | L11V, V23A, G54A, R60A, E81Q, T82aN, N83R, V89L | 3.91E−10 | 2.76E−10 | 1.5E−10 | 75 |
| A022600351 | L11V, V23A, G54K, R60A, E81Q, T82aN, N83R, V89L | 4.31E−10 | 4.77E−10 | 2.1E−10 | 74 |

Compared with the parental ISVD A0226015A08, A022600314 exhibited a decrease in binding potency for the different cell lines expressing human GPC3 or cyno GPC3 of less than 2-fold. Tm decreased slightly by 5° C. and within acceptable values. The % framework identity in the framework regions compared to the reference hIGHV3-23SO/IGHJ4 for A022600314 is 88.8% based on the AbM definition (see Antibody Engineering, Vol 2 by Kontermann & Dübel (Eds), Springer Verlag Heidelberg Berlin, 2010) and 85.1% based on the Kabat definition.

Compared with the parental ISVD A0226018C08, the binding potency of variants A022600345 and A022600351 for the different cell lines expressing human GPC3 or cyno GPC3 is increased 2-fold. The Tm for variants A022600345 and A022600351 increased to 75 and 74° C., respectively. The % framework identity in the framework regions compared to the reference hIGHV3-23SO/IGHJ4 for both, A022600345 and A022600351, is 89.9% based on the AbM definition and 89.7% based on the Kabat definition.

6.10 Example 10: Generation of Trispecific Sequence Optimized GPC3 ISVD T-Cell Engager The sequence optimized GPC3 ISVDs A022600314 (optimized variant of A0226015A08), A022600345 and A022600351 (optimized variants of A0226018C08) were used for the generation of five trispecific GPC3 T-cell engager formats for assessment of optimal combination of building blocks and linker length as described in Table 17.

TABLE 17

Selection of different trispecific GPC3 ISVD T-cell engager formats evaluated

| Sample ID | SEQ ID NO | Description |
|---|---|---|
| A022600427 | 81 | TCE01-5GS-A022600345-9GS-A022600314-9GS-ALB23002-A |
| A022600424 | 1 | TCE01-5GS-A022600351-9GS-A022600314-9GS-ALB23002-A |
| A022600425 | 79 | TCE01-5GS-A022600314-20GS-A022600345-9GS-ALB23002-A |
| A022600426 | 80 | TCE01-5GS-A022600314-20GS-A022600351-9GS-ALB23002-A |
| A022600412 | 78 | TCE01-5GS-A022600345-20GS-ALB23002-A |

The five selected formats were tested in the xCELLingence based TDC assay with different cancer cell lines for functionality, as described in Example 8. Results are depicted in Table 18. For high and medium GPC3 expressing cell lines HepG2, NCI-H661 and Huh-7, higher potencies were obtained for the tetravalent formats compared to the trivalent format. For high GPC3 expressing cell line NCI-H661, tetravalent formats A022600424 and A022600427 are more potent than A022600425 and A022600426. For the GPC3 low expressing cell lines, NCI-H23 and BxPC-3, the lack of a killing effect was confirmed for all trispecific GPC3 ISVD T-cell engager formats.

FIG. 10 shows the dose-dependent killing curves for the xCELLingence based TDC assay, exemplified by cell lines NCI-H661 and BxPC-3, using three different T-cell donors for the five selected ISVD formats.

TABLE 18

IC50 (M) of GPC3 T-cell engagers in the xCELLigence based human TDC assay on different tumor cell lines using an effector to target ratio of 15:1 and analyzed at 60 h.

| Sample ID | IC50 (M) HepG2 | IC50 (M) NCI-H661 | IC50 (M) Huh-7 | IC50 (M) NCI-H23 | IC50 (M) BxPC-3 |
|---|---|---|---|---|---|
| A022600427 | 1.03E−10 | 1.00E−10 | 1.37E−10 | no fit | no fit |
| A022600424 | 1.15E−10 | 1.14E−10 | 1.16E−10 | no fit | no fit |
| A022600425 | 1.11E−10 | 2.59E−10 | 1.58E−10 | no fit | no fit |
| A022600426 | 1.25E−10 | 2.64E−10 | 1.09E−10 | no fit | no fit |
| A022600412 | 3.82E−10 | 6.18E−10 | 1.53E−09 | na | no fit |
| Ab2 | 1.49E−11 | 4.60E−11 | 8.41E−11 | 1.28E−09 | 1.09E−09 |

na = not available;
no fit = no curve fit obtained,
IC50 estimated as >1E−7M

Binding of pre-existing antibodies to the 5 selected formats was assessed using a SPR-based setup (Example 14). FIG. 11 shows that for all formats only low levels of pre-existing antibody binding were observed, compatible with developability requirements.

Performance in *Pichia pastoris* was assessed for the 5 formats, focusing on product titer and purity during upstream processing (USP) at 5 L fermentor scale, as well as on yield, after downstream processing (DSP) (Table 19). A022600424 and A022600426 were identified as preferred ISVD development candidates combining low percentage of high molecular weight (HMW) species, low percentage of variants on RPC with a high titer and best overall DSP yield.

TABLE 19

Performance of the 5 selected ISVD based GPC3 T-cell engager formats in Pichia.

| Sample ID | Titer (g/L) | Analytical SEC (% HMW) | RPC (% Post-peaks) | DSP yield (total %) |
|---|---|---|---|---|
| A022600412 | 3.9 | 5.4 | 3.3 | 26 |
| A022600424 | 4.9 | 1.8 | 1.7 | 45 |
| A022600425 | 5.6 | 6.3 | 2.7 | 24 |
| A022600426 | 5.4 | 2.4 | 3.3 | 32 |
| A022600427 | 4.7 | 5.1 | 1.4 | 32 |

Based on the best combination of GPC3 driven killing potency, reduced binding to pre-existing antibodies, and performance in *Pichia*, A022600424 was selected as development candidate.

6.11 Example 11: Binding and Affinity of A022600424 to GPC3, TCRab and Serum Albumin The affinity, expressed as the equilibrium dissociation constant ($K_D$), of A022600424 towards human and cyno GPC3 (R&D Systems, cat no 2119-GP and in house produced (accession number P51654, Q3-R358, S359-H559), respectively), human and cyno TCRab (both in house produced, where alpha and beta chains extracellular domains are fused to a zipper peptide for dimerization; accession numbers: human alpha chain P01848, human beta chain P01850; predicted sequence of cyno alpha chain is identical to human, predicted sequence of cyno beta chain differs in 4 aa: A125V, E136V, V167M, S177F) and human, cyno and mouse serum albumin (Sigma cat no A8763, in house produced from animal tissue, DivBioScience cat no IMSA, respectively) was quantified by surface plasmon resonance (SPR) using a ProteOn XPR36.

Recombinant GPC3 proteins were captured on a GLC Sensor Chip (Biorad) immobilized with THE anti-His antibody (Genscript, cat no ABIN387699) via amine coupling, using EDC and NHS chemistry (running buffer: HBS-EP+, pH7.4). Purified ISVDs were injected for 2 minutes (flow rate 45 μL/min) at different concentrations (between 0.3 nM and 1000 nM) and dissociation was followed for 900 s. Regeneration was performed by injecting 10 mM Glycine-HCl (pH 1.5) for 1 minute (flow rate 45 μL/min). Data was double referenced by subtracting a reference ligand lane and a blank buffer injection. Processed sensorgrams were analyzed based on the 1:1 interaction model (Langmuir binding model) using ProteOn Manager 3.1.0 (Version 3.1.0.6) software.

Recombinant TCR proteins were immobilized on a GLC Sensor Chip (Biorad) via amine coupling, using EDC and NHS chemistry (running buffer: HBS-EP+, pH 7.4). Purified ISVDs were injected for 2 minutes (flow rate 45 μL/min) at different concentrations (between 0.2 nM and 200 nM) and dissociation was followed for 900 s. Regeneration was performed by injecting 3 M $MgCl_2$ for 3 minutes (flow rate 90 μL/min). Data was double referenced by subtracting a reference ligand lane and a blank buffer injection. Processed sensorgrams were analyzed based on the 1:1 interaction model (Langmuir binding model) using ProteOn Manager 3.1.0 (Version 3.1.0.6) software.

Serum albumin proteins were immobilized on a GLC Sensor Chip (Biorad) via amine coupling, using EDC and NHS chemistry (running buffer: HBS-EP+, pH 7.4). Purified ISVDs were injected for 2 minutes (flow rate 45 μL/min) at different concentrations (between 0.24 nM and 500 nM) and dissociation was followed for 900 s. Regeneration was performed by injecting 10 mM Glycine-HCl (pH 1.5) for 47 seconds (flow rate 100 μL/min). Data was double referenced by subtracting a reference ligand lane and a blank buffer injection. Processed sensorgrams were analyzed based on the 1:1 interaction model (Langmuir binding model) using ProteOn Manager 3.1.0 (Version 3.1.0.6) software.

The results (Table 20) demonstrate that A022600424 binds human and cyno GPC3 with high affinity.

TABLE 20

Binding affinities to human and cyno GPC3, human and cyno TCRab and human, cyno and mouse serum albumin.

| Antigen | Sample ID | KD (M) human | KD (M) cynomolgus | KD mouse |
|---|---|---|---|---|
| GPC3 | A022600424 | <5.6E−12 | <5.9E−12 | n.a. |
| | Ab2 | 1.8E−09 | 1.7E−09 | n.a. |
| TCRab | A022600424 | 6.3E−09 | 5.4E−09 | n.a. |
| | T017000698 | 8.5E−09 | 1.1E−08 | n.a. |
| Serum albumin | A022600424 | 8.3E−10 | 3.3E−10 | 6.9E−09 |
| | ALB223 | 8.8E−10 | 5.7E−10 | 5.3E−09 |

n.a. = not available

Binding of A022600424 to cell expressed human and cyno GPC3 was assessed by flow cytometry for CHO-Flp-In cells overexpressing human and cyno GPC3, as well as Huh-7 cells, yielding EC50 values between 1 and 2 nM (Table 21).

A022600424 was evaluated for binding to human and cyno T cells in competition with TCRab binding monovalent ISVDs T017000624 and T017000623 (T0170056G05 variants) respectively, at EC30 concentrations. T cells (human T cells obtained as described in Example 3 and cyno T cells purchased from LPT laboratory, Germany) were thawed and counted on the day of the assay and diluted to a concentration of 1E+06 cells/mL, before adding 75 μL to the wells of a V-bottom 96-well plate (Greiner, cat no 651180). Cells were washed once with cold FACS buffer, before adding 25 μL Nb and 25 μL competitor to the wells. T017000624 was diluted to a 2× concentration of 4E-08 M (2E-08 M in well), T017000623 was diluted to a 2× concentration of 1E-07 M (5E-08 M in well) and A022600424 was diluted to final concentrations in the wells ranging between 8 μM and 7.8 nM. Cells were resuspended and plates were incubated at 4° C. for 90 minutes, after which plates were washed twice in cold FACS buffer. Cells were resuspended in 50 μL 1/1000 diluted Monoclonal ANTI-FLAG® M2 (Sigma Aldrich, cat no F1804) in FACS buffer and incubated at 4° C. for 30 minutes. Plates were washed twice in cold FACS buffer. Cells were resuspended in 50 μL 1/100 diluted Allophycocyanin-conjugated AffiniPure Goat Anti-Mouse IgG (subclasses 1+2a+2b+3), Fc Fragment Specific (Jackson Immunoresearch, cat no 115-135-164) in FACS buffer and incubated at 4° C. for 30 minutes. Plates were washed twice in cold FACS buffer. Cells were resuspended in 55 μL 1/1000 diluted Propidium Iodide (Sigma-Aldrich, cat no P4170) in FACS buffer before acquiring data on the MACSQuant X (Miltenyi biotec).

The results are shown in Table 21. A022600424 binds with approx. 200 nM affinity to both, human and cyno T-cells.

TABLE 21

Binding assessment of A022600424 to cell expressed human and cyno GPC3 and human and cyno TCRab.

| Antigen | Sample ID | CHO huGPC3 EC50 (M) | CHO cyGPC3 EC50 (M) | Huh-7 EC50 (M) |
|---|---|---|---|---|
| GPC3 (binding FACS) | A022600424 | 1.82E−09 | 1.11E−09 | 1.25E−09 |
| | Ab2 | 1.69E−08 | 5.4E−09 | 5.2E−09 |
| | | Primary hu T cells IC50 (M) | | Primary cy T cells IC50 (M) |

TABLE 21-continued

Binding assessment of A022600424 to cell expressed human and cyno GPC3 and human and cyno TCRab.

| | | | |
|---|---|---|---|
| TCRab (competition FACS) | A022600424 | 1.7E−07 | 2.5E−07 |
| | T017000698 | 1.9E−07 | 2.5E−07 |

To assess A022600424 functionality with cyno T-cells, a xCELLigence based TDC assay on Huh-7 was performed using cyno T-cells (LPT laboratory, Germany), as described in Example 8. IC50 values for cyno and human T cells were found to be comparable (Table 22).

TABLE 22

Functionality of A022600424 using cynomolgus T-cells in the xCELLigence based TDC assay on Huh-7, with an effector to target ratio of 15:1 and analyzed at 60 h.

| Sample ID | Primary hu T cells IC50 (M) | Primary cy T cells IC50 (M) |
|---|---|---|
| A022600424 | 7.59E−11 | 2.29E−10 |
| Ab2 | 7.88E−11 | 3.57E−11 |

6.12 Example 12: Selectivity of A022600424 for Binding to GPC3

Absence of A022600424 binding to family members of GPC3, namely GPC1, GPC2, GPC5 and GPC6, was assessed by ELISA and to GPC4 by SPR (Proteon XPR36).

Human GPC1 (R&D systems, cat no 4519-GP), human GPC2 (R&D systems, cat no 2304-GP), human GPC3 (R&D systems, cat no 2119-GP), human Glypican-5 (R&D systems, cat no 2607-G5) and human Glypican-6 (R&D systems, cat no 2845-GP) were directly coated overnight at 4° C. (2 μg/mL, 1×PBS buffer) on a 384-well HB SpectraPlate (PerkinElmer). The following day the plate was washed 6 times (AquaMax microplate washer, Molecular devices) and blocked with 1×PBS+1% Casein for 2 hours at room temperature. After an additional 6 wash steps A022600424 (1×PBS, 0.1% casein, 0.05% TWEEN 20) was added to the plate and incubated at room temperature for 1 hour. Next, the samples were removed, followed by 6 wash steps and anti-ISVD mAb ABH0077 was added at 17 nM final concentration (1×PBS, 0.1% casein, 0.05% TWEEN 20) during 1 hour at room temperature. The plate was washed again 6 times and goat anti-mouse IgG polyclonal antibody conjugated to HRP (Abcam, cat no ab97040) (1/1250 dilution; 1×PBS, 0.1% casein, 0.05% TWEEN 20) was applied to the plate for 1 hour at room temperature. After 6 final wash steps the es(HS)TMB substrate (SDT) was added and the reaction stopped by addition of 1 M HCl after 10 minutes. The absorbance of the plate was measured at wavelengths 450 and 620 nm on the Clariostar instrument (BMG LABTECH) and the $OD_{450}$-$OD_{620}$ calculated and plotted for data analysis.

Recombinant human GPC4/hFc (R&D Systems, cat no 9195-GP) was captured on a GLC Sensor Chip (Biorad) immobilized with mouse anti-human IgG1 (GE Healthcare, cat no BR-1008-39) via amine coupling, using EDC and NHS chemistry (running buffer used: HBS-EP+, pH7.4). Purified ISVDs were injected for 2 minutes (flow rate 45 μL/min) at different concentrations (between 4 nM and 1000 nM) and dissociation was followed for 900 s. Regeneration was performed by injecting 10 mM Glycine-HCl (pH1.5) for 1 minute (flow rate L/min). Data was double referenced by subtracting a reference ligand lane and a blank buffer injection. Processed sensorgrams were analysed based on the 1:1 interaction model (Langmuir binding model) using ProteOn Manager 3.1.0 (Version 3.1.0.6) software.

No binding was detected of A022600424 to any of the GPC3 family members tested.

6.13 Example 13: Reactivity of Human Pre-Existing Antibodies for A022600424

Binding of pre-existing antibodies to A022600424 was assessed for normal human serum (n=96) using the ProteOn XPR36 (Bio-Rad Laboratories, Inc.). PBS/Tween (phosphate buffered saline, pH 7.4, 0.005% Tween20) was used as running buffer and the experiments were performed at 25° C.

A022600424 was captured on the sensor chip via binding of the ALB23002 building block to HSA immobilized on the chip. To immobilize HSA, the ligand lanes of a ProteOn GLC Sensor Chip were activated with EDC/NHS (flow rate 30 μL/min) and HSA was injected at 100 μL/mL in ProteOn Acetate buffer pH4.5 to render immobilization levels of approximately 2900 RU. After immobilization, surfaces were deactivated with ethanolamine HCl (flow rate 30 μL/min).

Subsequently, A022600424 was injected for 2 min at 45 μl/min over the HSA surface to render an ISVD capture level of approximately 800 RU. The samples containing pre-existing antibodies were centrifuged for 2 minutes at 14,000 rpm and supernatants were diluted 1:10 in PBS-Tween20 (0.005%) before being injected for 2 minutes at 45 μl/min followed by a subsequent 400 seconds dissociation step. After each cycle (i.e. before a new ISVD capture and blood sample injection step) the HSA surfaces were regenerated via a 2 minute injection of HCl (100 mM) at 45 μL/min. Sensorgrams showing pre-existing antibody binding were obtained after double referencing by subtracting 1) ISVD-HSA dissociation and 2) non-specific binding to reference ligand lane. Binding levels of pre-existing antibodies were determined by setting report points at 125 seconds (5 seconds after end of association). Percentage reduction in pre-existing antibody binding is calculated relative to the binding levels at 125 seconds of a reference ISVD.

Tetravalent ISVD format A022600424, optimized for reduced pre-existing antibody binding by introduction of mutations L11V and V89A for the anti-TCR building block, mutations L11V and V89L in each GPC3 and the serum albumin binding building block and a C-terminal alanine, shows substantially less binding to pre-existing antibodies compared to a control non-optimized tetravalent ISVD format F027301099 (FIG. 11A).

6.14 Example 14: Assessment of T-Cell Activation Induction by A022600424 in the Presence of Soluble GPC3

T-cell activation induction by A022600424 in the presence of soluble GPC3 was assessed as described in Example 6. A022600424 showed the same behaviour as its wild-type variant A022600168 (FIG. 7).

6.15 Example 15: In Vivo Proof-of-Concept for A022600424 in Huh-7 Tumor Bearing NOG Mice Engrafted with In Vitro Expanded T Cells In an in vivo efficacy study in tumor bearing NOG mouse, Hepatocellular Carcinoma Huh-7 tumor cells were injected subcutaneously, and tumors were allowed to grow until a mean tumor volume of ~150 $mm^3$ was reached. At this point, in vitro expanded T cells were injected intraperitoneally into the mice. Tumor cell killing by ISVD-mediated recruitment of T cells was evaluated by measuring the tumor volume and analyzing the tumor growth kinetics. The in vivo efficacy of A022600424 on tumor cell killing was evaluated and compared with the control T-cell engager T017000698 (SEQ ID NO: 74, Table A-6) lacking the GPC3 specificity.

In detail, $2\times10^6$ Huh-7 tumor cells resuspended in 100 μL of HBSS were subcutaneously injected in NOG mice. The tumors grew until the mean tumor volume of approximately 150 $mm^3$ was reached. At this point, $10^7$ in vitro expanded T cells resuspended in 200 μL of PBS were injected into each mouse intraperitoneally (DO). This injection of T cells took place 24 hours after mice were randomized into different groups. The treatment with A022600424 injected intravenously started on DO, 3 h after T cell injection and continued D3, D6, D9 and D12 (q3d; FIG. 12). Four dose levels of the TCR/GPC3 binding polypeptides were tested (0.1 mg/kg, 0.2 mg/kg, 0.7 mg/kg and 2 mg/kg). T017000698 was injected in a control group at 2 mg/kg on DO, D3, D6, D9 and D12 (q3d). Survival blood sampling in heparin containing tubes was done on D6 and D12 to measure antibody exposure. Mice were sacrificed on D15, and blood and tumor tissue were collected. Blood was used for the antibody exposure measurements and tumor tissue was used for analysis of target expression (GPC3) and T cell infiltration analysis.

Results for tumor growth kinetics are shown in FIG. 13. Mice treated with T017000698 were used as control group for analyses on D24, when all control mice were alive as they did not reach end point criteria (2000 $mm^3$ tumor volume). A dose response pattern was seen in tumor growth profile for A022600424 versus the control T017000698 for inducing tumor stasis. The 0.7 mg/kg (**, p=0.0016) and 2 mg/kg (*, p=0.0415) dose levels for the A022600424 were significantly different from the control T017000698. The 0.1 mg/kg, 0.2 mg/kg doses had lower effects on controlling tumor growth and were not significantly different to the control group. Statistical analysis has been performed with one-way ANOVA, using the Dunnett's multiple comparisons test for analysis.

In conclusion, the results demonstrate that A022600424 can dose-dependently induce statistically significant tumor stasis in this model. This confirms the concept of polypeptide-induced T cell-mediated killing via a GPC3 ISVD T-cell engager by cross-linking T cells to GPC3 on Huh-7 tumor cells.

7 INDUSTRIAL APPLICABILITY

The polypeptides, nucleic acid molecules encoding the same, vectors comprising the nucleic acids and compositions described herein may be used for example in the treatment of subjects suffering from cancer.

SEQUENCE LISTING

```
Sequence total quantity: 185
SEQ ID NO: 1            moltype = AA  length = 498
FEATURE                 Location/Qualifiers
REGION                  1..498
                        note = Synthetic-A022600424
source                  1..498
                        mol_type = protein
                        organism = synthetic construct
SEQUENCE: 1
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCAASGFT FSSFAMTWVR RPPGKGLEWV ATITNKGVTS  180
YADSVKGRFT ISRDNAKNTL YLQMNSLRPE DTALYICANA RRTGPRAPTD IGSYRGQGTL  240
VTVSSGGGGS GGGSEVQLVE SGGGVVQPGG SLRLSCAASG SIFRSVFSSS TMEWYRQAPG  300
KKRELVARIA PGEGTYYGAL YADSVKGRFT ISRDNAKNTV YLQMNSLRPE DTALYYCASG  360
VAWGQGTLVT VSSGGGGSGG GSEVQLVESG GGVVQPGGSL RLSCAASGFT FRSFGMSWVR  420
QAPGKGPEWV SSISGSGSDT LYADSVKGRF TISRDNSKNT LYLQMNSLRP EDTALYYCTI  480
GGSLSRSSQG TLVTVSSA                                                498

SEQ ID NO: 2            moltype = AA  length = 117
FEATURE                 Location/Qualifiers
REGION                  1..117
                        note = Synthetic-TCE01
source                  1..117
                        mol_type = protein
                        organism = synthetic construct
SEQUENCE: 2
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSS     117

SEQ ID NO: 3            moltype = AA  length = 123
FEATURE                 Location/Qualifiers
REGION                  1..123
                        note = Synthetic-A022600351
source                  1..123
                        mol_type = protein
                        organism = synthetic construct
SEQUENCE: 3
EVQLVESGGG VVQPGGSLRL SCAASGFTFS SFAMTWVRRP PGKGLEWVAT ITNKGVTSYA  60
DSVKGRFTIS RDNAKNTLYL QMNSLRPEDT ALYICANARR TGPRAPTDIG SYRGQGTLVT  120
VSS                                                                123
```

```
SEQ ID NO: 4            moltype = AA  length = 119
FEATURE                 Location/Qualifiers
REGION                  1..119
                        note = Synthetic-A022600314
source                  1..119
                        mol_type = protein
                        organism = synthetic construct
SEQUENCE: 4
EVQLVESGGG VVQPGGSLRL SCAASGSIFR SVFSSSTMEW YRQAPGKKRE LVARIAPGEG  60
TYYGALYADS VKGRFTISRD NAKNTVYLQM NSLRPEDTAL YYCASGVAWG QGTLVTVSS   119

SEQ ID NO: 5            moltype = AA  length = 115
FEATURE                 Location/Qualifiers
REGION                  1..115
                        note = Synthetic-ALB23002
source                  1..115
                        mol_type = protein
                        organism = synthetic construct
SEQUENCE: 5
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TALYYCTIGG SLSRSSQGTL VTVSS       115

SEQ ID NO: 6            moltype = AA  length = 10
FEATURE                 Location/Qualifiers
REGION                  1..10
                        note = Synthetic-CDR1
source                  1..10
                        mol_type = protein
                        organism = synthetic construct
SEQUENCE: 6
GYVHKINFYG                                                         10

SEQ ID NO: 7            moltype = AA  length = 10
FEATURE                 Location/Qualifiers
REGION                  1..10
                        note = Synthetic-CDR1
source                  1..10
                        mol_type = protein
                        organism = synthetic construct
SEQUENCE: 7
GFTFSSFAMT                                                         10

SEQ ID NO: 8            moltype = AA  length = 14
FEATURE                 Location/Qualifiers
REGION                  1..14
                        note = Synthetic-CDR1
source                  1..14
                        mol_type = protein
                        organism = synthetic construct
SEQUENCE: 8
GSIFRSVFSS STME                                                    14

SEQ ID NO: 9            moltype = AA  length = 10
FEATURE                 Location/Qualifiers
REGION                  1..10
                        note = Synthetic-CDR1
source                  1..10
                        mol_type = protein
                        organism = synthetic construct
SEQUENCE: 9
GFTFRSFGMS                                                         10

SEQ ID NO: 10           moltype = AA  length = 9
FEATURE                 Location/Qualifiers
REGION                  1..9
                        note = Synthetic-CDR2
source                  1..9
                        mol_type = protein
                        organism = synthetic construct
SEQUENCE: 10
HISIGDQTD                                                          9

SEQ ID NO: 11           moltype = AA  length = 9
FEATURE                 Location/Qualifiers
REGION                  1..9
                        note = Synthetic-CDR2
source                  1..9
                        mol_type = protein
                        organism = synthetic construct
```

```
SEQUENCE: 11
TITNKGVTS                                                        9

SEQ ID NO: 12          moltype = AA  length = 13
FEATURE                Location/Qualifiers
REGION                 1..13
                       note = Synthetic-CDR2
source                 1..13
                       mol_type = protein
                       organism = synthetic construct
SEQUENCE: 12
RIAPGEGTYY GAL                                                   13

SEQ ID NO: 13          moltype = AA  length = 10
FEATURE                Location/Qualifiers
REGION                 1..10
                       note = Synthetic-CDR2
source                 1..10
                       mol_type = protein
                       organism = synthetic construct
SEQUENCE: 13
SISGSGSDTL                                                       10

SEQ ID NO: 14          moltype = AA  length = 9
FEATURE                Location/Qualifiers
REGION                 1..9
                       note = Synthetic-CDR3
source                 1..9
                       mol_type = protein
                       organism = synthetic construct
SEQUENCE: 14
LSRIWPYDY                                                        9

SEQ ID NO: 15          moltype = AA  length = 15
FEATURE                Location/Qualifiers
REGION                 1..15
                       note = Synthetic-CDR3
source                 1..15
                       mol_type = protein
                       organism = synthetic construct
SEQUENCE: 15
ARRTGPRAPT DIGSY                                                 15

SEQ ID NO: 16          moltype =   length =
SEQUENCE: 16
000

SEQ ID NO: 17          moltype = AA  length = 6
FEATURE                Location/Qualifiers
REGION                 1..6
                       note = Synthetic-CDR3
source                 1..6
                       mol_type = protein
                       organism = synthetic construct
SEQUENCE: 17
GGSLSR                                                           6

SEQ ID NO: 18          moltype = AA  length = 25
FEATURE                Location/Qualifiers
REGION                 1..25
                       note = Synthetic-FR1
source                 1..25
                       mol_type = protein
                       organism = synthetic construct
SEQUENCE: 18
DVQLVESGGG VVQPGGSLRL SCVAS                                      25

SEQ ID NO: 19          moltype = AA  length = 25
FEATURE                Location/Qualifiers
REGION                 1..25
                       note = Synthetic-FR1
source                 1..25
                       mol_type = protein
                       organism = synthetic construct
SEQUENCE: 19
EVQLVESGGG VVQPGGSLRL SCAAS                                      25

SEQ ID NO: 20          moltype = AA  length = 14
FEATURE                Location/Qualifiers
```

```
REGION                  1..14
                        note = Synthetic-FR2
source                  1..14
                        mol_type = protein
                        organism = synthetic construct
SEQUENCE: 20
WYRQAPGKER EKVA                                                     14

SEQ ID NO: 21           moltype = AA  length = 14
FEATURE                 Location/Qualifiers
REGION                  1..14
                        note = Synthetic-FR2
source                  1..14
                        mol_type = protein
                        organism = synthetic construct
SEQUENCE: 21
WVRRPPGKGL EWVA                                                     14

SEQ ID NO: 22           moltype = AA  length = 14
FEATURE                 Location/Qualifiers
REGION                  1..14
                        note = Synthetic-FR2
source                  1..14
                        mol_type = protein
                        organism = synthetic construct
SEQUENCE: 22
WYRQAPGKKR ELVA                                                     14

SEQ ID NO: 23           moltype = AA  length = 14
FEATURE                 Location/Qualifiers
REGION                  1..14
                        note = Synthetic-FR2
source                  1..14
                        mol_type = protein
                        organism = synthetic construct
SEQUENCE: 23
WVRQAPGKGP EWVS                                                     14

SEQ ID NO: 24           moltype = AA  length = 39
FEATURE                 Location/Qualifiers
REGION                  1..39
                        note = Synthetic-FR3
source                  1..39
                        mol_type = protein
                        organism = synthetic construct
SEQUENCE: 24
YADSAKGRFT ISRDESKNTV YLQMNSLRPE DTAAYYCRA                          39

SEQ ID NO: 25           moltype = AA  length = 39
FEATURE                 Location/Qualifiers
REGION                  1..39
                        note = Synthetic-FR3
source                  1..39
                        mol_type = protein
                        organism = synthetic construct
SEQUENCE: 25
YADSVKGRFT ISRDNAKNTL YLQMNSLRPE DTALYICAN                          39

SEQ ID NO: 26           moltype = AA  length = 39
FEATURE                 Location/Qualifiers
REGION                  1..39
                        note = Synthetic-FR3
source                  1..39
                        mol_type = protein
                        organism = synthetic construct
SEQUENCE: 26
YADSVKGRFT ISRDNAKNTV YLQMNSLRPE DTALYYCAS                          39

SEQ ID NO: 27           moltype = AA  length = 39
FEATURE                 Location/Qualifiers
REGION                  1..39
                        note = Synthetic-FR3
source                  1..39
                        mol_type = protein
                        organism = synthetic construct
SEQUENCE: 27
YADSVKGRFT ISRDNSKNTL YLQMNSLRPE DTALYYCTI                          39

SEQ ID NO: 28           moltype = AA  length = 11
```

```
FEATURE                Location/Qualifiers
REGION                 1..11
                       note = Synthetic-FR4
source                 1..11
                       mol_type = protein
                       organism = synthetic construct
SEQUENCE: 28
WGQGTLVTVS S                                                        11

SEQ ID NO: 29          moltype = AA  length = 11
FEATURE                Location/Qualifiers
REGION                 1..11
                       note = Synthetic-FR4
source                 1..11
                       mol_type = protein
                       organism = synthetic construct
SEQUENCE: 29
RGQGTLVTVS S                                                        11

SEQ ID NO: 30          moltype = AA  length = 11
FEATURE                Location/Qualifiers
REGION                 1..11
                       note = Synthetic-FR4
source                 1..11
                       mol_type = protein
                       organism = synthetic construct
SEQUENCE: 30
SSQGTLVTVS S                                                        11

SEQ ID NO: 31          moltype = AA  length = 5
FEATURE                Location/Qualifiers
REGION                 1..5
                       note = Synthetic-CDR1
source                 1..5
                       mol_type = protein
                       organism = synthetic construct
SEQUENCE: 31
INFYG                                                               5

SEQ ID NO: 32          moltype = AA  length = 5
FEATURE                Location/Qualifiers
REGION                 1..5
                       note = Synthetic-CDR1
source                 1..5
                       mol_type = protein
                       organism = synthetic construct
SEQUENCE: 32
SFAMT                                                               5

SEQ ID NO: 33          moltype = AA  length = 9
FEATURE                Location/Qualifiers
REGION                 1..9
                       note = Synthetic-CDR1
source                 1..9
                       mol_type = protein
                       organism = synthetic construct
SEQUENCE: 33
SVFSSSTME                                                           9

SEQ ID NO: 34          moltype = AA  length = 5
FEATURE                Location/Qualifiers
REGION                 1..5
                       note = Synthetic-CDR1
source                 1..5
                       mol_type = protein
                       organism = synthetic construct
SEQUENCE: 34
SFGMS                                                               5

SEQ ID NO: 35          moltype = AA  length = 16
FEATURE                Location/Qualifiers
REGION                 1..16
                       note = Synthetic-CDR2
source                 1..16
                       mol_type = protein
                       organism = synthetic construct
SEQUENCE: 35
HISIGDQTDY ADSAKG                                                   16
```

```
SEQ ID NO: 36           moltype = AA  length = 16
FEATURE                 Location/Qualifiers
REGION                  1..16
                        note = Synthetic-CDR2
source                  1..16
                        mol_type = protein
                        organism = synthetic construct
SEQUENCE: 36
TITNKGVTSY ADSVKG                                                  16

SEQ ID NO: 37           moltype = AA  length = 20
FEATURE                 Location/Qualifiers
REGION                  1..20
                        note = Synthetic-CDR2
source                  1..20
                        mol_type = protein
                        organism = synthetic construct
SEQUENCE: 37
RIAPGEGTYY GALYADSVKG                                              20

SEQ ID NO: 38           moltype = AA  length = 17
FEATURE                 Location/Qualifiers
REGION                  1..17
                        note = Synthetic-CDR2
source                  1..17
                        mol_type = protein
                        organism = synthetic construct
SEQUENCE: 38
SISGSGSDTL YADSVKG                                                 17

SEQ ID NO: 39           moltype = AA  length = 30
FEATURE                 Location/Qualifiers
REGION                  1..30
                        note = Synthetic-FR1
source                  1..30
                        mol_type = protein
                        organism = synthetic construct
SEQUENCE: 39
DVQLVESGGG VVQPGGSLRL SCVASGYVHK                                   30

SEQ ID NO: 40           moltype = AA  length = 30
FEATURE                 Location/Qualifiers
REGION                  1..30
                        note = Synthetic-FR1
source                  1..30
                        mol_type = protein
                        organism = synthetic construct
SEQUENCE: 40
EVQLVESGGG VVQPGGSLRL SCAASGFTFS                                   30

SEQ ID NO: 41           moltype = AA  length = 30
FEATURE                 Location/Qualifiers
REGION                  1..30
                        note = Synthetic-FR1
source                  1..30
                        mol_type = protein
                        organism = synthetic construct
SEQUENCE: 41
EVQLVESGGG VVQPGGSLRL SCAASGSIFR                                   30

SEQ ID NO: 42           moltype = AA  length = 30
FEATURE                 Location/Qualifiers
REGION                  1..30
                        note = Synthetic-FR1
source                  1..30
                        mol_type = protein
                        organism = synthetic construct
SEQUENCE: 42
EVQLVESGGG VVQPGGSLRL SCAASGFTFR                                   30

SEQ ID NO: 43           moltype = AA  length = 32
FEATURE                 Location/Qualifiers
REGION                  1..32
                        note = Synthetic-FR3
source                  1..32
                        mol_type = protein
                        organism = synthetic construct
SEQUENCE: 43
RFTISRDESK NTVYLQMNSL RPEDTAAYYC RA                                32
```

```
SEQ ID NO: 44           moltype = AA  length = 32
FEATURE                 Location/Qualifiers
REGION                  1..32
                        note = Synthetic-FR3
source                  1..32
                        mol_type = protein
                        organism = synthetic construct
SEQUENCE: 44
RFTISRDNAK NTLYLQMNSL RPEDTALYIC AN                               32

SEQ ID NO: 45           moltype = AA  length = 32
FEATURE                 Location/Qualifiers
REGION                  1..32
                        note = Synthetic-FR3
source                  1..32
                        mol_type = protein
                        organism = synthetic construct
SEQUENCE: 45
RFTISRDNAK NTVYLQMNSL RPEDTALYYC AS                               32

SEQ ID NO: 46           moltype = AA  length = 32
FEATURE                 Location/Qualifiers
REGION                  1..32
                        note = Synthetic-FR3
source                  1..32
                        mol_type = protein
                        organism = synthetic construct
SEQUENCE: 46
RFTISRDNSK NTLYLQMNSL RPEDTALYYC TI                               32

SEQ ID NO: 47           moltype = AA  length = 119
FEATURE                 Location/Qualifiers
REGION                  1..119
                        note = Synthetic-A0226015A08
source                  1..119
                        mol_type = protein
                        organism = synthetic construct
SEQUENCE: 47
EVQLVESGGG LVQAGGSLRL SCVASGSIFR SVFSSSTMEW YRQPPGKKRE LVARIAPGDG  60
TNYGALYADS VKGRFTISRD DAKKTVDLQM NSLKPEDTGV YFCASGVAWG QGTLVTVSS   119

SEQ ID NO: 48           moltype = AA  length = 123
FEATURE                 Location/Qualifiers
REGION                  1..123
                        note = Synthetic-A0226018C08
source                  1..123
                        mol_type = protein
                        organism = synthetic construct
SEQUENCE: 48
EVQLVESGGG LVQPGGSLRL SCVASGFTFS SFAMTWVRRP PGKGLEWVAT ITNGGVTSYR  60
DSVKGRFTIS RDNAKNTLYL EMTSLNPEDT AVYICANARR TGPRAPTDIG SYRGQGTLVT  120
VSS                                                               123

SEQ ID NO: 49           moltype = AA  length = 433
FEATURE                 Location/Qualifiers
REGION                  1..433
                        note = Synthetic-A022600027
source                  1..433
                        mol_type = protein
                        organism = synthetic construct
SEQUENCE: 49
DVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQPGGSL RLSCVASGFT  180
FSSFAMTWVR RPPGKGLEWV ATITNGGVTS YRDSVKGRFT ISRDNAKNTL YLEMTSLNPE  240
DTAVYICANA RRTGPRAPTD IGSYRGQGTL VTVSSGGGGS GGGGSGGGGS GGGGSGGGGS  300
GGGGSGGGGS EVQLVESGGG VVQPGGSLRL SCAASGLTFS SYAMGWFRQA PGKERERVVS  360
ISRGGGYTYY ADSVKGRFTI SRDNSENTVY LQMNSLRPED TALYYCAAAR YWATGSEYEF  420
DYWGQGTLVT VSS                                                    433

SEQ ID NO: 50           moltype = AA  length = 429
FEATURE                 Location/Qualifiers
REGION                  1..429
                        note = Synthetic-A022600031
source                  1..429
                        mol_type = protein
                        organism = synthetic construct
SEQUENCE: 50
```

```
DVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGSL RLSCVASGSI  180
FRSVFSSSTM EWYRQPPGKK RELVARIAPG DGTNYGALYA DSVKGRFTIS RDDAKKTVDL  240
QMNSLKPEDT GVYFCASGVA WGQGTLVTVS SGGGGSGGGG SGGGGSGGGG SGGGGSGGGG  300
SGGGGSEVQL VESGGGVVQP GGSLRLSCAA SGLTFSSYAM GWFRQAPGKE RERVVSISRG  360
GGYTYYADSV KGRFTISRDN SENTVYLQMN SLRPEDTALY YCAAARYWAT GSEYEFDYWG  420
QGTLVTVSS                                                          429

SEQ ID NO: 51           moltype = AA  length = 426
FEATURE                 Location/Qualifiers
REGION                  1..426
                        note = Synthetic-A022600096
source                  1..426
                        mol_type = protein
                        organism = synthetic construct
SEQUENCE: 51
DVQLVESGGG LVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSGGGGSGGG GSGGGGSGGG GSGGGGSGGG GSEVQLVESG GGLVQPGGSL RLSCVASGFT  180
FSSFAMTWVR RPPGKGLEWV ATITNGGVTS YRDSVKGRFT ISRDNAKNTL YLEMTSLNPE  240
DTAVYICANA RRTGPRAPTD IGSYRGQGTL VTVSSGGGGS GGGGSGGGGS GGGGSGGGGS  300
GGGGSGGGGS EVQLVESGGG VVQPGGSLRL SCAASGFTFR SFGMSWVRQA PGKGPEWVSS  360
ISGSGSDTLY ADSVKGRFTI SRDNSKNTLY LQMNSLRPED TALYYCTIGG SLSRSSQGTL  420
VTVSSA                                                             426

SEQ ID NO: 52           moltype = AA  length = 394
FEATURE                 Location/Qualifiers
REGION                  1..394
                        note = Synthetic-A022600102
source                  1..394
                        mol_type = protein
                        organism = synthetic construct
SEQUENCE: 52
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSAAA  120
EVQLVESGGG LVQPGGSLRL SCVASGFTFS SFAMTWVRRP PGKGLEWVAT ITNGGVTSYR  180
DSVKGRFTIS RDNAKNTLYL EMTSLNPEDT AVYICANARR TGPRAPTDIG SYRGQGTLVT  240
VSSGGGGSGG GGSGGGGSGG GGSGGGGSGG GGSGGGGSEV QLVESGGGVV QPGGSLRLSC  300
AASGFTFRSF GMSWVRQAPG KGPEWVSSIS GSGSDTLYAD SVKGRFTISR DNSKNTLYLQ  360
MNSLRPEDTA LYYCTIGGSL SRSSQGTLVT VSSA                              394

SEQ ID NO: 53           moltype = AA  length = 396
FEATURE                 Location/Qualifiers
REGION                  1..396
                        note = Synthetic-A022600103
source                  1..396
                        mol_type = protein
                        organism = synthetic construct
SEQUENCE: 53
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGGSGGGGS GGGGSGGGGS GGGGSGGGGS EVQLVESGGG VVQPGGSLRL  300
SCAASGFTFR SFGMSWVRQA PGKGPEWVSS ISGSGSDTLY ADSVKGRFTI SRDNSKNTLY  360
LQMNSLRPED TALYYCTIGG SLSRSSQGTL VTVSSA                            396

SEQ ID NO: 54           moltype = AA  length = 400
FEATURE                 Location/Qualifiers
REGION                  1..400
                        note = Synthetic-A022600104
source                  1..400
                        mol_type = protein
                        organism = synthetic construct
SEQUENCE: 54
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSGGGGSEVQL VESGGGLVQP GGSLRLSCVA SGFTFSSFAM TWVRRPPGKG LEWVATITNG  180
GVTSYRDSVK GRFTISRDNA KNTLYLEMTS LNPEDTAVYI CANARRTGPR APTDIGSYRG  240
QGTLVTVSSG GGGSGGGGSG GGGSGGGGSG GGGSGGGGSG GGGSEVQLVE SGGGVVQPGG  300
SLRLSCAASG FTFRSFGMSW VRQAPGKGPE WVSSISGSGS DTLYADSVKG RFTISRDNSK  360
NTLYLQMNSL RPEDTALYYC TIGGSLSRSS QGTLVTVSSA                        400

SEQ ID NO: 55           moltype = AA  length = 411
FEATURE                 Location/Qualifiers
REGION                  1..411
                        note = Synthetic-A022600105
source                  1..411
```

```
                        mol_type = protein
                        organism = synthetic construct
SEQUENCE: 55
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSGGGGSGGG GSGGGGSEVQ LVESGGGLVQ PGGSLRLSCV ASGFTFSSFA MTWVRRPPGK  180
GLEWVATITN GGVTSYRDSV KGRFTISRDN AKNTLYLEMT SLNPEDTAVY ICANARRTGP  240
RAPTDIGSYR GQGTLVTVSS GGGGSGGGGS GGGGSGGGGS GGGGSGGGGS GGGGSEVQLV  300
ESGGGVVQPG GSLRLSCAAS GFTFRSFGMS WVRQAPGKGP EWVSSISGSG SDTLYADSVK  360
GRFTISRDNS KNTLYLQMNS LRPEDTALYY CTIGGSLSRS SQGTLVTVSS A          411

SEQ ID NO: 56           moltype = AA  length = 550
FEATURE                 Location/Qualifiers
REGION                  1..550
                        note = Synthetic-A022600122
source                  1..550
                        mol_type = protein
                        organism = synthetic construct
SEQUENCE: 56
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGGSGGGGS GGGGSGGGGS GGGGSGGGGS EVQLVESGGG LVQPGGSLRL  300
SCVASGSIFR SVFSSSTMEW YRQPPGKKRE LVARIAPGDG TNYGALYADS VKGRFTISRD  360
DAKKTVDLQM NSLKPEDTGV YFCASGVAWG QGTLVTVSSG GGGSGGGGSG GGGSGGGGSG  420
GGGSGGGGSG GGGSEVQLVE SGGGVVQPGG SLRLSCAASG FTFRSFGMSW VRQAPGKGPE  480
WVSSISGSGS DTLYADSVKG RFTISRDNSK NTLYLQMNSL RPEDTALYYC TIGGSLSRSS  540
QGTLVTVSSA                                                        550

SEQ ID NO: 57           moltype = AA  length = 535
FEATURE                 Location/Qualifiers
REGION                  1..535
                        note = Synthetic-A022600131
source                  1..535
                        mol_type = protein
                        organism = synthetic construct
SEQUENCE: 57
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGGSGGGGS GGGGSEVQLV ESGGGLVQPG GSLRLSCVAS GSIFRSVFSS  300
STMEWYRQPP GKKRELVARI APGDGTNYGA LYADSVKGRF TISRDDAKKT VDLQMNSLKP  360
EDTGVYFCAS GVAWGQGTLV TVSSGGGGSG GGGSGGGGSG GGGSGGGGSG GGGSGGGGSE  420
VQLVESGGGV VQPGGSLRLS CAASGFTFRS FGMSWVRQAP GKGPEWVSSI SGSGSDTLYA  480
DSVKGRFTIS RDNSKNTLYL QMNSLRPEDT ALYYCTIGGS LSRSSQGTLV TVSSA       535

SEQ ID NO: 58           moltype = AA  length = 524
FEATURE                 Location/Qualifiers
REGION                  1..524
                        note = Synthetic-A022600132
source                  1..524
                        mol_type = protein
                        organism = synthetic construct
SEQUENCE: 58
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGSEVQLVE SGGGLVQPGG SLRLSCVASG SIFRSVFSSS TMEWYRQPPG  300
KKRELVARIA PGDGTNYGAL YADSVKGRFT ISRDDAKKTV DLQMNSLKPE DTGVYFCASG  360
VAWGQGTLVT VSSGGGGSGG GGSGGGGSGG GGSGGGGSGG GGSGGGGSEV QLVESGGGVV  420
QPGGSLRLSC AASGFTFRSF GMSWVRQAPG KGPEWVSSIS GSGSDTLYAD SVKGRFTISR  480
DNSKNTLYLQ MNSLRPEDTA LYYCTIGGSL SRSSQGTLVT VSSA                  524

SEQ ID NO: 59           moltype = AA  length = 550
FEATURE                 Location/Qualifiers
REGION                  1..550
                        note = Synthetic-A022600133
source                  1..550
                        mol_type = protein
                        organism = synthetic construct
SEQUENCE: 59
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGSI FRSVFSSSTM EWYRQPPGKK RELVARIAPG  180
DGTNYGALYA DSVKGRFTIS RDDAKKTVDL QMNSLKPEDT GVYFCASGVA WGQGTLVTVS  240
SGGGGSGGGG SGGGGSGGGG SGGGGSGGGG SGGGGSEVQL VESGGGLVQP GGSLRLSCVA  300
```

```
SGFTFSSFAM TWVRRPPGKG LEWVATITNG GVTSYRDSVK GRFTISRDNA KNTLYLEMTS  360
LNPEDTAVYI CANARRTGPR APTDIGSYRG QGTLVTVSSG GGGSGGGGSG GGGSGGGGSG  420
GGGSGGGGSG GGGSEVQLVE SGGGVVQPGG SLRLSCAASG FTFRSFGMSW VRQAPGKGPE  480
WVSSISGSGS DTLYADSVKG RFTISRDNSK NTLYLQMNSL RPEDTALYYC TIGGSLSRSS  540
QGTLVTVSSA                                                        550

SEQ ID NO: 60          moltype = AA  length = 535
FEATURE                Location/Qualifiers
REGION                 1..535
                       note = Synthetic-A022600134
source                 1..535
                       mol_type = protein
                       organism = synthetic construct
SEQUENCE: 60
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGSI FRSVFSSSTM EWYRQPPGKK RELVARIAPG  180
DGTNYGALYA DSVKGRFTIS RDDAKKTVDL QMNSLKPEDT GVYFCASGVA WGQGTLVTVS  240
SGGGGSGGGG SGGGGSGGGG SEVQLVESGG GLVQPGGSLR LSCVASGFTF SSFAMTWVRR  300
PPGKGLEWVA TITNGGVTSY RDSVKGRFTI SRDNAKNTLY LEMTSLNPED TAVYICANAR  360
RTGPRAPTDI GSYRGQGTLV TVSSGGGGSG GGGSGGGGSG GGGSGGGGSG GGGSGGGGSE  420
VQLVESGGGV VQPGGSLRLS CAASGFTFRS FGMSWVRQAP GKGPEWVSSI SGSGSDTLYA  480
DSVKGRFTIS RDNSKNTLYL QMNSLRPEDT ALYYCTIGGS LSRSSQGTLV TVSSA       535

SEQ ID NO: 61          moltype = AA  length = 524
FEATURE                Location/Qualifiers
REGION                 1..524
                       note = Synthetic-A022600135
source                 1..524
                       mol_type = protein
                       organism = synthetic construct
SEQUENCE: 61
DVQLVESGGG VVQPGGSLRL SCVASGYVHK INFYGWYRQA PGKEREKVAH ISIGDQTDYA  60
DSAKGRFTIS RDESKNTVYL QMNSLRPEDT ALYYCRALSR IWPYDYWGQG TLVTVSSGGG  120
GSEVQLVESG GGLVQPGGSL RLSCVASGSI FRSVFSSSTM EWYRQPPGKK RELVARIAPG  180
DGTNYGALYA DSVKGRFTIS RDDAKKTVDL QMNSLKPEDT GVYFCASGVA WGQGTLVTVS  240
SGGGGSGGGS EVQLVESGGG LVQPGGSLRL SCVASGFTFS SFAMTWVRRP PGKGLEWVAT  300
ITNGGVTSYR DSVKGRFTIS RDNAKNTLYL EMTSLNPEDT AVYICANARR TGPRAPTDIG  360
SYRGQGTLVT VSSGGGGSGG GGSGGGGSGG GGSGGGGSGG GGSGGGGSEV QLVESGGGVV  420
QPGGSLRLSC AASGFTFRSF GMSWVRQAPG KGPEWVSSIS GSGSDTLYAD SVKGRFTISR  480
DNSKNTLYLQ MNSLRPEDTA LYYCTIGGSL SRSSQGTLVT VSSA                  524

SEQ ID NO: 62          moltype = AA  length = 396
FEATURE                Location/Qualifiers
REGION                 1..396
                       note = Synthetic-A022600167
source                 1..396
                       mol_type = protein
                       organism = synthetic construct
SEQUENCE: 62
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGGSGGGGS GGGGSGGGGS GGGGSGGGGS EVQLVESGGG VVQPGGSLRL  300
SCAASGFTFR SFGMSWVRQA PGKGPEWVSS ISGSGSDTLY ADSVKGRFTI SRDNSKNTLY  360
LQMNSLRPED TALYYCTIGG SLSRSSQGTL VTVSSA                            396

SEQ ID NO: 63          moltype = AA  length = 550
FEATURE                Location/Qualifiers
REGION                 1..550
                       note = Synthetic-A022600168
source                 1..550
                       mol_type = protein
                       organism = synthetic construct
SEQUENCE: 63
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGGSGGGGS GGGGSGGGGS GGGGSGGGGS EVQLVESGGG LVQPGGSLRL  300
SCVASGSIFR SVFSSSTMEW YRQPPGKKRE LVARIAPGDG TNYGALYADS VKGRFTISRD  360
DAKKTVDLQM NSLKPEDTGV YFCASGVAWG QGTLVTVSSG GGGSGGGGSG GGGSGGGGSG  420
GGGSGGGGSG GGGSEVQLVE SGGGVVQPGG SLRLSCAASG FTFRSFGMSW VRQAPGKGPE  480
WVSSISGSGS DTLYADSVKG RFTISRDNSK NTLYLQMNSL RPEDTALYYC TIGGSLSRSS  540
QGTLVTVSSA                                                        550

SEQ ID NO: 64          moltype = AA  length = 520
FEATURE                Location/Qualifiers
```

```
REGION                  1..520
                        note = Synthetic-A022600169
source                  1..520
                        mol_type = protein
                        organism = synthetic construct
SEQUENCE: 64
DVQLVESGGG LVQPGGSLRL SCVASGFTFS SFAMTWVRRP PGKGLEWVAT ITNGGVTSYR  60
DSVKGRFTIS RDNAKNTLYL EMTSLNPEDT AVYICANARR TGPRAPTDIG SYRGQGTLVT  120
VSSGGGGSEV QLVESGGGVV QPGGSLRLSC VASGYVHKIN FYGWYRQAPG KEREKVAHIS  180
IGDQTDYADS AKGRFTISRD ESKNTVYLQM NSLRPEDTAA YYCRALSRIW PYDYWGQGTL  240
VTVSSGGGGS EVQLVESGGG LVQPGGSLRL SCVASGSIFR SVFSSSTMEW YRQPPGKKRE  300
LVARIAPGDG TNYGALYADS VKGRFTISRD DAKKTVDLQM NSLKPEDTGV YFCASGVAWG  360
QGTLVTVSSG GGGSGGGGSG GGGSGGGGSG GGGSGGGGSG GGGSEVQLVE SGGGVVQPGG  420
SLRLSCAASG FTFRSFGMSW VRQAPGKGPE WVSSISGSGS DTLYADSVKG RFTISRDNSK  480
NTLYLQMNSL RPEDTALYYC TIGGSLSRSS QGTLVTVSSA                        520

SEQ ID NO: 65           moltype = AA  length = 524
FEATURE                 Location/Qualifiers
REGION                  1..524
                        note = Synthetic-A022600170
source                  1..524
                        mol_type = protein
                        organism = synthetic construct
SEQUENCE: 65
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGGSGGGGS GGGGSGGGGS GGGGSGGGGS EVQLVESGGG LVQPGGSLRL  300
SCVASGSIFR SVFSSSTMEW YRQPPGKKRE LVARIAPGDG TNYGALYADS VKGRFTISRD  360
DAKKTVDLQM NSLKPEDTGV YFCASGVAWG QGTLVTVSSG GGGSGGGSEV QLVESGGGVV  420
QPGGSLRLSC AASGFTFRSF GMSWVRQAPG KGPEWVSSIS GSGSDTLYAD SVKGRFTISR  480
DNSKNTLYLQ MNSLRPEDTA LYYCTIGGSL SRSSQGTLVT VSSA                   524

SEQ ID NO: 66           moltype = AA  length = 498
FEATURE                 Location/Qualifiers
REGION                  1..498
                        note = Synthetic-A022600172
source                  1..498
                        mol_type = protein
                        organism = synthetic construct
SEQUENCE: 66
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGSEVQLVE SGGGVVQPGG SLRLSCAASG FTFRSFGMSW VRQAPGKGPE  300
WVSSISGSGS DTLYADSVKG RFTISRDNSK NTLYLQMNSL RPEDTALYYC TIGGSLSRSS  360
QGTLVTVSSG GGGSGGGSEV QLVESGGGLV QPGGSLRLSC VASGSIFRSV FSSSTMEWYR  420
QPPGKKRELV ARIAPGDGTN YGALYADSVK GRFTISRDDA KKTVDLQMNS LKPEDTGVYF  480
CASGVAWGQG TLVTVSSA                                                498

SEQ ID NO: 67           moltype = AA  length = 498
FEATURE                 Location/Qualifiers
REGION                  1..498
                        note = Synthetic-A022600174
source                  1..498
                        mol_type = protein
                        organism = synthetic construct
SEQUENCE: 67
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGSEVQLVE SGGGLVQPGG SLRLSCVASG SIFRSVFSSS TMEWYRQPPG  300
KKRELVARIA PGDGTNYGAL YADSVKGRFT ISRDDAKKTV DLQMNSLKPE DTGVYFCASG  360
VAWGQGTLVT VSSGGGGSGG GSEVQLVESG GGVVQPGGSL RLSCAASGFT FRSFGMSWVR  420
QAPGKGPEWV SSISGSGSDT LYADSVKGRF TISRDNSKNT LYLQMNSLRP EDTALYYCTI  480
GGSLSRSSQG TLVTVSSA                                                498

SEQ ID NO: 68           moltype = AA  length = 524
FEATURE                 Location/Qualifiers
REGION                  1..524
                        note = Synthetic-A022600175
source                  1..524
                        mol_type = protein
                        organism = synthetic construct
SEQUENCE: 68
DVQLVESGGG VVQPGGSLRL SCVASGYVHK INFYGWYRQA PGKEREKVAH ISIGDQTDYA  60
```

```
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGSEVQLVE SGGGLVQPGG SLRLSCVASG SIFRSVFSSS TMEWYRQPPG  300
KKRELVARIA PGDGTNYGAL YADSVKGRFT ISRDDAKKTV DLQMNSLKPE DTGVYFCASG  360
VAWGQGTLVT VSSGGGGSGG GGSGGGGSGG GGSGGGGSGG GGSGGGGSEV QLVESGGGVV  420
QPGGSLRLSC AASGFTFRSF GMSWVRQAPG KGPEWVSSIS GSGSDTLYAD SVKGRFTISR  480
DNSKNTLYLQ MNSLRPEDTA LYYCTIGGSL SRSSQGTLVT VSSA                   524

SEQ ID NO: 69          moltype = AA  length = 396
FEATURE                Location/Qualifiers
REGION                 1..396
                       note = Synthetic-A022600178
source                 1..396
                       mol_type = protein
                       organism = synthetic construct
SEQUENCE: 69
DVQLVESGGG LVQPGGSLRL SCVASGFTFS SFAMTWVRRP PGKGLEWVAT ITNGGVTSYR  60
DSVKGRFTIS RDNAKNTLYL EMTSLNPEDT AVYICANARR TGPRAPTDIG SYRGQGTLVT  120
VSSGGGGSEV QLVESGGGVV QPGGSLRLSC VASGYVHKIN FYGWYRQAPG KEREKVAHIS  180
IGDQTDYADS AKGRFTISRD ESKNTVYLQM NSLRPEDTAA YYCRALSRIW PYDYWGQGTL  240
VTVSSGGGGS GGGGSGGGGS GGGGSGGGGS GGGGSGGGGS EVQLVESGGG VVQPGGSLRL  300
SCAASGFTFR SFGMSWVRQA PGKGPEWVSS ISGSGSDTLY ADSVKGRFTI SRDNSKNTLY  360
LQMNSLRPED TALYYCTIGG SLSRSSQGTL VTVSSA                             396

SEQ ID NO: 70          moltype = AA  length = 370
FEATURE                Location/Qualifiers
REGION                 1..370
                       note = Synthetic-A022600179
source                 1..370
                       mol_type = protein
                       organism = synthetic construct
SEQUENCE: 70
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGLVQPGGSL RLSCVASGFT FSSFAMTWVR RPPGKGLEWV ATITNGGVTS  180
YRDSVKGRFT ISRDNAKNTL YLEMTSLNPE DTAVYICANA RRTGPRAPTD IGSYRGQGTL  240
VTVSSGGGGS GGGSEVQLVE SGGGVVQPGG SLRLSCAASG FTFRSFGMSW VRQAPGKGPE  300
WVSSISGSGS DTLYADSVKG RFTISRDNSK NTLYLQMNSL RPEDTALYYC TIGGSLSRSS  360
QGTLVTVSSA                                                         370

SEQ ID NO: 71          moltype = AA  length = 383
FEATURE                Location/Qualifiers
REGION                 1..383
                       note = Synthetic-A022600370
source                 1..383
                       mol_type = protein
                       organism = synthetic construct
SEQUENCE: 71
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCVASGFT FSSFAMTWVR RPPGKGLEWV ATITNGGVTS  180
YRDSVKGRFT ISRDNAKNTL YLEMTSLRPE DTALYICANA RRTGPRAPTD IGSYRGQGTL  240
VTVSSGGGGS GGGGSGGGGS GGGGSEVQLV ESGGGVVQPG GSLRLSCAAS GFTFRSFGMS  300
WVRQAPGKGP EWVSSISGSG SDTLYADSVK GRFTISRDNS KNTLYLQMNS LRPEDTALYY  360
CTIGGSLSRS SQGTLVTVSS GGC                                          383

SEQ ID NO: 72          moltype = AA  length = 500
FEATURE                Location/Qualifiers
REGION                 1..500
                       note = Synthetic-A022600372
source                 1..500
                       mol_type = protein
                       organism = synthetic construct
SEQUENCE: 72
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCVASGFT FSSFAMTWVR RPPGKGLEWV ATITNGGVTS  180
YRDSVKGRFT ISRDNAKNTL YLEMTSLRPE DTALYICANA RRTGPRAPTD IGSYRGQGTL  240
VTVSSGGGGS GGGSEVQLVE SGGGVVQPGG SLRLSCVASG SIFRSVFSSS TMEWYRQPPG  300
KKRELVARIA PGDGTNYGAL YADSVKGRFT ISRDDAKKTV DLQMNSLRPE DTGLYFCASG  360
VAWGQGTLVT VSSGGGGSGG GSEVQLVESG GGVVQPGGSL RLSCAASGFT FRSFGMSWVR  420
QAPGKGPEWV SSISGSGSDT LYADSVKGRF TISRDNSKNT LYLQMNSLRP EDTALYYCTI  480
GGSLSRSSQG TLVTVSSGGC                                              500

SEQ ID NO: 73          moltype = AA  length = 255
FEATURE                Location/Qualifiers
REGION                 1..255
                       note = Synthetic-A022600373
```

```
source                  1..255
                        mol_type = protein
                        organism = synthetic construct
SEQUENCE: 73
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSGGGGSGGG GSGGGGSEVQ LVESGGGVVQ PGGSLRLSCA ASGFTFRSFG MSWVRQAPGK  180
GPEWVSSISG SGSDTLYADS VKGRFTISRD NSKNTLYLQM NSLRPEDTAL YYCTIGGSLS  240
RSSQGTLVTV SSGGC                                                   255

SEQ ID NO: 74           moltype = AA  length = 242
FEATURE                 Location/Qualifiers
REGION                  1..242
                        note = Synthetic-T017000698
source                  1..242
                        mol_type = protein
                        organism = synthetic construct
SEQUENCE: 74
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSGGGSEVQL VESGGGVVQP GGSLRLSCAA SGFTFRSFGM SWVRQAPGKG PEWVSSISGS  180
GSDTLYADSV KGRFTISRDN SKNTLYLQMN SLRPEDTALY YCTIGGSLSR SSQGTLVTVS  240
SA                                                                 242

SEQ ID NO: 75           moltype = AA  length = 119
FEATURE                 Location/Qualifiers
REGION                  1..119
                        note = Synthetic-A022600314
source                  1..119
                        mol_type = protein
                        organism = synthetic construct
SEQUENCE: 75
EVQLVESGGG VVQPGGSLRL SCAASGSIFR SVFSSSTMEW YRQAPGKKRE LVARIAPGEG  60
TYYGALYADS VKGRFTISRD NAKNTVYLQM NSLRPEDTAL YYCASGVAWG QGTLVTVSS   119

SEQ ID NO: 76           moltype = AA  length = 123
FEATURE                 Location/Qualifiers
REGION                  1..123
                        note = Synthetic-A022600345
source                  1..123
                        mol_type = protein
                        organism = synthetic construct
SEQUENCE: 76
EVQLVESGGG VVQPGGSLRL SCAASGFTFS SFAMTWVRRP PGKGLEWVAT ITNAGVTSYA  60
DSVKGRFTIS RDNAKNTLYL QMNSLRPEDT ALYICANARR TGPRAPTDIG SYRGQGTLVT  120
VSS                                                                123

SEQ ID NO: 77           moltype = AA  length = 123
FEATURE                 Location/Qualifiers
REGION                  1..123
                        note = Synthetic-A022600351
source                  1..123
                        mol_type = protein
                        organism = synthetic construct
SEQUENCE: 77
EVQLVESGGG VVQPGGSLRL SCAASGFTFS SFAMTWVRRP PGKGLEWVAT ITNKGVTSYA  60
DSVKGRFTIS RDNAKNTLYL QMNSLRPEDT ALYICANARR TGPRAPTDIG SYRGQGTLVT  120
VSS                                                                123

SEQ ID NO: 78           moltype = AA  length = 381
FEATURE                 Location/Qualifiers
REGION                  1..381
                        note = Synthetic-A022600412
source                  1..381
                        mol_type = protein
                        organism = synthetic construct
SEQUENCE: 78
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCAASGFT FSSFAMTWVR RPPGKGLEWV ATITNAGVTS  180
YADSVKGRFT ISRDNAKNTL YLQMNSLRPE DTALYICANA RRTGPRAPTD IGSYRGQGTL  240
VTVSSGGGGS GGGGSGGGGS GGGGSEVQLV ESGGGVVQPG GSLRLSCAAS GFTFRSFGMS  300
WVRQAPGKGP EWVSSISGSG SDTLYADSVK GRFTISRDNS KNTLYLQMNS LRPEDTALYY  360
CTIGGSLSRS SQGTLVTVSS A                                            381

SEQ ID NO: 79           moltype = AA  length = 509
FEATURE                 Location/Qualifiers
REGION                  1..509
                        note = Synthetic-A022600425
```

```
source                  1..509
                        mol_type = protein
                        organism = synthetic construct
SEQUENCE: 79
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCAASGSI FRSVFSSSTM EWYRQAPGKK RELVARIAPG  180
EGTYYGALYA DSVKGRFTIS RDNAKNTVYL QMNSLRPEDT ALYYCASGVA WGQGTLVTVS  240
SGGGGSGGGG SGGGGSGGGG SEVQLVESGG GVVQPGGSLR LSCAASGFTF SSFAMTWVRR  300
PPGKGLEWVA TITNAGVTSY ADSVKGRFTI SRDNAKNTLY LQMNSLRPED TALYICANAR  360
RTGPRAPTDI GSYRGQGTLV TVSSGGGGSG GGSEVQLVES GGGVVQPGGS LRLSCAASGF  420
TFRSFGMSWV RQAPGKGPEW VSSISGSGSD TLYADSVKGR FTISRDNSKN TLYLQMNSLR  480
PEDTALYYCT IGGSLSRSSQ GTLVTVSSA                                    509

SEQ ID NO: 80           moltype = AA  length = 509
FEATURE                 Location/Qualifiers
REGION                  1..509
                        note = Synthetic-A022600426
source                  1..509
                        mol_type = protein
                        organism = synthetic construct
SEQUENCE: 80
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCAASGSI FRSVFSSSTM EWYRQAPGKK RELVARIAPG  180
EGTYYGALYA DSVKGRFTIS RDNAKNTVYL QMNSLRPEDT ALYYCASGVA WGQGTLVTVS  240
SGGGGSGGGG SGGGGSGGGG SEVQLVESGG GVVQPGGSLR LSCAASGFTF SSFAMTWVRR  300
PPGKGLEWVA TITNKGVTSY ADSVKGRFTI SRDNAKNTLY LQMNSLRPED TALYICANAR  360
RTGPRAPTDI GSYRGQGTLV TVSSGGGGSG GGSEVQLVES GGGVVQPGGS LRLSCAASGF  420
TFRSFGMSWV RQAPGKGPEW VSSISGSGSD TLYADSVKGR FTISRDNSKN TLYLQMNSLR  480
PEDTALYYCT IGGSLSRSSQ GTLVTVSSA                                    509

SEQ ID NO: 81           moltype = AA  length = 498
FEATURE                 Location/Qualifiers
REGION                  1..498
                        note = Synthetic-A022600427
source                  1..498
                        mol_type = protein
                        organism = synthetic construct
SEQUENCE: 81
DVQLVESGGG VVQPGGSLRL SCVASGYVHK INFYGWYRQA PGKEREKVAH ISIGDQTDYA  60
DSAKGRFTIS RDESKNTVYL QMNSLRPEDT AAYYCRALSR IWPYDYWGQG TLVTVSSGGG  120
GSEVQLVESG GGVVQPGGSL RLSCAASGFT FSSFAMTWVR RPPGKGLEWV ATITNAGVTS  180
YADSVKGRFT ISRDNAKNTL YLQMNSLRPE DTALYICANA RRTGPRAPTD IGSYRGQGTL  240
VTVSSGGGGS GGGSEVQLVE SGGGVVQPGG SLRLSCAASG SIFRSVFSSS TMEWYRQAPG  300
KKRELVARIA PGEGTYYGAL YADSVKGRFT ISRDNAKNTV YLQMNSLRPE DTALYYCASG  360
VAWGQGTLVT VSSGGGGSGG GSEVQLVESG GGVVQPGGSL RLSCAASGFT FRSFGMSWVR  420
QAPGKGPEWV SSISGSGSDT LYADSVKGRF TISRDNSKNT LYLQMNSLRP EDTALYYCTI  480
GGSLSRSSQG TLVTVSSA                                                498

SEQ ID NO: 82           moltype = AA  length = 115
FEATURE                 Location/Qualifiers
REGION                  1..115
                        note = Synthetic-Alb8
source                  1..115
                        mol_type = protein
                        organism = synthetic construct
SEQUENCE: 82
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVSS       115

SEQ ID NO: 83           moltype = AA  length = 116
FEATURE                 Location/Qualifiers
REGION                  1..116
                        note = Synthetic-Alb8-A
source                  1..116
                        mol_type = protein
                        organism = synthetic construct
SEQUENCE: 83
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVSSA      116

SEQ ID NO: 84           moltype = AA  length = 115
FEATURE                 Location/Qualifiers
REGION                  1..115
                        note = Synthetic-Alb23
source                  1..115
                        mol_type = protein
                        organism = synthetic construct
```

```
SEQUENCE: 84
EVQLLESGGG LVQPGGSLRL SCAASGFTFR SFGMSWVRQA PGKGPEWVSS ISGSGSDTLY  60
ADSVKGRFTI SRDNSKNTLY LQMNSLRPED TAVYYCTIGG SLSRSSQGTL VTVSS       115

SEQ ID NO: 85          moltype = AA  length = 116
FEATURE                Location/Qualifiers
REGION                 1..116
                       note = Synthetic-Alb23-A
source                 1..116
                       mol_type = protein
                       organism = synthetic construct
SEQUENCE: 85
EVQLLESGGG LVQPGGSLRL SCAASGFTFR SFGMSWVRQA PGKGPEWVSS ISGSGSDTLY  60
ADSVKGRFTI SRDNSKNTLY LQMNSLRPED TAVYYCTIGG SLSRSSQGTL VTVSSA      116

SEQ ID NO: 86          moltype = AA  length = 115
FEATURE                Location/Qualifiers
REGION                 1..115
                       note = Synthetic-Alb83
source                 1..115
                       mol_type = protein
                       organism = synthetic construct
SEQUENCE: 86
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TATYYCTIGG SLSRSSQGTL VTVSS       115

SEQ ID NO: 87          moltype = AA  length = 116
FEATURE                Location/Qualifiers
REGION                 1..116
                       note = Synthetic-Alb83-A
source                 1..116
                       mol_type = protein
                       organism = synthetic construct
SEQUENCE: 87
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TATYYCTIGG SLSRSSQGTL VTVSSA      116

SEQ ID NO: 88          moltype = AA  length = 115
FEATURE                Location/Qualifiers
REGION                 1..115
                       note = Synthetic-Alb132
source                 1..115
                       mol_type = protein
                       organism = synthetic construct
SEQUENCE: 88
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TATYYCTIGG SLSRSSQGTL VTVSS       115

SEQ ID NO: 89          moltype = AA  length = 116
FEATURE                Location/Qualifiers
REGION                 1..116
                       note = Synthetic-Alb132-A
source                 1..116
                       mol_type = protein
                       organism = synthetic construct
SEQUENCE: 89
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TATYYCTIGG SLSRSSQGTL VTVSSA      116

SEQ ID NO: 90          moltype = AA  length = 115
FEATURE                Location/Qualifiers
REGION                 1..115
                       note = Synthetic-Alb73
source                 1..115
                       mol_type = protein
                       organism = synthetic construct
SEQUENCE: 90
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VKVSS       115

SEQ ID NO: 91          moltype = AA  length = 116
FEATURE                Location/Qualifiers
REGION                 1..116
                       note = Synthetic-Alb73-A
source                 1..116
                       mol_type = protein
                       organism = synthetic construct
SEQUENCE: 91
EVQLVESGGG LVQPGNSLRL SCAASGFTFS SFGMSWVRQA PGKGLEWVSS ISGSGSDTLY  60
```

```
ADSVKGRFTI SRDNAKTTLY LQMNSLRPED TAVYYCTIGG SLSRSSQGTL VKVSSA      116

SEQ ID NO: 92          moltype = AA  length = 115
FEATURE                Location/Qualifiers
REGION                 1..115
                       note = Synthetic-Alb82
source                 1..115
                       mol_type = protein
                       organism = synthetic construct
SEQUENCE: 92
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSS       115

SEQ ID NO: 93          moltype = AA  length = 116
FEATURE                Location/Qualifiers
REGION                 1..116
                       note = Synthetic-Alb82-A
source                 1..116
                       mol_type = protein
                       organism = synthetic construct
SEQUENCE: 93
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSA      116

SEQ ID NO: 94          moltype = AA  length = 115
FEATURE                Location/Qualifiers
REGION                 1..115
                       note = Synthetic-Alb199
source                 1..115
                       mol_type = protein
                       organism = synthetic construct
SEQUENCE: 94
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VKVSS       115

SEQ ID NO: 95          moltype = AA  length = 116
FEATURE                Location/Qualifiers
REGION                 1..116
                       note = Synthetic-Alb199-A
source                 1..116
                       mol_type = protein
                       organism = synthetic construct
SEQUENCE: 95
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VKVSSA      116

SEQ ID NO: 96          moltype = AA  length = 116
FEATURE                Location/Qualifiers
REGION                 1..116
                       note = Synthetic-Alb223
source                 1..116
                       mol_type = protein
                       organism = synthetic construct
SEQUENCE: 96
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TALYYCTIGG SLSRSSQGTL VTVSSA      116

SEQ ID NO: 97          moltype = AA  length = 115
FEATURE                Location/Qualifiers
REGION                 1..115
                       note = Synthetic-Alb216
source                 1..115
                       mol_type = protein
                       organism = synthetic construct
SEQUENCE: 97
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TALYYCTIGG SLSRSSQGTL VKVSS       115

SEQ ID NO: 98          moltype = AA  length = 116
FEATURE                Location/Qualifiers
REGION                 1..116
                       note = Synthetic-Alb216-A
source                 1..116
                       mol_type = protein
                       organism = synthetic construct
SEQUENCE: 98
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TALYYCTIGG SLSRSSQGTL VKVSSA      116
```

```
SEQ ID NO: 99           moltype =   length =
SEQUENCE: 99
000

SEQ ID NO: 100          moltype = AA  length = 5
FEATURE                 Location/Qualifiers
REGION                  1..5
                        note = Synthetic-linker
source                  1..5
                        mol_type = protein
                        organism = synthetic construct
SEQUENCE: 100
GGGGS                                                                5

SEQ ID NO: 101          moltype = AA  length = 7
FEATURE                 Location/Qualifiers
REGION                  1..7
                        note = Synthetic-linker
source                  1..7
                        mol_type = protein
                        organism = synthetic construct
SEQUENCE: 101
SGGSGGS                                                              7

SEQ ID NO: 102          moltype = AA  length = 8
FEATURE                 Location/Qualifiers
REGION                  1..8
                        note = Synthetic-linker
source                  1..8
                        mol_type = protein
                        organism = synthetic construct
SEQUENCE: 102
GGGGSGGS                                                             8

SEQ ID NO: 103          moltype = AA  length = 9
FEATURE                 Location/Qualifiers
REGION                  1..9
                        note = Synthetic-linker
source                  1..9
                        mol_type = protein
                        organism = synthetic construct
SEQUENCE: 103
GGGGSGGGS                                                            9

SEQ ID NO: 104          moltype = AA  length = 10
FEATURE                 Location/Qualifiers
REGION                  1..10
                        note = Synthetic-linker
source                  1..10
                        mol_type = protein
                        organism = synthetic construct
SEQUENCE: 104
GGGGSGGGGS                                                           10

SEQ ID NO: 105          moltype = AA  length = 15
FEATURE                 Location/Qualifiers
REGION                  1..15
                        note = Synthetic-linker
source                  1..15
                        mol_type = protein
                        organism = synthetic construct
SEQUENCE: 105
GGGGSGGGGS GGGGS                                                     15

SEQ ID NO: 106          moltype = AA  length = 18
FEATURE                 Location/Qualifiers
REGION                  1..18
                        note = Synthetic-linker
source                  1..18
                        mol_type = protein
                        organism = synthetic construct
SEQUENCE: 106
GGGGSGGGGS GGGGSGGS                                                  18

SEQ ID NO: 107          moltype = AA  length = 20
FEATURE                 Location/Qualifiers
REGION                  1..20
                        note = Synthetic-linker
source                  1..20
```

```
                        mol_type = protein
                        organism = synthetic construct
SEQUENCE: 107
GGGGSGGGGS GGGGSGGGGS                                           20

SEQ ID NO: 108          moltype = AA  length = 25
FEATURE                 Location/Qualifiers
REGION                  1..25
                        note = Synthetic-linker
source                  1..25
                        mol_type = protein
                        organism = synthetic construct
SEQUENCE: 108
GGGGSGGGGS GGGGSGGGGS GGGGS                                     25

SEQ ID NO: 109          moltype = AA  length = 30
FEATURE                 Location/Qualifiers
REGION                  1..30
                        note = Synthetic-linker
source                  1..30
                        mol_type = protein
                        organism = synthetic construct
SEQUENCE: 109
GGGGSGGGGS GGGGSGGGGS GGGGSGGGGS                                30

SEQ ID NO: 110          moltype = AA  length = 35
FEATURE                 Location/Qualifiers
REGION                  1..35
                        note = Synthetic-linker
source                  1..35
                        mol_type = protein
                        organism = synthetic construct
SEQUENCE: 110
GGGGSGGGGS GGGGSGGGGS GGGGSGGGGS GGGGS                          35

SEQ ID NO: 111          moltype = AA  length = 40
FEATURE                 Location/Qualifiers
REGION                  1..40
                        note = Synthetic-linker
source                  1..40
                        mol_type = protein
                        organism = synthetic construct
SEQUENCE: 111
GGGGSGGGGS GGGGSGGGGS GGGGSGGGGS GGGGSGGGGS                     40

SEQ ID NO: 112          moltype = AA  length = 15
FEATURE                 Location/Qualifiers
REGION                  1..15
                        note = Synthetic-linker
source                  1..15
                        mol_type = protein
                        organism = synthetic construct
SEQUENCE: 112
EPKSCDKTHT CPPCP                                                15

SEQ ID NO: 113          moltype = AA  length = 24
FEATURE                 Location/Qualifiers
REGION                  1..24
                        note = Synthetic-linker
source                  1..24
                        mol_type = protein
                        organism = synthetic construct
SEQUENCE: 113
GGGGSGGGSE PKSCDKTHTC PPCP                                      24

SEQ ID NO: 114          moltype = AA  length = 12
FEATURE                 Location/Qualifiers
REGION                  1..12
                        note = Synthetic-linker
source                  1..12
                        mol_type = protein
                        organism = synthetic construct
SEQUENCE: 114
EPKTPKPQPA AA                                                   12

SEQ ID NO: 115          moltype = AA  length = 62
FEATURE                 Location/Qualifiers
REGION                  1..62
                        note = Synthetic-linker
```

```
source                  1..62
                        mol_type = protein
                        organism = synthetic construct
SEQUENCE: 115
ELKTPLGDTT HTCPRCPEPK SCDTPPPCPR CPEPKSCDTP PPCPRCPEPK SCDTPPPCPR  60
CP                                                                 62

SEQ ID NO: 116          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 116
VTVSS                                                              5

SEQ ID NO: 117          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 117
VKVSS                                                              5

SEQ ID NO: 118          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 118
VQVSS                                                              5

SEQ ID NO: 119          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 119
VTVKS                                                              5

SEQ ID NO: 120          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 120
VTVQS                                                              5

SEQ ID NO: 121          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 121
VKVKS                                                              5

SEQ ID NO: 122          moltype = AA  length = 5
FEATURE                 Location/Qualifiers
REGION                  1..5
                        note = Synthetic-C-terminus
source                  1..5
                        mol_type = protein
                        organism = synthetic construct
SEQUENCE: 122
VKVQS                                                              5

SEQ ID NO: 123          moltype = AA  length = 5
FEATURE                 Location/Qualifiers
```

```
REGION              1..5
                    note = Synthetic-C-terminus
source              1..5
                    mol_type = protein
                    organism = synthetic construct
SEQUENCE: 123
VQVKS                                                                5

SEQ ID NO: 124      moltype = AA  length = 5
FEATURE             Location/Qualifiers
REGION              1..5
                    note = Synthetic-C-terminus
source              1..5
                    mol_type = protein
                    organism = synthetic construct
SEQUENCE: 124
VQVQS                                                                5

SEQ ID NO: 125      moltype = AA  length = 6
FEATURE             Location/Qualifiers
REGION              1..6
                    note = Synthetic-C-terminus
source              1..6
                    mol_type = protein
                    organism = synthetic construct
SEQUENCE: 125
VTVSSA                                                               6

SEQ ID NO: 126      moltype = AA  length = 6
FEATURE             Location/Qualifiers
REGION              1..6
                    note = Synthetic-C-terminus
source              1..6
                    mol_type = protein
                    organism = synthetic construct
SEQUENCE: 126
VKVSSA                                                               6

SEQ ID NO: 127      moltype = AA  length = 6
FEATURE             Location/Qualifiers
REGION              1..6
                    note = Synthetic-C-terminus
source              1..6
                    mol_type = protein
                    organism = synthetic construct
SEQUENCE: 127
VQVSSA                                                               6

SEQ ID NO: 128      moltype = AA  length = 6
FEATURE             Location/Qualifiers
REGION              1..6
                    note = Synthetic-C-terminus
source              1..6
                    mol_type = protein
                    organism = synthetic construct
SEQUENCE: 128
VTVKSA                                                               6

SEQ ID NO: 129      moltype = AA  length = 6
FEATURE             Location/Qualifiers
REGION              1..6
                    note = Synthetic-C-terminus
source              1..6
                    mol_type = protein
                    organism = synthetic construct
SEQUENCE: 129
VTVQSA                                                               6

SEQ ID NO: 130      moltype = AA  length = 6
FEATURE             Location/Qualifiers
REGION              1..6
                    note = Synthetic-C-terminus
source              1..6
                    mol_type = protein
                    organism = synthetic construct
SEQUENCE: 130
VKVKSA                                                               6

SEQ ID NO: 131      moltype = AA  length = 6
```

```
FEATURE                Location/Qualifiers
REGION                 1..6
                       note = Synthetic-C-terminus
source                 1..6
                       mol_type = protein
                       organism = synthetic construct
SEQUENCE: 131
VKVQSA                                                                 6

SEQ ID NO: 132         moltype = AA  length = 6
FEATURE                Location/Qualifiers
REGION                 1..6
                       note = Synthetic-C-terminus
source                 1..6
                       mol_type = protein
                       organism = synthetic construct
SEQUENCE: 132
VQVKSA                                                                 6

SEQ ID NO: 133         moltype = AA  length = 6
FEATURE                Location/Qualifiers
REGION                 1..6
                       note = Synthetic-C-terminus
source                 1..6
                       mol_type = protein
                       organism = synthetic construct
SEQUENCE: 133
VQVQSA                                                                 6

SEQ ID NO: 134         moltype = AA  length = 580
FEATURE                Location/Qualifiers
REGION                 1..580
                       note = Synthetic-Human GPC3 (P51654)
source                 1..580
                       mol_type = protein
                       organism = synthetic construct
SEQUENCE: 134
MAGTVRTACL VVAMLLSLDF PGQAQPPPPP PDATCHQVRS FFQRLQPGLK WVPETPVPGS  60
DLQVCLPKGP TCCSRKMEEK YQLTARLNME QLLQSASMEL KFLIIQNAAV FQEAFEIVVR  120
HAKNYTNAMF KNNYPSLTPQ AFEFVGEFFT DVSLYILGSD INVDDMVNEL FDSLFPVIYT  180
QLMNPGLPDS ALDINECLRG ARRDLKVFGN FPKLIMTQVS KSLQVTRIFL QALNLGIEVI  240
NTTDHLKFSK DCGRMLTRMW YCSYCQGLMM VKPCGGYCNV VMQGCMAGVV EIDKYWREYI  300
LSLEELVNGM YRIYDMENVL LGLFSTIHDS IQYVQKNAGK LTTTIGKLCA HSQQRQYRSA  360
YYPEDLFIDK KVLKVAHVEH EETLSSRRRE LIQKLKSFIS FYSALPGYIC SHSPVAENDT  420
LCWNGQELVE RYSQKAARNG MKNQFNLHEL KMKGPEPVVS QIIDKLKHIN QLLRTMSMPK  480
GRVLDKNLDE EGFESGDCGD DEDECIGGSG DGMIKVKNQL RFLAELAYDL DVDDAPGNSQ  540
QATPKDNEIS TFHNLGNVHS PLKLLTSMAI SVVCFFFLVH                        580

SEQ ID NO: 135         moltype = AA  length = 96
FEATURE                Location/Qualifiers
REGION                 1..96
                       note = Synthetic-Human TCR alpha constant domain (derived
                        from P01848)
source                 1..96
                       mol_type = protein
                       organism = synthetic construct
SEQUENCE: 135
PNIQNPDPAV YQLRDSKSSD KSVCLFTDFD SQTNVSQSKD SDVYITDKTV LDMRSMDFKS  60
NSAVAWSNKS DFACANAFNN SIIPEDTFFP SPESSC                              96

SEQ ID NO: 136         moltype = AA  length = 131
FEATURE                Location/Qualifiers
REGION                 1..131
                       note = Synthetic-Human TCR beta constant domain (derived
                        from P01850)
source                 1..131
                       mol_type = protein
                       organism = synthetic construct
SEQUENCE: 136
EDLNKVFPPE VAVFEPSEAE ISHTQKATLV CLATGFFPDH VELSWWVNGK EVHSGVSTDP  60
QPLKEQPALN DSRYALSSRL RVSATFWQNP RNHFRCQVQF YGLSENDEWT QDRAKPVTQI  120
VSAEAWGRAD C                                                         131

SEQ ID NO: 137         moltype = AA  length = 4
FEATURE                Location/Qualifiers
REGION                 1..4
                       note = Synthetic-Motif from Table A-0
source                 1..4
                       mol_type = protein
```

```
                        organism = synthetic construct
SEQUENCE: 137
KERE                                                                4

SEQ ID NO: 138          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 138
KQRE                                                                4

SEQ ID NO: 139          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 139
GLEW                                                                4

SEQ ID NO: 140          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 140
KEREL                                                               5

SEQ ID NO: 141          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 141
KEREF                                                               5

SEQ ID NO: 142          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 142
KQREL                                                               5

SEQ ID NO: 143          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 143
KQREF                                                               5

SEQ ID NO: 144          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 144
KEREG                                                               5

SEQ ID NO: 145          moltype = AA  length = 5
FEATURE                 Location/Qualifiers
REGION                  1..5
                        note = Synthetic-Motif from Table A-0
source                  1..5
```

```
                        mol_type = protein
                        organism = synthetic construct
SEQUENCE: 145
KQREW                                                        5

SEQ ID NO: 146          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 146
KQREG                                                        5

SEQ ID NO: 147          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 147
TERE                                                         4

SEQ ID NO: 148          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 148
TEREL                                                        5

SEQ ID NO: 149          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 149
TQRE                                                         4

SEQ ID NO: 150          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 150
TQREL                                                        5

SEQ ID NO: 151          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 151
KECE                                                         4

SEQ ID NO: 152          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 152
KECEL                                                        5

SEQ ID NO: 153          moltype = AA  length = 5
FEATURE                 Location/Qualifiers
REGION                  1..5
                        note = Synthetic-Motif from Table A-0
```

```
source                  1..5
                        mol_type = protein
                        organism = synthetic construct
SEQUENCE: 153
KECER                                                                       5

SEQ ID NO: 154          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 154
KQCE                                                                        4

SEQ ID NO: 155          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 155
KQCEL                                                                       5

SEQ ID NO: 156          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 156
RERE                                                                        4

SEQ ID NO: 157          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 157
REREG                                                                       5

SEQ ID NO: 158          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 158
RQRE                                                                        4

SEQ ID NO: 159          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 159
RQREL                                                                       5

SEQ ID NO: 160          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 160
RQREF                                                                       5

SEQ ID NO: 161          moltype = AA  length = 5
FEATURE                 Location/Qualifiers
REGION                  1..5
```

```
                        note = Synthetic-Motif from Table A-0
source                  1..5
                        mol_type = protein
                        organism = synthetic construct
SEQUENCE: 161
RQREW                                                                5

SEQ ID NO: 162          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 162
QERE                                                                 4

SEQ ID NO: 163          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 163
QEREG                                                                5

SEQ ID NO: 164          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 164
QQRE                                                                 4

SEQ ID NO: 165          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 165
QQREW                                                                5

SEQ ID NO: 166          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 166
QQREL                                                                5

SEQ ID NO: 167          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 167
QQREF                                                                5

SEQ ID NO: 168          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 168
KGRE                                                                 4

SEQ ID NO: 169          moltype = AA  length = 5
FEATURE                 Location/Qualifiers
```

```
REGION                  1..5
                        note = Synthetic-Motif from Table A-0
source                  1..5
                        mol_type = protein
                        organism = synthetic construct
SEQUENCE: 169
KGREG                                                            5

SEQ ID NO: 170          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 170
KDRE                                                             4

SEQ ID NO: 171          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 171
KDREV                                                            5

SEQ ID NO: 172          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 172
DECKL                                                            5

SEQ ID NO: 173          moltype = AA  length = 5
FEATURE                 Location/Qualifiers
REGION                  1..5
                        note = Synthetic-Motif from Table A-0
source                  1..5
                        mol_type = protein
                        organism = synthetic construct
SEQUENCE: 173
NVCEL                                                            5

SEQ ID NO: 174          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 174
GVEW                                                             4

SEQ ID NO: 175          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 175
EPEW                                                             4

SEQ ID NO: 176          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 176
GLER                                                             4

SEQ ID NO: 177          moltype = AA  length = 4
```

```
FEATURE                 Location/Qualifiers
REGION                  1..4
                        note = Synthetic-Motif from Table A-0
source                  1..4
                        mol_type = protein
                        organism = synthetic construct
SEQUENCE: 177
DQEW                                                                        4

SEQ ID NO: 178          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 178
DLEW                                                                        4

SEQ ID NO: 179          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 179
GIEW                                                                        4

SEQ ID NO: 180          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 180
ELEW                                                                        4

SEQ ID NO: 181          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 181
GPEW                                                                        4

SEQ ID NO: 182          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 182
EWLP                                                                        4

SEQ ID NO: 183          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 183
GPER                                                                        4

SEQ ID NO: 184          moltype = AA  length = 4
FEATURE                 Location/Qualifiers
REGION                  1..4
                        note = Synthetic-Motif from Table A-0
source                  1..4
                        mol_type = protein
                        organism = synthetic construct
SEQUENCE: 184
GLER                                                                        4
```

-continued

```
SEQ ID NO: 185          moltype = AA  length = 4
FEATURE                 Location/Qualifiers
REGION                  1..4
                        note = Synthetic-Motif from Table A-0
source                  1..4
                        mol_type = protein
                        organism = synthetic construct

SEQUENCE: 185
ELEW                                                              4
```

The invention claimed is:

1. A polypeptide that comprises an immunoglobulin single variable domain (ISVD) that specifically binds GPC3, wherein said ISVD comprises three complementarity determining regions (CDR1 to CDR3, respectively), and wherein the ISVD comprises:

a) a CDR1 that comprises the amino acid sequence of SEQ ID NO: 7; a CDR2 that comprises the amino acid sequence of SEQ ID NO: 11 or an amino acid sequence with 1 amino acid difference with SEQ ID NO: 11, wherein the amino acid difference occurs at the fifth amino acid of SEQ ID NO: 11, and wherein any amino acid difference that occurs at the fifth amino acid of SEQ ID NO: 11 is selected from the group consisting of a substitution of lysine with glycine and a substitution of lysine with alanine; and a CDR3 that comprises the amino acid sequence of SEQ ID NO: 15, b) a CDR1 that comprises the amino acid sequence of SEQ ID NO: 8; a CDR2 that comprises the amino acid sequence of SEQ ID NO: 12 or an amino acid sequence with 2 or 1 amino acid difference(s) with SEQ ID NO: 12, wherein the amino acid difference that occurs at the sixth amino acid of SEQ ID NO: 12 is a substitution of glutamate with aspartate, and wherein the amino acid difference that occurs at the ninth amino acid of SEQ ID NO: 12 is a substitution of tyrosine with asparagine; and a CDR3 that comprises the amino acid sequence of GVA, c) a CDR1 that comprises the amino acid sequence of SEQ ID NO: 32; a CDR2 that comprises the amino acid sequence of SEQ ID NO: 36 or an amino acid sequence with 2 or 1 amino acid difference(s) with SEQ ID NO: 36, wherein the amino acid difference that occurs at the fifth amino acid of SEQ ID NO: 36 is selected from the group consisting of a substitution of lysine with glycine and a substitution of lysine with alanine, and wherein the amino acid difference that occurs at the eleventh amino acid of SEQ ID NO: 36 is a substitution of alanine with arginine; and a CDR3 that comprises the amino acid sequence of SEQ ID NO: 15, or d) a CDR1 that comprises the amino acid sequence of SEQ ID NO: 33; a CDR2 that comprises the amino acid sequence of SEQ ID NO: 37 or an amino acid sequence with 2 or 1 amino acid difference(s) with SEQ ID NO: 37, wherein the amino acid difference that occurs at the sixth amino acid of SEQ ID NO: 37 is a substitution of glutamate with aspartate, and wherein the amino acid difference that occurs at the ninth amino acid of SEQ ID NO: 37 is a substitution of tyrosine with asparagine; and a CDR3 that comprises the amino acid sequence of GVA.

2. The polypeptide according to claim 1, wherein said polypeptide further comprises one or more other groups, residues, moieties or binding units, in which said one or more other groups, residues, moieties or binding units provide the polypeptide with increased half-life, compared to the corresponding polypeptide without said one or more other groups, residues, moieties or binding units.

3. The polypeptide according to claim 1, in which said binding unit that provides the polypeptide with increased half-life is an ISVD that binds to human serum albumin, wherein said ISVD that binds to human serum albumin comprises;

a CDR1 that comprises the amino acid sequence of SEQ ID NO: 9, a CDR2 that comprises the amino acid sequence of SEQ ID NO: 13, and a CDR3 that comprises the amino acid sequence of SEQ ID NO: 17; or a CDR1 that comprises the amino acid sequence of SEQ ID NO: 34, a CDR2 that comprises the amino acid sequence of SEQ ID NO: 38, and a CDR3 that comprises the amino acid sequence of SEQ ID NO: 17.

4. The polypeptide according to claim 3, wherein the amino acid sequence of said ISVD binding to human serum albumin exhibits a sequence identity of more than 90% with SEQ ID NO: 5, or wherein said ISVD binding to human serum albumin consists of the amino acid sequence of SEQ ID NO: 5.

5. A nucleic acid comprising a nucleotide sequence that encodes a polypeptide according to claim 1.

6. A host or host cell comprising a nucleic acid according to claim 5.

7. A method for producing a polypeptide, said method comprising the step of expressing, in a suitable host cell or host organism or in another suitable expression system, a nucleic acid according to claim 5.

8. A composition comprising at least one polypeptide according to claim 1.

9. The composition according to claim 8, which is a pharmaceutical composition which further comprises at least one pharmaceutically acceptable carrier, diluent or excipient and/or adjuvant.

10. A method of treating cancer, wherein said method comprises administering, to a subject in need thereof, a pharmaceutically active amount of a polypeptide according to claim 1, wherein the cancer is a liver cancer or a lung cancer.

* * * * *